(12) United States Patent
Jacobson et al.

(10) Patent No.: US 11,084,014 B2
(45) Date of Patent: Aug. 10, 2021

(54) METHODS AND DEVICES FOR NUCLEIC ACIDS SYNTHESIS

(71) Applicant: Gen9, Inc., Boston, MA (US)

(72) Inventors: Joseph Jacobson, Newton, MA (US); Li-yun A. Kung, Arlington, MA (US); Andrew Kirk Wilson, Arlington, MA (US); Senthil Ramu, Boston, MA (US); Daniel Schindler, Newton, MA (US); Michael Hudson, Framingham, MA (US)

(73) Assignee: Gen9, Inc., Boston, MA (US)

( * ) Notice: Subject to any disclaimer, the term of this patent is extended or adjusted under 35 U.S.C. 154(b) by 0 days.

(21) Appl. No.: 16/533,892

(22) Filed: Aug. 7, 2019

(65) Prior Publication Data

US 2020/0197896 A1 Jun. 25, 2020

Related U.S. Application Data

(63) Continuation of application No. 15/054,038, filed on Feb. 25, 2016, now abandoned, which is a
(Continued)

(51) Int. Cl.
*C12Q 1/68* (2018.01)
*B01J 19/00* (2006.01)
(Continued)

(52) U.S. Cl.
CPC .......... *B01J 19/0046* (2013.01); *C12N 15/10* (2013.01); *C12N 15/1031* (2013.01);
(Continued)

(58) Field of Classification Search
CPC ....................................................... C12Q 1/68
See application file for complete search history.

(56) References Cited

U.S. PATENT DOCUMENTS

| 4,500,707 A | 2/1985 | Caruthers et al. |
| 4,683,195 A | 7/1987 | Mullis et al. |
| | (Continued) | |

FOREIGN PATENT DOCUMENTS

| CN | 1145641 A | 3/1997 |
| CN | 1468313 A | 1/2004 |
| | (Continued) | |

OTHER PUBLICATIONS

Extended European Search Report dated Jan. 11, 2016, for Application No. EP 15177553.3.
(Continued)

*Primary Examiner* — Aaron A Priest
(74) *Attorney, Agent, or Firm* — Wolf, Greenfield & Sacks, P.C.

(57) ABSTRACT

Methods and apparatus relate to the synthesis of polynucleotides having a predefined sequence on a support. Assembly methods include primer extension to generate overlapping construction oligonucleotides and assembly of the polynucleotides of interest onto an anchor support-bound oligonucleotides. Methods and apparatus for selection of polynucleotides having the predefined sequence and/or length are disclosed.

12 Claims, 17 Drawing Sheets

Related U.S. Application Data continuation of application No. 13/884,463, filed as application No. PCT/US2011/060243 on Nov. 10, 2011, now Pat. No. 9,295,965.

(60) Provisional application No. 61/503,722, filed on Jul. 1, 2011, provisional application No. 61/466,814, filed on Mar. 23, 2011, provisional application No. 61/418,095, filed on Nov. 30, 2010, provisional application No. 61/412,937, filed on Nov. 12, 2010.

(51) Int. Cl.
*C12N 15/10* (2006.01)
*C12N 15/66* (2006.01)
C12P 19/34 (2006.01)

(52) U.S. Cl.
CPC ..... *C12N 15/66* (2013.01); *B01J 2219/00585* (2013.01); *B01J 2219/00596* (2013.01); *B01J 2219/00722* (2013.01); *C12P 19/34* (2013.01)

(56) References Cited

U.S. PATENT DOCUMENTS

| | | |
|---|---|---|
| 4,683,202 A | 7/1987 | Mullis |
| 4,689,405 A | 8/1987 | Frank et al. |
| 4,725,677 A | 2/1988 | Koester et al. |
| 4,800,159 A | 1/1989 | Mullis et al. |
| 4,888,286 A | 12/1989 | Crea |
| 4,959,317 A | 9/1990 | Sauer |
| 4,965,188 A | 10/1990 | Mullis et al. |
| 4,999,294 A | 3/1991 | Looney et al. |
| 5,047,524 A | 9/1991 | Andrus et al. |
| 5,093,251 A | 3/1992 | Richards et al. |
| 5,096,825 A | 3/1992 | Barr et al. |
| 5,104,789 A | 4/1992 | Permar et al. |
| 5,104,792 A | 4/1992 | Silver et al. |
| 5,132,215 A | 7/1992 | Jayaraman et al. |
| 5,143,854 A | 9/1992 | Pirrung et al. |
| 5,288,514 A | 2/1994 | Ellman |
| 5,356,802 A | 10/1994 | Chandrasegaran |
| 5,384,261 A | 1/1995 | Winkler et al. |
| 5,395,750 A | 3/1995 | Dillon et al. |
| 5,405,783 A | 4/1995 | Pirrung et al. |
| 5,424,186 A | 6/1995 | Fodor et al. |
| 5,436,150 A | 7/1995 | Chandrasegaran |
| 5,436,327 A | 7/1995 | Southern et al. |
| 5,445,934 A | 8/1995 | Fodor et al. |
| 5,459,039 A | 10/1995 | Modrich et al. |
| 5,474,796 A | 12/1995 | Brennan |
| 5,498,531 A | 3/1996 | Jarrell |
| 5,508,169 A | 4/1996 | Deugau et al. |
| 5,510,270 A | 4/1996 | Fodor et al. |
| 5,512,463 A | 4/1996 | Stemmer |
| 5,514,789 A | 5/1996 | Kempe |
| 5,527,681 A | 6/1996 | Holmes |
| 5,541,061 A | 7/1996 | Fodor et al. |
| 5,556,750 A | 9/1996 | Modrich et al. |
| 5,604,097 A | 2/1997 | Brenner |
| 5,605,793 A | 2/1997 | Stemmer |
| 5,624,711 A | 4/1997 | Sundberg et al. |
| 5,639,603 A | 6/1997 | Dower et al. |
| 5,641,658 A | 6/1997 | Adams et al. |
| 5,653,939 A | 8/1997 | Hollis et al. |
| 5,674,742 A | 10/1997 | Northrup et al. |
| 5,679,522 A | 10/1997 | Modrich et al. |
| 5,695,940 A | 12/1997 | Drmanac et al. |
| 5,700,637 A | 12/1997 | Southern |
| 5,700,642 A | 12/1997 | Monforte et al. |
| 5,702,894 A | 12/1997 | Modrich et al. |
| 5,738,829 A | 4/1998 | Kempe |
| 5,739,386 A | 4/1998 | Holmes |
| 5,750,335 A | 5/1998 | Gifford |
| 5,766,550 A | 6/1998 | Kaplan et al. |
| 5,770,358 A | 6/1998 | Dower et al. |
| 5,780,272 A | 7/1998 | Jarrell |
| 5,795,714 A | 8/1998 | Cantor et al. |
| 5,830,655 A | 11/1998 | Monforte et al. |
| 5,830,721 A | 11/1998 | Stemmer et al. |
| 5,834,252 A | 11/1998 | Stemmer et al. |
| 5,858,754 A | 1/1999 | Modrich et al. |
| 5,861,482 A | 1/1999 | Modrich et al. |
| 5,871,902 A | 2/1999 | Weininger et al. |
| 5,877,280 A | 3/1999 | Wetmur |
| 5,912,129 A | 6/1999 | Vinayagamoorthy et al. |
| 5,916,794 A | 6/1999 | Chandrasegaran |
| 5,922,539 A | 7/1999 | Modrich et al. |
| 5,928,905 A | 7/1999 | Stemmer et al. |
| 5,929,208 A | 7/1999 | Heller et al. |
| 5,942,609 A | 8/1999 | Hunkapiller et al. |
| 5,953,469 A | 9/1999 | Zhou |
| 6,008,031 A | 12/1999 | Modrich et al. |
| 6,013,440 A | 1/2000 | Lipshutz et al. |
| 6,017,696 A | 1/2000 | Heller |
| 6,027,877 A | 2/2000 | Wagner, Jr. |
| 6,042,211 A | 3/2000 | Hudson et al. |
| 6,093,302 A | 7/2000 | Montgomery |
| 6,103,463 A | 8/2000 | Chetverin et al. |
| 6,110,668 A | 8/2000 | Strizhov et al. |
| 6,136,568 A | 10/2000 | Hiatt et al. |
| 6,143,527 A | 11/2000 | Pachuk et al. |
| 6,150,102 A | 11/2000 | Mills, Jr. et al. |
| 6,150,141 A | 11/2000 | Jarrell |
| 6,165,793 A | 12/2000 | Stemmer |
| 6,177,558 B1 | 1/2001 | Brennan et al. |
| 6,242,211 B1 | 6/2001 | Peterson et al. |
| 6,248,521 B1 | 6/2001 | Van Ness et al. |
| 6,261,797 B1 | 7/2001 | Sorge et al. |
| 6,271,957 B1 | 8/2001 | Quate et al. |
| 6,277,632 B1 | 8/2001 | Harney |
| 6,280,595 B1 | 8/2001 | Montgomery |
| 6,284,463 B1 | 9/2001 | Hasebe et al. |
| 6,287,825 B1 | 9/2001 | Weissman et al. |
| 6,287,861 B1 | 9/2001 | Stemmer et al. |
| 6,291,242 B1 | 9/2001 | Stemmer |
| 6,315,958 B1 | 11/2001 | Singh-Gasson et al. |
| 6,322,971 B1 | 11/2001 | Chetverin et al. |
| 6,326,489 B1 | 12/2001 | Church et al. |
| 6,333,153 B1 | 12/2001 | Fishel et al. |
| 6,346,399 B1 | 2/2002 | Weissman et al. |
| 6,355,412 B1 | 3/2002 | Stewart et al. |
| 6,355,423 B1 | 3/2002 | Rothberg et al. |
| 6,358,712 B1 | 3/2002 | Jarrell et al. |
| 6,365,355 B1 | 4/2002 | McCutchen-Maloney |
| 6,372,429 B1 | 4/2002 | Sharon |
| 6,372,434 B1 | 4/2002 | Weissman |
| 6,372,484 B1 | 4/2002 | Ronchi et al. |
| 6,375,903 B1 | 4/2002 | Cerrina et al. |
| 6,376,246 B1 | 4/2002 | Crameri et al. |
| 6,406,847 B1 | 6/2002 | Cox et al. |
| 6,410,220 B1 | 6/2002 | Hodgson |
| 6,416,164 B1 | 7/2002 | Stearns et al. |
| 6,426,184 B1 | 7/2002 | Gao et al. |
| 6,432,360 B1 | 8/2002 | Church |
| 6,444,111 B1 | 9/2002 | Montgomery |
| 6,444,175 B1 | 9/2002 | Singh-Gasson et al. |
| 6,444,650 B1 | 9/2002 | Cech et al. |
| 6,444,661 B1 | 9/2002 | Barton et al. |
| 6,472,184 B1 | 10/2002 | Hegemann et al. |
| 6,479,652 B1 | 11/2002 | Crameri et al. |
| 6,480,324 B2 | 11/2002 | Quate et al. |
| 6,489,146 B2 | 12/2002 | Stemmer |
| 6,495,318 B2 | 12/2002 | Harney |
| 6,506,603 B1 | 1/2003 | Stemmer |
| 6,509,156 B1 | 1/2003 | Stewart |
| 6,511,849 B1 | 1/2003 | Wang |
| 6,514,704 B2 | 2/2003 | Bruce et al. |
| 6,521,427 B1 | 2/2003 | Evans |
| 6,534,271 B2 | 3/2003 | Furste |
| 6,537,776 B1 | 3/2003 | Short |
| 6,565,727 B1 | 5/2003 | Shenderov |
| 6,586,211 B1 | 7/2003 | Stahler et al. |
| 6,593,111 B2 | 7/2003 | Baric et al. |
| 6,596,239 B2 | 7/2003 | Williams et al. |

(56) References Cited

U.S. PATENT DOCUMENTS

| | | |
|---|---|---|
| 6,605,451 B1 | 8/2003 | Marmaro et al. |
| 6,610,499 B1 | 8/2003 | Fulwyler et al. |
| 6,613,581 B1 | 9/2003 | Wada et al. |
| 6,632,641 B1 | 10/2003 | Brennan |
| 6,650,822 B1 | 11/2003 | Zhou |
| 6,658,802 B2 | 12/2003 | Lucas, Jr. et al. |
| 6,660,475 B2 | 12/2003 | Jack et al. |
| 6,664,112 B2 | 12/2003 | Mulligan et al. |
| 6,664,388 B2 | 12/2003 | Nelson |
| 6,670,127 B2 | 12/2003 | Evans |
| 6,670,605 B1 | 12/2003 | Storm, Jr. et al. |
| 6,800,439 B1 | 10/2004 | McGall et al. |
| 6,802,593 B2 | 10/2004 | Ellson et al. |
| 6,824,866 B1 | 11/2004 | Glazer et al. |
| 6,830,890 B2 | 12/2004 | Lockhart et al. |
| 6,833,450 B1 | 12/2004 | Mcgall et al. |
| 6,846,655 B1 | 1/2005 | Wagner et al. |
| 6,897,025 B2 | 5/2005 | Cox et al. |
| 6,911,132 B2 | 6/2005 | Pamula et al. |
| 6,921,818 B2 | 7/2005 | Sproat |
| 6,932,097 B2 | 8/2005 | Ellson et al. |
| 6,946,296 B2 | 9/2005 | Patten et al. |
| 6,955,901 B2 | 10/2005 | Schouten |
| 6,969,587 B2 | 11/2005 | Taylor |
| 6,969,847 B2 | 11/2005 | Davis et al. |
| 7,090,333 B2 | 8/2006 | Mutz et al. |
| 7,133,782 B2 | 11/2006 | Odedra |
| 7,144,734 B2 | 12/2006 | Court et al. |
| 7,169,560 B2 | 1/2007 | Lapidus et al. |
| 7,179,423 B2 | 2/2007 | Bohm et al. |
| 7,183,406 B2 | 2/2007 | Belshaw |
| 7,199,233 B1 | 4/2007 | Jensen et al. |
| 7,262,031 B2 | 8/2007 | Lathrop |
| 7,273,730 B2 | 9/2007 | Du Breuil Lastrucci |
| 7,303,320 B1 | 12/2007 | Ashley |
| 7,303,872 B2 | 12/2007 | Sussman |
| 7,323,320 B2 | 1/2008 | Oleinikov |
| 7,399,590 B2 | 7/2008 | Piepenburg et al. |
| 7,432,055 B2 | 10/2008 | Pemov et al. |
| 7,498,176 B2 | 3/2009 | McCormick et al. |
| 7,537,897 B2 | 5/2009 | Brenner et al. |
| 7,563,600 B2 | 7/2009 | Oleinikov |
| 7,723,077 B2 | 5/2010 | Young et al. |
| 7,820,412 B2 | 10/2010 | Belshaw et al. |
| 7,879,580 B2 | 2/2011 | Carr et al. |
| 7,932,025 B2 | 4/2011 | Carr et al. |
| 8,053,191 B2 | 11/2011 | Blake |
| 8,058,004 B2 | 11/2011 | Oleinikov |
| 8,137,906 B2 | 3/2012 | Schatz |
| 8,173,368 B2 | 5/2012 | Staehler et al. |
| 8,338,091 B2 | 12/2012 | Chesnut et al. |
| 8,476,018 B2 | 7/2013 | Brenner |
| 8,716,467 B2 | 5/2014 | Jacobson |
| 8,808,986 B2 | 8/2014 | Jacobson et al. |
| 9,023,601 B2 | 5/2015 | Oleinikov |
| 9,023,649 B2 | 5/2015 | Mali et al. |
| 9,051,666 B2 | 6/2015 | Oleinikov |
| 9,150,853 B2 | 10/2015 | Hudson et al. |
| 9,295,965 B2 | 3/2016 | Jacobson et al. |
| 9,322,037 B2 | 4/2016 | Liu et al. |
| 9,752,176 B2 | 9/2017 | Kung et al. |
| 2001/0012537 A1 | 8/2001 | Anderson et al. |
| 2001/0031483 A1 | 10/2001 | Sorge et al. |
| 2001/0049125 A1 | 12/2001 | Stemmer et al. |
| 2001/0053519 A1 | 12/2001 | Fodor et al. |
| 2002/0012616 A1 | 1/2002 | Zhou et al. |
| 2002/0025561 A1 | 2/2002 | Hodgson |
| 2002/0037579 A1 | 3/2002 | Ellson et al. |
| 2002/0058275 A1 | 5/2002 | Fishel et al. |
| 2002/0081582 A1 | 6/2002 | Gao et al. |
| 2002/0127552 A1 | 9/2002 | Church et al. |
| 2002/0132259 A1 | 9/2002 | Wagner et al. |
| 2002/0132308 A1 | 9/2002 | Liu et al. |
| 2002/0133359 A1 | 9/2002 | Brown |
| 2003/0017552 A1 | 1/2003 | Jarrell et al. |
| 2003/0044980 A1 | 3/2003 | Mancebo et al. |
| 2003/0047688 A1 | 3/2003 | Faris et al. |
| 2003/0050437 A1 | 3/2003 | Montgomery |
| 2003/0050438 A1 | 3/2003 | Montgomery |
| 2003/0054390 A1 | 3/2003 | Crameri et al. |
| 2003/0068633 A1 | 4/2003 | Belshaw et al. |
| 2003/0068643 A1 | 4/2003 | Brennan et al. |
| 2003/0082630 A1 | 5/2003 | Kolkman et al. |
| 2003/0087298 A1 | 5/2003 | Green et al. |
| 2003/0091476 A1 | 5/2003 | Zhou et al. |
| 2003/0099952 A1 | 5/2003 | Green et al. |
| 2003/0118485 A1 | 6/2003 | Singh-Gasson et al. |
| 2003/0118486 A1 | 6/2003 | Zhou et al. |
| 2003/0120035 A1 | 6/2003 | Gao et al. |
| 2003/0134807 A1 | 7/2003 | Hardin et al. |
| 2003/0143550 A1 | 7/2003 | Green et al. |
| 2003/0143724 A1 | 7/2003 | Cerrina et al. |
| 2003/0165841 A1 | 9/2003 | Burgin et al. |
| 2003/0170616 A1 | 9/2003 | Wang et al. |
| 2003/0171325 A1 | 9/2003 | Gascoyne et al. |
| 2003/0175907 A1 | 9/2003 | Frazer et al. |
| 2003/0186226 A1 | 10/2003 | Brennan et al. |
| 2003/0198948 A1 | 10/2003 | Stahler et al. |
| 2003/0215837 A1 | 11/2003 | Frey et al. |
| 2003/0215855 A1 | 11/2003 | Dubrow et al. |
| 2003/0215856 A1 | 11/2003 | Church et al. |
| 2003/0219781 A1 | 11/2003 | Frey |
| 2003/0224521 A1 | 12/2003 | Court et al. |
| 2004/0002103 A1 | 1/2004 | Short |
| 2004/0005673 A1 | 1/2004 | Jarrell et al. |
| 2004/0009479 A1 | 1/2004 | Wohlgemuth et al. |
| 2004/0009520 A1 | 1/2004 | Albert et al. |
| 2004/0014083 A1 | 1/2004 | Yuan et al. |
| 2004/0053362 A1 | 3/2004 | De Luca et al. |
| 2004/0096891 A1 | 5/2004 | Bennett |
| 2004/0101444 A1 | 5/2004 | Sommers et al. |
| 2004/0101894 A1 | 5/2004 | Albert et al. |
| 2004/0101949 A1 | 5/2004 | Green et al. |
| 2004/0106728 A1 | 6/2004 | McGall et al. |
| 2004/0110211 A1 | 6/2004 | McCormick et al. |
| 2004/0110212 A1 | 6/2004 | McCormick et al. |
| 2004/0126757 A1 | 7/2004 | Cerrina |
| 2004/0132029 A1 | 7/2004 | Sussman et al. |
| 2004/0166567 A1 | 8/2004 | Santi et al. |
| 2004/0171047 A1 | 9/2004 | Dahl et al. |
| 2004/0185484 A1 | 9/2004 | Costa et al. |
| 2004/0229359 A1 | 11/2004 | Mead et al. |
| 2004/0241655 A1 | 12/2004 | Hwang et al. |
| 2004/0259146 A1 | 12/2004 | Friend et al. |
| 2005/0053997 A1 | 3/2005 | Evans |
| 2005/0069928 A1 | 3/2005 | Nelson et al. |
| 2005/0079510 A1 | 4/2005 | Berka et al. |
| 2005/0089889 A1 | 4/2005 | Ramsing et al. |
| 2005/0106606 A1 | 5/2005 | Parker et al. |
| 2005/0118628 A1 | 6/2005 | Evans |
| 2005/0202429 A1 | 9/2005 | Trau et al. |
| 2005/0208503 A1 | 9/2005 | Yowanto et al. |
| 2005/0221340 A1 | 10/2005 | Evans |
| 2005/0227235 A1 | 10/2005 | Carr et al. |
| 2005/0227316 A1 | 10/2005 | Santi et al. |
| 2005/0255477 A1* | 11/2005 | Carr .................. C12P 19/34 |
| | | 435/6.16 |
| 2005/0287585 A1 | 12/2005 | Oleinikov |
| 2006/0003347 A1 | 1/2006 | Griffiths et al. |
| 2006/0008833 A1 | 1/2006 | Jacobson |
| 2006/0014146 A1 | 1/2006 | Sucaille et al. |
| 2006/0035218 A1 | 2/2006 | Oleinikov |
| 2006/0040297 A1 | 2/2006 | Leamon et al. |
| 2006/0054503 A1 | 3/2006 | Pamula et al. |
| 2006/0127920 A1 | 6/2006 | Church et al. |
| 2006/0127926 A1 | 6/2006 | Belshaw et al. |
| 2006/0134638 A1 | 6/2006 | Mulligan et al. |
| 2006/0160138 A1 | 7/2006 | Church et al. |
| 2006/0194214 A1 | 8/2006 | Church et al. |
| 2006/0281113 A1* | 12/2006 | Church .................. C12N 15/10 |
| | | 435/6.12 |
| 2007/0004041 A1 | 1/2007 | Church et al. |
| 2007/0122817 A1 | 5/2007 | Church et al. |
| 2007/0231805 A1 | 10/2007 | Baynes et al. |

(56) References Cited

U.S. PATENT DOCUMENTS

| | | |
|---|---|---|
| 2007/0269870 A1 | 11/2007 | Church et al. |
| 2007/0281309 A1 | 12/2007 | Kong et al. |
| 2008/0003571 A1 | 1/2008 | McKernan et al. |
| 2008/0009420 A1 | 1/2008 | Schroth et al. |
| 2008/0044862 A1 | 2/2008 | Schatz et al. |
| 2008/0064610 A1 | 3/2008 | Lipovsek et al. |
| 2008/0105829 A1 | 5/2008 | Faris et al. |
| 2008/0214408 A1 | 9/2008 | Chatterjee et al. |
| 2008/0261300 A1 | 10/2008 | Santi et al. |
| 2008/0274510 A1 | 11/2008 | Santi et al. |
| 2008/0274513 A1 | 11/2008 | Shenderov et al. |
| 2008/0287320 A1 | 11/2008 | Baynes et al. |
| 2008/0300842 A1 | 12/2008 | Govindarajan et al. |
| 2009/0016932 A1 | 1/2009 | Curcio et al. |
| 2009/0036323 A1 | 2/2009 | van Eijk et al. |
| 2009/0087840 A1 | 4/2009 | Baynes et al. |
| 2009/0093378 A1 | 4/2009 | Bignell et al. |
| 2009/0137408 A1 | 5/2009 | Jacobson |
| 2009/0155858 A1 | 6/2009 | Blake |
| 2009/0280497 A1 | 11/2009 | Woudenberg et al. |
| 2009/0280697 A1 | 11/2009 | Li et al. |
| 2009/0305233 A1 | 12/2009 | Borovkov et al. |
| 2010/0015614 A1 | 1/2010 | Beer et al. |
| 2010/0015668 A1 | 1/2010 | Staehler et al. |
| 2010/0016178 A1 | 1/2010 | Sussman et al. |
| 2010/0028873 A1 | 2/2010 | Belouchi et al. |
| 2010/0028885 A1 | 2/2010 | Balasubramanian et al. |
| 2010/0124767 A1 | 5/2010 | Oleinikov |
| 2010/0273219 A1 | 10/2010 | May et al. |
| 2010/0311058 A1 | 12/2010 | Kim et al. |
| 2011/0117625 A1 | 5/2011 | Lippow et al. |
| 2011/0160078 A1 | 6/2011 | Fodor et al. |
| 2011/0172127 A1 | 7/2011 | Jacobson et al. |
| 2011/0217738 A1 | 9/2011 | Jacobson |
| 2011/0283110 A1 | 11/2011 | Dapkus et al. |
| 2011/0287490 A1 | 11/2011 | Coope et al. |
| 2012/0028843 A1 | 2/2012 | Ramu et al. |
| 2012/0185965 A1 | 7/2012 | Senger et al. |
| 2012/0220497 A1 | 8/2012 | Jacobson et al. |
| 2012/0270750 A1 | 10/2012 | Oleinikov |
| 2012/0270754 A1 | 10/2012 | Blake |
| 2012/0283110 A1 | 11/2012 | Shendure et al. |
| 2012/0283140 A1 | 11/2012 | Chu |
| 2012/0315670 A1 | 12/2012 | Jacobson et al. |
| 2012/0322681 A1 | 12/2012 | Kung et al. |
| 2013/0005582 A1 | 1/2013 | Lower |
| 2013/0017977 A1 | 1/2013 | Oleinikov |
| 2013/0059296 A1 | 3/2013 | Jacobson et al. |
| 2013/0059344 A1 | 3/2013 | Striedner et al. |
| 2013/0059761 A1 | 3/2013 | Jacobson et al. |
| 2013/0085083 A1 | 4/2013 | Kamberov et al. |
| 2013/0130347 A1 | 5/2013 | Delisa et al. |
| 2013/0196373 A1 | 8/2013 | Gregory et al. |
| 2013/0224729 A1 | 8/2013 | Church et al. |
| 2013/0225421 A1 | 8/2013 | Li et al. |
| 2013/0244884 A1 | 9/2013 | Jacobson et al. |
| 2013/0252849 A1 | 9/2013 | Hudson et al. |
| 2013/0163263 A1 | 10/2013 | Jacobson et al. |
| 2013/0274135 A1 | 10/2013 | Zhang et al. |
| 2013/0281308 A1 | 10/2013 | Kung et al. |
| 2013/0296192 A1 | 11/2013 | Jacobson |
| 2013/0296194 A1 | 11/2013 | Jacobson |
| 2013/0309725 A1 | 11/2013 | Jacobson |
| 2014/0141982 A1 | 5/2014 | Jacobson et al. |
| 2014/0295556 A1 | 10/2014 | Joung et al. |
| 2014/0309119 A1 | 10/2014 | Jacobson et al. |
| 2015/0031089 A1 | 1/2015 | Lindstrom |
| 2015/0065393 A1 | 3/2015 | Jacobson |
| 2015/0191719 A1 | 7/2015 | Hudson et al. |
| 2015/0203839 A1 | 7/2015 | Jacobson et al. |
| 2015/0315547 A1 | 11/2015 | Oberg |
| 2015/0361420 A1 | 12/2015 | Hudson et al. |
| 2015/0368687 A1 | 12/2015 | Saaem et al. |
| 2015/0376602 A1 | 12/2015 | Jacobson et al. |
| 2016/0001247 A1 | 1/2016 | Oleinikov |
| 2016/0097051 A1 | 4/2016 | Jacobson et al. |
| 2016/0122755 A1 | 5/2016 | Hall et al. |
| 2016/0144332 A1 | 5/2016 | Chu |
| 2016/0144333 A1 | 5/2016 | Jacobson et al. |
| 2016/0168564 A1 | 6/2016 | Jacobson et al. |
| 2016/0215381 A1 | 7/2016 | Levine et al. |
| 2016/0250613 A1 | 9/2016 | Jacobson et al. |
| 2016/0326520 A1 | 11/2016 | Ramu et al. |
| 2017/0137858 A1 | 5/2017 | Carr et al. |
| 2017/0175110 A1 | 6/2017 | Jacobson et al. |
| 2017/0198268 A1 | 7/2017 | Jacobson et al. |
| 2017/0349925 A1 | 12/2017 | Jacobson et al. |

FOREIGN PATENT DOCUMENTS

| | | |
|---|---|---|
| CN | 101921840 | 12/2010 |
| DE | 4343591 | 6/1995 |
| EP | 259160 | 3/1988 |
| EP | 1015576 | 7/2000 |
| EP | 1159285 | 12/2001 |
| EP | 1205548 | 5/2002 |
| EP | 1314783 | 5/2003 |
| EP | 1411122 | 4/2004 |
| EP | 2017356 | 1/2009 |
| EP | 2175021 | 4/2010 |
| EP | 2638157 B1 | 7/2015 |
| JP | 2005-538725 A | 12/2005 |
| JP | 2007-533308 A | 11/2007 |
| KR | 100491810 B1 | 11/2005 |
| WO | WO 1990/000626 | 1/1990 |
| WO | WO 1992/015694 A1 | 9/1992 |
| WO | WO 1993/017126 | 9/1993 |
| WO | WO 1993/020092 | 10/1993 |
| WO | WO 1994/018226 | 8/1994 |
| WO | WO 1995/017413 | 6/1995 |
| WO | WO 1996/033207 | 10/1996 |
| WO | WO 1996/034112 | 10/1996 |
| WO | WO 1997/035957 | 10/1997 |
| WO | WO 1998/005765 | 2/1998 |
| WO | WO 1998/020020 | 5/1998 |
| WO | WO 1998/038299 | 9/1998 |
| WO | WO 1998/038326 | 9/1998 |
| WO | WO 1999/014318 | 3/1999 |
| WO | WO 1999/019341 | 4/1999 |
| WO | WO 1999/025724 | 5/1999 |
| WO | WO 1999/042813 | 8/1999 |
| WO | WO 1999/047536 | 9/1999 |
| WO | WO 2000/029616 | 5/2000 |
| WO | WO 2000/040715 | 7/2000 |
| WO | WO 2000/046386 | 8/2000 |
| WO | WO 2000/049142 | 8/2000 |
| WO | WO 2000/053617 A1 | 9/2000 |
| WO | WO 2000/075368 | 12/2000 |
| WO | WO 2001/081568 | 11/2001 |
| WO | WO 2001/085075 | 11/2001 |
| WO | WO 2001/088173 | 11/2001 |
| WO | WO 2002/004597 A2 | 1/2002 |
| WO | WO 2002/024597 | 3/2002 |
| WO | WO 2002/081490 A2 | 10/2002 |
| WO | WO 2002/095073 A1 | 11/2002 |
| WO | WO 2002/101004 A2 | 12/2002 |
| WO | WO 2003/010311 A2 | 2/2003 |
| WO | WO 2003/033718 | 4/2003 |
| WO | WO 2003/040410 | 5/2003 |
| WO | WO 2003/044193 | 5/2003 |
| WO | WO 2003/046223 | 6/2003 |
| WO | WO 2003/054232 | 7/2003 |
| WO | WO 2003/060084 | 7/2003 |
| WO | WO 2003/064611 | 7/2003 |
| WO | WO 2003/064026 | 8/2003 |
| WO | WO 2003/064027 | 8/2003 |
| WO | WO 2003/064699 | 8/2003 |
| WO | WO 2003/065038 | 8/2003 |
| WO | WO 2003/066212 | 8/2003 |
| WO | WO 2003/083604 A2 | 10/2003 |
| WO | WO 2003/085094 | 10/2003 |
| WO | WO 2003/089605 A2 | 10/2003 |
| WO | WO 2003/100012 | 12/2003 |
| WO | WO 2004/002627 A2 | 1/2004 |

(56) References Cited

FOREIGN PATENT DOCUMENTS

| | | |
|---|---|---|
| WO | WO 2004/024886 A2 | 3/2004 |
| WO | WO 2004/029586 | 4/2004 |
| WO | WO 2004/031351 | 4/2004 |
| WO | WO 2004/031399 | 4/2004 |
| WO | WO 2004/034028 A2 | 4/2004 |
| WO | WO 2004/090170 | 10/2004 |
| WO | WO 2005/059096 | 6/2005 |
| WO | WO 2005/071077 | 8/2005 |
| WO | WO 2005/089110 | 9/2005 |
| WO | WO 2005/103279 | 11/2005 |
| WO | WO 2005/107939 | 11/2005 |
| WO | WO 2005/123956 | 12/2005 |
| WO | WO 2006/031745 | 3/2006 |
| WO | WO 2006/044956 | 4/2006 |
| WO | WO 2006/049843 | 5/2006 |
| WO | WO 2006/076679 | 7/2006 |
| WO | WO 2006/086209 | 8/2006 |
| WO | WO 2006/127423 | 11/2006 |
| WO | WO 2007/008951 | 1/2007 |
| WO | WO 2007/009082 | 1/2007 |
| WO | WO 2007/010252 | 1/2007 |
| WO | WO 2007/075438 | 7/2007 |
| WO | WO 2007/087347 | 8/2007 |
| WO | WO 2007/113688 A2 | 10/2007 |
| WO | WO 2007/117396 | 10/2007 |
| WO | WO 2007/120624 | 10/2007 |
| WO | WO 2007/123742 | 11/2007 |
| WO | WO 2007/136736 | 11/2007 |
| WO | WO 2007/136833 A2 | 11/2007 |
| WO | WO 2007/136834 | 11/2007 |
| WO | WO 2007/136835 | 11/2007 |
| WO | WO 2007/136840 | 11/2007 |
| WO | WO 2008/024319 | 2/2008 |
| WO | WO 2008/027558 | 3/2008 |
| WO | WO 2008/041002 | 4/2008 |
| WO | WO 2008/045380 | 4/2008 |
| WO | WO 2008/054543 | 5/2008 |
| WO | WO 2008/076368 | 6/2008 |
| WO | WO 2008/109176 | 9/2008 |
| WO | WO 2008/130629 | 10/2008 |
| WO | WO 2010/025310 | 3/2010 |
| WO | WO 2010/025310 A2 | 3/2010 |
| WO | WO 2010/070295 | 6/2010 |
| WO | WO 2010/115100 | 10/2010 |
| WO | WO 2010/115154 A1 | 10/2010 |
| WO | WO 2011/056872 | 5/2011 |
| WO | WO 2011/066185 | 6/2011 |
| WO | WO 2011/066186 | 6/2011 |
| WO | WO 2011/085075 | 7/2011 |
| WO | WO 2011/143556 | 11/2011 |
| WO | WO 2011/150168 | 12/2011 |
| WO | WO 2011/161413 | 12/2011 |
| WO | WO 2012/064975 | 5/2012 |
| WO | WO 2012/078312 | 6/2012 |
| WO | WO 2012/084923 | 6/2012 |
| WO | WO 2012/174337 | 12/2012 |
| WO | WO 2013/032850 | 3/2013 |
| WO | WO 2013/163263 | 10/2013 |
| WO | WO 2014/004393 | 1/2014 |
| WO | WO 2014/089290 A1 | 6/2014 |
| WO | WO 2014/093694 | 6/2014 |
| WO | WO 2014/144288 A1 | 9/2014 |
| WO | WO 2014/151696 | 9/2014 |
| WO | WO 2014/160004 | 10/2014 |
| WO | WO 2014/160059 | 10/2014 |
| WO | WO 2014/191518 A1 | 12/2014 |
| WO | WO 2015/017527 | 2/2015 |
| WO | WO 2015/035162 A2 | 3/2015 |
| WO | WO 2015/081114 | 6/2015 |

OTHER PUBLICATIONS

Extended European Search Report dated Aug. 11, 2020, for Application No. EP 192030099.7.

International Search Report and Written Opinion in International Application No. PCT/US2011/060243 dated Sep. 7, 2012.
International Preliminary Report on Patentability in International Application No. PCT/US2011/060243 dated May 23, 2013.
Office Action for Chinese Application No. 201180064790.4 dated Jul. 17, 2014.
Non-Final Office Action in U.S. Appl. No. 13/884,463 dated Apr. 21, 2015.
Final Office Action in U.S. Appl. No. 13/884,463 dated Sep. 28, 2015.
[No Author Listed], TnT® coupled reticulocyte lysate system, Technical Bulletin (Promega, Madison, Wis), 2013.
Abremski et al. Studies on the properties of P 1 site-specific recombination: evidence for topologically unlinked products following recombination. Cell 32:1301-1311 (1983).
Abremski K. et al. Bacteriophage P1 site-specific recombination. Purification and properties of the Cre recombinase protein (1984) J. Mol. Biol. 259: 1509-1514.
Adessi et al., Solid phase DNA amplification: characterisation of primer attachment and amplification mechanisms, Nucleic Acids Research, 28(20):E87, (Oct. 15, 2000).
Afshari et al. Application of Complementary DNA Microarray Technology to Carcinogen Identification, Toxicology, and Drug Safety. Cancer Research, 59, 4759-4760, Oct. 1, 1999.
Aihara, H. et al. A Conformational Switch Controls the DNA Cleavage Activity of .lamda. Integrase, Molecular Cell, 12:187-198, (Jul. 2003).
Akhundova A.A. et al. RNA synthesis on immobilized DNA templates in vitro. Biochemistry—Moscow, 43(5):626-628 (1978).
Altschul et al., Iterated profile searches with PSI-BLAST—a tool for discovery in protein databases, Trends Biochem. Sci., 23:444-447, (Nov. 1998).
Altschul, S., et al. Basic local alignment search tool, J Mol Biol., 215(3):403-10, (1990).
Andersen, J., et al. New Unstable Variants of Green Fluorescent Protein for Studies of Transient Gene Expression in Bacteria, Applied and Environmental Microbiology, 64(6):2240-2246 (Jun. 1998).
Ashkin, A., Applications of laser radiation pressure Science, 210(4474): 1081-1088, (Dec. 5, 1980).
Aslanzadeh, Brief Review: Preventing PCR Amplification Carryover Contamination in a Clinical Laboratory. Annals of Clinical & Laboratory Science 34(4) :389 (2004).
Au, L., et al. Gene Synthesis by a LCR-Based Approach: High Level Production of Leptin-L54 Using Synthetic Gene in *Escherichia coli*, Biochemical and Biophysical Research Communications, 248:200-203 (1998).
Babineau et al. The FLP Protein of the 2 micron Plasmid of Yeast (1985) J. Biol. Chem. 260: 12313-12319.
Bar G., et al., Dendrimer-modified silicon oxide surfaces as platforms for the deposition of gold and silver colloid monolayers: preparation method, characterization, and correlation between microstructure and optical properties, Langmuir, 12(5): 1172-1179, (Mar. 6, 1996).
Bartsevich, V., et al. Engineered Zinc Finger Proteins for Controlling Stem Cell Fate, Stem Cells, 21:632-637 (2003).
Beer, N., et al., On-chip, real time single-copy polymerase chain reaction in picoliter droplets, Analytical Chemistry, 79(22):8471-8475, (Nov. 15, 2007).
Beier et al., Analysis of DNA-microarray produced by inverse in situ oligonucleotide synthesis. J. Biotechnology, 94:15-22 (2002).
Bennett, S., Solexa Ltd., Pharmacogenomics, 5(4):433-8, (Jun. 2004).
Berlin Y. A. DNA splicing by directed ligation (SDL), Current Issues Molec. Biol. 1:21-30, 1999.
Bethell, D., et al. From monolayers to nanostructured materials: an organic chemist's view of self-assembly, J. Electroanal. Chem., 409:137-143, (1996).
Binkowski B. F. et al. Correcting errors in synthetic DNA through consensus shuffling Nucl. Acids Res., vol. 33, No. 6, e55, 2005.
Blanchard, A., "Synthetic DNA Arrays," Genetic Engineering, 20:111-123, Plenum Press, (1998).

(56) References Cited

OTHER PUBLICATIONS

Boal, J., et al. Cleavage of oligodeoxyribonucleotides from controlled-pore glass supports and their rapid deprotection by gaseous amines, NAR, 24(15):3115-3117, (1996).
Boltner, D., et al. R391: A Conjugative Integrating Mosaic Comprised of Phage, Plasmid, and Transposon Elements, J. of Bacteriology, 184(18):5158-5169 (Sep. 2002).
Booth, P., et al. Assembly and cloning of coding sequences for neurotrophic factors directly from genomic DNA using polymerase chain reaction and uracil DNA glycosylase, Gene, 146(2):303-308 (1994).
Braatsch et al., *Escherichia coli* strains with promoter libraries constructed by Red/ET recombination pave the way for transcriptional fine-tuning, Biotechniques. 45(3): 335-337 (2008.
Brown, C. BioBricks to help reverse-engineer life, URL: http://eetimes.com/news/latest/showArticle.ihtml?articleID=21700333, (Jun. 11, 2004).
Burge et al., Prediction of complete gene structures in human genomic DNA, J Mol Biol., 268(1):78-94, (1997).
Cai, Q., et al. Immunogenicity of Polyepitope Libraries Assembled by Epitope Shuffling: An Approach to the Development of Chimeric Gene Vaccination Against Malaria, Vaccine, 23:267-277, (2004).
Carr, P., et al. Protein-mediated error-correction for de novo DNA synthesis, Nucleic Acids Research, 32(20), e162 (9 pages), (2004).
Caruthers, et al. CXV. Total synthesis of the structural gene for an alanine transfer RNA from yeast. Enzymic joining to form the total DNA duplex, J Mol Biol., 72(2):475-92, (Dec. 28, 1972).
Cassell et al., Mechanism of Inhibition of Site-specific Recombination by the Holliday Junction-trapping Peptide WKHYNY: Insights into Phage I integrase-mediated Strand Exchange, J. Mol. Biol., 327:413-429, (2003).
Chakrabarti et al., Novel Sulfoxides facilitate GC-rich template amplification., 2002, BioTechniques 32(4):866-873.
Chalmers et al., Scaling up the ligase chain reaction-based approach to gene synthesis, BioTechniques, 30(2):249-252, (Feb. 2001).
Chan, L. et al. Refactoring bacteriophage T7, Molecular Systems Biol., doi: 10.1038/msb4100025, (Published online Sep. 13, 2005).
Chandrasegaran, S., et al. Chimeric Restriction Enzymes: What is Next?, Biol. Chem., 380:841-848 (1999).
Chang, C., et al. Evolution of a cytokine using DNA family shuffling, Nature Biotechnology, 17: 793-797(1999).
Che, A. BioBricks++: Simplifying Assembly of Standard DNA Components, [Online] XP002412778, URL: http://austinche.name/docs/bbpp.pdf, (Jun. 9, 2004).
Chen, H., et al. A new method for the synthesis of a structural gene, Nucleic Acids Research, 18(4):871-878 (Feb. 1990).
Cherepanov, A., et al. Joining of short DNA oligonucleotides with base pair mismatches by T4 DNA ligase, J Biochem., 129(1):61-68, (Jan. 2001).
Chetverin et al., Sequencing pool of Nucleic Acids on Oligonucleotide arrays, Biosystems, 30:215-231, (1993).
Chevalier et al., Homing endonucleases: structural and functional insight into the catalysts of intron/intein mobility, Nucl. Acids Res., 29(18):3757-3774 (2001).
Chevalier, B., et al. Design, Activity, and Structure of a Highly Specific Artificial Endonuclease, Molecular Cell, 10:895-905 (Oct. 2002).
Cho, S., et al. Creating, transporting, cutting and merging liquid droplets by electrowetting-based actuation for digital microfluidic circuits, J. of Microelectromechanical Systems, 12(1):70-80, (Feb. 2003).
Christians, F., et al. Directed evolution of thymidine kinase for AZT phosphorylation using DNA family shuffling, Nature Biotechnology, 17:259-264(1999).
Coco, W., et al. Growth Factor Engineering by Degenerate Homoduplex Gene Family Recombination, Nature Biotechnology, 20:1246-1250, (Dec. 2002).
Colvin, V., et al. Semiconductor nanocrystals covalently bound to metal surfaces with self-assembled monolayers, J. Am. Chem. Soc., 114(13):5221-5230, 1992.

Crameri, A, et al. DNA shuffling of a family of genes from diverse species accelerates directed evolution, Nature, 391:288-291(1998).
Crameri, A, et al. Molecular evolution of an arsenate detoxification pathway by DNA shuffling, Nature Biotechnology, 15:436-438 (1997).
Crameri, A., et al. Improved Green Fluorescent Protein by Molecular Evolution Using DNA Shuffling, Nature Biotechnology, 14:315-319, (Mar. 1996).
Cui T. et al. Sepharose-supported DNA as template for RNA synthesis J. Biotechnology, 66: 225-228 (1998).
Dafhnis-Calas, F., et al. Iterative in vivo assembly of large and complex transgenes by combining the activities of <DC31 integrase and Cre recombinase, Nucleic Acids Research, 33(22): 1-14 (2005).
Datsenko K.A. et al. One-step inactivation of chromosomal genes in *Escherichia coli* K-12 using PCR products PNAS (2000) 97: 6640-6645.
Dedkova, L. et al. Enhanced D-Amino Acid Incorporation into Protein by modified Ribosomes, J. Am. Chem. Soc., 125:6616-6617, (2003).
Demeler et al. Neural network optimization for *E.coli* promoter prediction, Nucl. Acids. Res. 19:1593-1599 (1991).
Dillon, P.J. et al., A Rapid Method for the Construction of Synthetic Genes Using the Polymerase Chain Reaction, Biotechniques, vol. 9, No. 3, pp. 298-300, 1990.
Doyon et al., Enhancing zinc-finger-nuclease activity with improved obligate heterodimeric architectures. Nat Methods. Jan. 2011;8(1):74-9. doi:10.1038/nmeth.1539. Epub Dec. 5, 2010.
Duggan, D., et al., "Expression profiling using cDNA microarrays," Nat. Genet. 21:10-14, (Jan. 1999).
Ellson, Picoliter: Enabling Precise Transfer of Nanoliter and Picoliter Volumes. Drug Discovery Today 7(5 Suppl.) :s32 (2002).
Elowitz et al., A synthetic oscillatory network of transcriptional regulators. Nature. 2000;403;335-338.
Engler C. et al. A one pot, one step, precision cloning method with high throughput capability PLoS One, 3: e36471.
Engler C. et al. Golden Gate Shuffling: a one-pot DNA shuffling method based on type IIS restriction enzymes PLoS One, 4:e5553, 2009.
Evans et al., Roles for Mismatch Repair Factors in Regulating Genetic Recombination, Molecular & Cellular Biology, 20(21):7839-7844 (Nov. 2000).
Ferretti, L. et al. Total synthesis of a gene for bovine rhodopsin, PNAS, 83:599-603 (Feb. 1986).
Ferrin, L.J., et al. Sequence-specific ligation of DNA using RecA protein, Proc. Natl. Acad. Sci. USA, 95: 2152-2157 (1998).
Fidalgo et al., Surface induced droplet fusion in microfluidic devices, Lab on Chip, 7(8)984-986, (2007).
Fisch, I. et al. A Strategy of Exon Shuffling for Making Large Peptide Repertoires Displayed on Filamentous Bacteriophage, Proceedings of the National Academy of Sciences of USA, 93:7761-7766, (Jul. 1996).
Flanagan et al. Analysis of inhibitors of the site-specific recombination reaction mediated by Tn3 resolvase (1989) J. Mol. Biol. 206: 295-304.
Fleck et al., DNA Repair, J. Cell Science, 117(4):515-517 (2004).
Fodor, S., et al., "Light-directed, spatially addressable parallel chemical synthesis," Science, 251(4995):767-773, (Feb. 15, 1991).
Fujita et al., Surprising liability of biotin-streptavidin bond during transcription of biotinylated DNA bound to paramagnetic streptavidin beads. Bio Techniques, 14:608-617 (1993).
Fullwood et al., Next-generation DNA sequencing of paired-end tags (PET) for transcriptome and genome analyses. Genome Res. Apr. 2009;19(4):521-32. doi: 10.1101/gr.074906.107.
Gabsalilow et al., Site- and strand-specific nicking of DNA by fusion proteins derived from MutH and I-SceI or TALE repeats. Nucleic Acids Res. Apr. 2013;41(7):e83. doi: 10.1093/nar/gkt080. Epub Feb. 13, 2013.
Gao, X. et al. Thermodynamically balanced inside-out (TBIO) PCR-based gene synthesis: a novel method of primer design for high fidelity assembly of longer gene sequences, Nucleic Acids Research, 31(22):e143 (11 pages) (2003).
Gardner, T., et al. Construction of a genetic toggle switch in *Escherichia coli*, Nature, 403(20):339-342 (Jan. 2000).

(56) References Cited

OTHER PUBLICATIONS

Gibbs, W. Synthetic Life, Scientific American, [Online] URL: http://www.sciam.com/orintversion.cfm?articleID=0009FCA4, (Apr. 26, 2004).
Glasgow A.C. et al. DNA-binding properties of the Hin recombinase (1989) J. Biol. Chem. 264: 10072-10082.
Goler, J. BioJADE: A Design and Simulation Tool for Synthetic Biological Systems, MIT Computer Science and Artificial Intelligence Laboratory, AI Technical Report, [Online] URL:http://dspace.mit.edu/bitstream/1721.1/30475/2/MIT-CSAIL-TR-2004-036.pdf, (May 2004).
Grabar et al., Preparation and Characterization Monolayers, Anal. Chem., 67:735-743, (1995).
Greenberg et al., Cleavage of oligonucleotides from solid-phase support using o-nitrobenzyl photochemistry, J. of Org. Chem., 59(4):746-753, (Feb. 1994).
Griffith et al., Coordinating Multiple Droplets in Planar Array Digital Microfluidic Systems, The International Journal of Robotics Research, 24(11):933-949, (Nov. 2005).
Gronostajski et al., The FLP protein of the 2 micron plasmid of yeast (1985) J. Biol. Chem. 260: 12328-12335.
Guilinger et al., Fusion of catalytically inactive Cas9 to FokI nuclease improves the specificity of genome modification. Nat Biotechnol. Jun. 2014;32(6):577-582. doi: 10.1038/nbt.2909. Epub Apr. 25, 2014.
Gulati S. et al. Opportunities for microfluidic technologies in synthetic biology. Journal of the Royal Society, vol. 6, Suppl. 4, pp. S493-S506, (2009).
Guntas, G., et al. A molecular switch created by in vitro recombination of nonhomologous genes, Chem. & Biol., 11:1483-1487 (Nov. 2004).
Guntas, G., et al. Directed Evolution of Protein Switches and Their Application to the Creation of Ligand-Binding Proteins, Proc. Natl. Acad. Sci. USA, 102(32):11224-11229 (Aug. 9, 2005).
Gupta, N., et al. Studies on Polynucleotides, LXXXVIII. Enzymatic Joining of Chemically Synthesized Segments Corresponding to the Gene for Alanine-tRNA, PNAS, 60:1338-1344, (1968).
Hacia J.G. et al. Applications of DNA chips for genomic analysis. Mol Psychiatry. Nov. 1998;3(6):483-92.
Hacia J.G. Resequencing and mutational analysis using oligonucleotide microarrays, Nature Genetics, 21(1 suppl):42-47, 1999.
Haeberle et al., Microfluidic platforms for lab-on-chip applications, Lab on a Chip 7(9):1094-1110, (2007).
Haffter et al. Enhancer independent mutants of the Cin recombinase have a relaxed topological specificity. (1988) EMBO J. 7:3991-3996.
Hansen et al., Review of Mammalian DNA Repair and Transcriptional Implications, J. Pharmacol. & Exper. Therapeutics, 295(1):1-9, (2000).
Hardy, P., et al., Reagents for the preparation of two oligonucleotides per synthesis (TOPSTM), Nucleic Acids Research, 22(15):2998-3004, (1994).
Hawley et al., Compilation and analysis of *Escherichia coli* promoter DNA sequences Nucl. Acid. Res. 11:2237-2255. 1983.
Hayden et al., Gene synthesis by serial cloning of oligonucleotides. DNA. Oct. 1988;7(8):571-7.
Hecker, K. Error Analysis of Chemically Synthesized Polynucleotides, BioTechniques, 24(2):256-260, (Feb. 1998).
Heeb, S., et al. Small, Stable Shuttle Vectors Based on the Minimal pVS1 Replicon for Use in Gram-Negative Plant-Associated Bacteria, MPMI, 13(2):232-237 (2000).
Henegariu et al. Multiplex PCR: critical parameters and step-by-step protocol Biotechniques, 23(3): 504-511, (Sep. 1997).
Hermeling, S., et al. Structure-Immunogenicity Relationships of Therapeutic Proteins, Pharmaceutical Research, 21(6):897-903, (Jun. 2004).
Higuchi, R., et al. A general method of in vitro preparation and specific mutagenesis of DNA fragments: study of protein and DNA interactions, Nucleic Acids Research, 16(15):7351-7367 (1988).

Hoess et al., Mechanism of strand cleavage and exchange in the Cre-lox site-specific recombination system (1985) J. Mol. Biol. 181: 351-362.
Hoess R.H. et al. Interaction of the bacteriophage P 1 recombinase Cre with the recombining site loxP (1984) Proc. Natl. Acad. Sci. USA 81: 1026-1029.
Hoess R.H. et al. P 1 site-specific recombination: nucleotide sequence of the recombining sites (1982) Proc. Natl. Acad. Sci. USA 79: 3398-3402.
Hoess R.H. et al. The role of the loxP spacer region in PI site-specific recombination (1986), Nucleic Acids Res. 14: 2287-2300.
Holmes, C., Model studies for new o-nitrobenzyl photolabile linkers: substituent effects on the rates of photochemical cleavage, J. of Org. Chem., 62(8):2370-2380, (Apr. 18, 1997).
Hoover et al., DNAWorks: an automated method for designing oligonucleotides for PCR-based gene synthesis, Nucleic Acids Research, 30(10):e43 (7 pages), (2002).
Horton, R., et al. Engineering hybrid genes without the use of restriction enzymes: Gene splicing by overlap extension, Gene, 77:61-68, (1989).
Hyman, E., a new method of sequencing DNA, Analytical Biochemistry, 174(2):423-436, (Nov. 1, 1988).
Ibrahim, E., et al. Serine/arginine-rich protein-dependent suppression of exon skipping by exonic splicing enhancers, Proc. Natl. Acad. Sci. U S A, 102(14):5002-5007, (Apr. 5, 2005).
Ito R. et al. Novel muteins of human tumor necrosis factor alpha Biochimica et Biophysica Acta, 1096 (3): 245-252 (1991).
Jayaraman et al. Polymerase chain-reaction mediated gene synthesis: synthesis of a gene coding for Isozyme C of Horseradish Peroxidase PNAS 88:4084-4088, (May 1991).
Jayaraman, et al. A PCR-mediated Gene synthesis strategy involving the assembly of oligonucleotides representing only one of the strands, Biotechniques, 12(3):392-398, (1992).
Jensen P.R. et al. The sequence of spacers between the consensus sequences modulates the strength of prokaryotic promoters Appl. Env. Microbiol. 64:82-87, 1998.
Johnston M. Gene chips: Array of hope for understanding gene regulation. Current Biology, 8: (5) R171, 1998.
Jones, T.D., et al. The Development of a Modified Human IFN-alpha2b Linked to the Fc Portion of Human IgG1 as a Novel Potential Therapeutic for the Treatment of Hepatitis C Virus Infection, Journal of Interferon & Cytokine Research, 24:560-572,(2004).
Kahl, J., et al. Solution-Phase Bioconjugate Synthesis Using Protected Oligonucleotides Containing 3'-Alkyl Carboxylic Acids, J. of Org. Chem., 64(2):507-510, (1999).
Kahl, J., et al., High-Yielding Method for On-Column Derivatization of Protected Oligodeoxy-nucleotides and Its Application to the Convergent Synthesis of 5',3'-Bis-conjugates, J. of Org. Chem., 63(15):4870-4871.
Kampke et al., Efficient primer design algorithms. Bioinformatics, 2001;17(3):214-225.
Kelly, B., et al., Miniaturizing chemistry and biology in microdroplets, Chem. Commun., 1773-1788, (2007).
Khaitovich, P., et al. Characterization of functionally active subribosomal particles from Thermus aquaticus, Proc. Natl. Acad. Sci., 96:85-90 (Jan. 1999).
Kim et al., Precision genome engineering with programmable DNA-nicking enzymes. Genome Res. Jul. 2012;22(7):1327-33. doi:10.1101/gr.138792.112. Epub Apr. 20, 2012.
Kim J.H. et al. Solid-phase genetic engineering with DNA immobilized on a gold surface. J. Biotechnology, 96:213-221. (2002).
Kim, C., et al. Biological lithography: Improvements in DNA synthesis methods, J. Vac. Sci. Technol. B 22(6):3163-3167 (2004).
Kim, Y., et al. Insertion and Deletion Mutants of FokI Restriction Endonuclease, J. Biol. Chem., 269(50):31978-31982 (1994).
Kinde et al., Detection and quantification of rare mutations with massively parallel sequencing. Proc Natl Acad Sci U S A. Jun. 7, 2011;108(23):9530-5. doi: 10.1073/pnas.1105422108. Epub May 17, 2011. Supplemental Information.
Kisselev, L., et al. Termination of translation: interplay of mRNA, rRNAS and release factors?, The EMBO J., 22(2):175-182, (2003).

(56) References Cited

OTHER PUBLICATIONS

Kitamura, Koichiro et al. Construction of Block-Shuffled Libraries of DNA for Evolutionary Protein Engineering: Y-Ligation-Based Block Shuffling. Protein Engineering, 15(10): 843-853, (Oct. 2002).
Kleppe K., et al. Studies of polynucleotides: repair replication of short synthetic DNA's as catalyzed by DNA polymerases, J. Mol. Biol. 56:341-361, (1971).
Kodumal., S., et al. Total synthesis of long DNA sequences: Synthesis of a contiguous 32-kb polyketide synthase gene cluster, PNAS, 101(44):15573-15578, (Nov. 2, 2004).
Kolisnychenko, V., et al. Engineering a Reduced *Escherichia coli* Genome, Genome Research, 12:640-647, (2002).
Kong, D., et al., Parallel gene synthesis in microfluidic device, Nucleic Acids Research, vol. 35, No. 8, pp. e61-1 (9 pages), (2007).
Kosuri et al. (Scalable gene synthesis by selective amplification of DNA pools from high-fidelity microchips, Nature Biotechnology 28, 1295-1299 (2010), Published online Nov. 28, 2010).
Kotsopoulou, E., et al. A Rev-Independent Human Immunodeficiency Virus Type 1 (HIV-1)-Based Vector That Exploits a Codon-Optimized HIV-1 gag-pol Gene, Journal of Virology, 74(10):4839-4852, (May 2000).
Kowalczykowski, S. In vitro reconstitution of homologous recombination reactions, Experientia, 50:204-215, (1994).
Kowalczykowski, S. Initiation of genetic recombination and recombination-dependent replication, TIBS, 25:156-165, (Apr. 2000).
Krieg et al., Real-time detection of nucleotide incorporation during complementary DNA strand analysis Chem. Bio. Chem. 4:589-592 (2003).
Kurian et al. DNA chip technology. J Pathol.; 187(3):267-71, (Feb. 1999).
Lamers, M., et al. ATP Increases the Affinity between MutS ATPase Domains, J. Biol. Chem., 279(42):43879-43885, (Oct. 15, 2004).
Lashkari et al. An automated multiplex oligonucleotide synthesizer: Development of high throughput, low cost DNA synthesis. PNAS 92(17): 7912-7915, (1995).
Leamon, J., et al., A massively parallel PicoTiterPlate.TM.based platform for discrete picoliter-scale polymerase chain reactions, Electrophoresis, 24(21):3769-3777, (Nov. 2003).
Lebedenko E.N. et al. Method of artificial DNA splicing by directed ligation Nucleic Acids Research, 19: 6757-6761, 1991.
Lederman et al., DNA-directed peptide synthesis I. A comparison of T2 and *Escherichia coli* DNA-Directed Peptide Synthesis in Two Cell-Free Systems, Biochim, Biophys. Acta, vol. 149, pp. 235-258, (1967).
Lee, K., et al. Genetic approaches to Studying Protein Synthesis: Effects of Mutations at .psi.1516 and A535 in *Escherichia coli* 16S rRNA, J. Nutr., 131:2994S-3004S, (2001).
Leslie et al., Site-specific recombination in the replication terminus region of *Escherichia coli*: functional replacement of dif. (1995) EMBO J. 14: 1561-1570.
Lewis et al. Gene modification via plug and socket gene targeting. J Clin Invest. Jan. 1, 1996;97(1):3-5.
Lewis et al., Control of directionality in integrase-mediated recombination: examination of recombination directionality factors (RDFs) including Xis and Cox proteins, Nucl. Acids Res., 29(11):2205-2216 (2001).
Li et al., Alteration of the cleavage distance of Fok I restriction endonuclease by insertion mutagenesis. Proc Natl Acad Sci U S A, 90:2764-2768, (Apr. 1993).
Li et al., Ligation independent cloning irrespective of restriction site compatibility, Nucl. Acids Res., 25(20):4165-4166, (1997).
Link, A., et al. Methods for generating precise deletions and insertions in the genome of wild-type *Escherichia coli*: Application to open reading frame characterization, J. Bacteriol., 179(20):6228-6237, (Oct. 1997).
Liu et al., DNA nanomachines and their functional evolution. Chem Commun (Camb). May 21, 2009;(19):2625-36. doi: 10.1039/b822719e. Epub Apr. 6, 2009.
Liu G. et al. DNA computing on surfaces. Nature, 403: 175-179 (2000).
Liu, W. et al. Genetic Incorporation of Unnatural Amino Acids Into Proteins in Mammalian Cells, Nature Methods, 4(3):239-244, (Mar. 2007).
Liu, Y., et al., DNA ligation of ultramicrovolume using EWOD microfluidic system with coplanar electrodes: DNA ligation of ultramicrovolume using a EWOD microfluidic system, J. of Micromechanics and Microengineering, 18(4):45017 (7 pages), (2008).
Lu et al., Conjugative transposition: Tn916 integrase contains two independent DNA binding domains that recognize different DNA sequences '(1994) EMBO J. 13: 1541-1548.
Luo, P., et al. Development of a Cytokine Analog with Enhanced Stability Using Computational Ultrahigh Throughput Screening, Protein Science, 11:1218-1226, (2002).
Lutz, S., et al. Homology-Independent Protein Engineering, Current Opinion in Biotechnology, 11(4):319-324, (Aug. 2000).
Mandecki et al. FokI method of gene synthesis Gene, 68:101-107 (1988).
Mandecki W. Oligonucleotide-directed double-strand break repair in plasmids of *Escherichia coli*: A method for site-specific mutagenesis. 1986, PNAS, 83 :7177-7181.
Mannervik, B. Optimizing the Heterologous Expression of Glutathione Transferase, Methods in Enzymology, 401:254-265, (2005).
Margulies et al., Genome Sequencing in Microfabricated High-Density Picolitre Reactors, Nature. 437: 376-380 (2005). Supplemental materials.
Matzas et al. (High-fidelity gene synthesis by retrieval of sequence-verified DNA identified using high-throughput pyrosequencing, Nature Biotechnology 28, 1291-1294 (2010), Published online Nov. 28, 2010).
McCaughan et al., Single-Molecule Genomics, The Journal of Pathology, 220: 297-306, (Jan. 1, 2009).
McClain et al., Genome Sequence Analysis of Helicobacter Pylori Strains Associated with Gastric Ulceration and Gastric Cancer, BMC Genomics, Biomed Central Ltd, London, IK. 10(1):3 (2009).
McGall, G., et al., "Light-directed synthesis of high-density oligonucleotide arrays using semiconductor photoresists," Proc. Natl. Acad. Sci. U.S.A, 93:13555-13560, (Nov. 1996).
Mei et al., Cell-Free Protein Synthesis in Microfluidic Array Devices, Biotechnol. Prog. 2007, 23:1305-1311.
Mercier. J. et al. Structural and functional characterization of tnpI, a recombinase locus in Tn21 and related beta-lactamase transposons. (1990) J. Bacteriol. 172: 3745.
Metzker, Emerging technologies in DNA sequencing. Genome Res. Dec. 2005;15(12):1767-76.
Metzker, M., et al., Termination of DNA synthesis by novel 3'-modified-deoxyribonucleoside 5'-triphosphates, NAR, 22(20):4259-4267, (1994).
Meyer-Leon et al. Purification of the FLP site-specific recombinase by affinity chromatography and reexamination of basic properties of the system (1987) Nucleic Acids Res. 15: 6469.
Mezard, C., et al. Recombination Between Similar But Not Identical DNA Sequences During Yeast Transformation Occurs Within Short Stretches of Identity, Cell, 70:659-670, (Aug. 21, 1992).
Miick, S., et al. Crossover isomer bias is the primary sequence-dependent property of immobilized Holliday junctions, Proc. Natl. Acad. Sci. USA, 94:9080-9084, (Aug. 1997).
Milton, R., et al. Total Chemical Synthesis of a D-Enzyme: The Enantiomers of HIV-1 Protease Show Demonstration of Reciprocal Chiral Substrate Specificity, Science, 256:1445-1448, (Jun. 5, 1992).
Mir K. U. et al. Sequencing by cyclic ligation and cleavage (CycLic) directly on a microarray captured template. Nucl. Acids Rse. vol. 37, No. 1 e5, 2008.
Mitra et al., Fluorescent in situ Sequencing on Polymerase Colonies, Analytical Biochemistry. 320:55-65 (2003).
Modrich, P. Strand-specific Mismatch Repair in Mammalian Cells, J. Biol. Chem., 272(40): 24727-24730, (Oct. 3, 1997).
Moffitt et. al. Recent Advances in Optical Tweezers. Annual Review of Biochemistry 77 :205 (Feb. 2008).
Moore et al., Computational Challenges in Combinatorial Library Design for Protein Engineering, AIChE Journal, 50(2):262-272, (Feb. 2004).
Morton, Life, Reinvented. Wired. 2009. Retrieved from http://archive.wired.com/wired/archive/13.01/mit_pr.html on Aug. 14, 2015.

(56) References Cited

OTHER PUBLICATIONS

Muller, Ten years of gene targeting: targeted mouse mutants, from vector design to phenotype analysis. Mech Dev. Apr. 1999;82(1-2):3-21.
Nakamaye, K., et al. Direct sequencing of polymerase chain reaction amplified DNA fragments through the incorporation of deoxynucleoside-thiotriphosphates, Nucleic Acids Research, 16(21):9947-9959, (1988).
Nakamura et al., How protein reads the stop codon and terminates translation, Genes to Cells, 3:265-278, (1998).
Nakayama et al., A system using convertible vectors for screening soluble recombinant proteins produced in *Escherichia coli* from randomly fragmented cDNAs, Bioch. and Biophys. Res. Comm., 312:825-830, (2003).
Ness, J., et al. DNA shuffling of subgenomic sequences of subtilisin, Nature Biotechnology 17: 893-896 (1999). Abstract only.
Ness, J., et al. Synthetic Shuffling Expands Functional Protein Diversity by Allowing Amino Acids to Recombine Independently Nature Biotechnology, 20:1251-1255, (Dec. 2002).
Neuman et al., Optical trapping. Rev Sci Instrum. Sep. 2004;75(9):2787-809.
Nilsson P., et al. Real-Time monitoring of DNA manipulations using biosensor technology, Analytical Biochemistry, 224:400-408, (1995).
Nilsson, L., et al. Improved Heterologous Expression of Human Glutathione Transferase A4-4 by Random Silent Mutagenesis of Codons in the 5' Region, Biochemica et Biophysica Acta, 1528: 101-106, (2001).
Noirot et al., DNA Strand Invasion Promoted by *Esherichia coli* RecT Protein, J. Biol. Chem., 273(20):12274-12280, (May 15, 1998).
Novy, R., et al. Ligation Independent Cloning: Efficient Directional Cloning of PCR Products, Novagen, Inc., InNovations, 5:1-3, http://www.emdbiosciences.com/html/NVG/inNovations.html), (1996).
Orban P.C. et al. Tissue- and site-specific DNA recombination in transgenic mice (1992) Proc. Natl. Acad. Sci. 89: 6861-6865.
Osawa, S., et al. Recent Evidence for Evolution of the Genetic Code, Microbiological Reviews, 56(1):229-264, (Mar. 1992).
Osborn et al., When phage, plasmids, and transposons collide: genomic islands, and conjugative and mobilizable-transposons as a mosaic continuum, Plasmid, 48:202-212, (2002).
Pachuk C.J. et al. Chain reaction cloning: one step method for directional ligation of multiple DNA fragments Gene, 243(1-2):19-25 (2000).
Padgett et al .. Creating seamless junctions independent of restriction sites in PCR cloning, Gene, Feb. 2, 1996, vol. 168, No. 1, pp. 31-35.
Pan et al., An approach for global scanning of single nucleotide variations, PNAS, 99(14):9346-9351, (Jul. 9, 2002).
Panet et al., Studies of polynucleotides: the linkage of deoxyribopolynucleotides templates to cellulose and its use in their replication. J. Biol. Chem. 249(16):5213-5221 (1974).
Parr et al., New donor vector for generation of histidine-tagged fusion proteins using the Gateway Cloning System, Plasmid, 49:179-183, (2003).
Pemov et al., DNA analysis with multiplex microarray-enhanced PCR. Nucleic Acids Res. Jan. 20, 2005;33(2):e11.
Peters et al., Tn7: Smarter Than We Thought, Nature, 2:806-814, (Nov. 2001).
Petrik et al., Advances in Transfusion Medicine in the First Decade of the 21.sup.st Century: Advances in Miniaturized Technologies, Transfusion and Apheresis Science. 45(1): 45-51 (2011).
Pon., R. Solid-phase supports for oligonucleotide synthesis, Methods Mol. Biol., 20:465-496, (1993).
Posfai, G., et al. In vivo excision and amplification of large segments of the *Escherichia coli* genome, Nucl. Acids Res., 22(12):2392-2398, (1994).
Posfai, G., et al. Markerless gene replacement in *Escherichia coli* stimulated by a double-strand break in the chromosome, Nucl. Acids Res., 27(22):4409-4415, (1999).
Prodromou et al., Recursive PCR: A Novel Technique for Total Gene Synthesis Protein Engineering, 5(8):827-829 (1992).
Ramachandran et al., End-Point Limiting-Dilution Real-Time PCR Assay for Evaluation of Hepatitis C Virus Quasispecies in Serum: Performance Under Optimal and Suboptimal Conditions, Journal of Virological Methods. 151(2): 217-224 (2008).
Ramirez et al., Engineered zinc finger nickases induce homology-directed repair with reduced mutagenic effects. Nucleic Acids Res. Jul. 2012;40(12):5560-8. doi: 10.1093/nar/gks179. Epub Feb. 28, 2012.
Randegger et al., Real-time PCR and melting curve analysis for reliable and rapid detection of SHV extended-spectrum beta-lactamases. Antimicrob Agents Chemother. Jun. 2001;45(6):1730-6.
Regalado, A. Next Dream for Venter: Create Entire Set of Genes From Scratch, Wall Street Journal, A1, (Jun. 29, 2005).
Reyrat, J., et al. Counterselectable Markers: Untapped Tools for Bacterial Genetics and Pathogenesis, Infection and Immunity, 66(9):4011-4017, (Sep. 1998).
Richmond, K., et al., Amplification and assembly of chip-eluted DNA (AACED): a method for high-throughput gene synthesis, Nucleic Acids Research, 32(17): 5011-5018 (2004).
Roberts et al., RNA-peptide fusions for the in vitro selection of peptides and proteins, Proc Natl Acad Sci USA. 94(23): 12297-302, 1997.
Rouillard, J. et al. Gen2Oligo: Oligonucleotide design for in vitro gene synthesis, Nucleic Acids Research, 32: W176-W180, (2004).
Rouwendal, G., et al. Enhanced Expression in Tobacco of the Gene Encoding Green Fluorescent Protein by Modification of its Codon Usage, Plant Molecular Biology, 33:989-999, (1997).
Ryu, D.D.Y., et al. Recent Progress in Biomolecular Engineering, Biotechnol. Prog. 16:2-16 (2000).
Sa-Ardyen, P., et al. The flexibility of DNA double crossover molecules, Biophys. J., 84:3829-3837, (Jun. 2003).
Saha et al., The promoter of the Chinese hamster ovary dihydrofolate reductase gene regulates the activity of the local origin and helps define its boundaries. Genes Dev. Feb. 15, 2004;18(4):397-410. Epub Feb. 20, 2004.
Saiki, R., et al. Analysis of enzymatically amplified beta-globin and HLA-DQ alpha DNA with allele-specific oligonucleotide probes, Nature, 324(6093):163-166, (Nov. 13, 1986).
Sakabe, N., et al. A Bioinformatics Analysis of Alternative Exon Usage in Human Genes Coding for Extracellular Matrix Proteins, Genetics and Molecular Research, 3(4):532-544, (2004).
Sakamoto, K., et al. Site-Specific Incorporation of an Unnatural Amino Acid Into Proteins in Mammalian Cells, Nucleic Acids Research, 30(21):4692-4699, (2002).
Saks, M. Making sense out of nonsense, PNAS, 98(5):2125-2127, (Feb. 27, 2001).
Saks, M., et al. An Engineered Tetrahymena tRNA.sup.Gln, for in Vivo Incorporation of Unnatural Amino Acids into Proteins by Nonsense Suppression, J. of Biol. Chem., 271(38):23169-23175, (Sep. 20, 1996).
Salyers, A., et al. Conjugative Transposons: an Unusual and Diverse Set of Integrated Gene Transfer Elements, Microbiological Reviews, 59(4):579-590, (Dec. 1995).
Sanjana, N. et al., A Transcription activator-like effector toolbox for genome engineering, Nature Protocols, Nature Publishing Group, GB, Vo. 7. No. 1, pp. 171-192, Jan. 1, 2012.
Sato et al. The cisA cistron of Bacillus subtilis sporulation gene spoIVC encodes a protein homologous to a site-specific recombinase (1990) J. Bacteriol. 172: 1092-1098.
Sato, T., et al. Production of menaquinone (vitamin K2)-7 by Bacillus subtilis, J. of Bioscience and Engineering, 91(1):16-20, (2001).
Sauer, Functional expression of the ere-lox site-specific recombination system in the yeast *Saccharomvces cerevisiae* (1987) Mol. Cell. Biol. 7: 2087-2096.
Schaerli, Y., et al., ContinuoFlow polymerase Chain reaction of single-copy DNA Microfluidic Microdroplets, Anal. Chem., 81: 302-306, (2009).
Scior, Annike et al., Directed PCR-free engineering of highly repetitive DNA sequences, BMC Biotechnology, Biomed Central Ltd., London, GB, vol. 11, No. 1, pp. 87, Sep. 23, 2011.

(56) References Cited

OTHER PUBLICATIONS

Semizarov, D., et al. Stereoisomers of Deoxynucleoside 5'-Triphosphates as Substrates for Template-dependent and-independent DNA Polymerases, J. of Biol. Chem., 272(14):9556-9560, (Apr. 4, 1997).
Seo, T., et al., Four-color DNA sequencing by synthesis on a chip using photocleavable fluorescent nucleotides, PNAS, 102(17):5926-5933, (Apr. 26, 2005).
Sgaramella, V., et al. Studies of polynucleotides, C.: A novel joining reaction catalyzed by T4-polynucleotide ligase, PNAS, 67(3):1468-1475, (Nov. 1970).
Shabarova, Z., et al., Chemical ligation of DNA: the first non-enzymatic assembly of a biologically active gene, Nucl. Acids Res., 19(15):4247-4251, (1991).
Shao, Z., et al. Random-Priming in Vitro Recombination: An Effective Tool for Directed Evolution, Nucleic Acids Research, 26(2):681-683, (1998).
Shendure et al., Accurate Multiplex Polony Sequencing of an Evolved Bacterial Genome, Science. 309:1728-1732 (2005).
Shpaer, GeneAssist. Smith-Waterman and other database similarity searches and identification of motifs: Methods Mol. Biol. 70: 173-187, 1997.
Sieber, V., et al. Libraries of Hybrid Proteins From Distantly Related Sequences, Nature Biotechnology, 19:456-460, (May 2001).
Simon, D., et al. N-methyl-D-aspartate receptor antagonists disrupt the formation of a mammalian neural map Proc Natl Acad Sci USA, 89:10593-10597, (Nov. 1992).
Smith et al., Mutation Detection with MutH, MutL, and MutS Mismatch Repair Proteins, Proc. Natl. Acad. Sci. USA, 93:4374-4379, (Apr. 1996).
Smith et al., Single-step purification of polypeptides expressed in *Escherichia coli* as fusions with glutathione transferase, Gene, vol. 67, Issue 1, pp. 31-40, (1988).
Smith, H.O., et al. Generating a synthetic genome by whole genome assembly:<DX174 bacteriophage from synthetic oligonucleotides, PNAS, 100(26):15440-15445 (2003).
Smith, J., et al. A detailed study of the substrate specificity of a chimeric restriction enzyme. Nucleic Acids Research 27(2):674-681 (1999).
Soderlind, E., et al. Domain libraries: Synthetic diversity for de novo design of antibody V-regions, Gene, 160:269-272, (1995).
Sprinzl et al., Compilation of tRNA sequences and sequences of tRNA genes, Nucleic Acids Research, 33:D139-D140 (2005).
Stamm et al., Sanchored PCR: PCR with CDNA Coupled to a solid phase, Nucleic Acids Research, 19(6):1350, (Mar. 25, 1991).
Stekel, D., "Microarrays: Making Them and Using Them in Microarray Bioinformatics," Cambridge University Press, 2003, (10 pages).
Stemmer W. P. et al., Single-step assembly of a gene and entire plasmid from large numbers of oligodeoxyribonucleotides Gene, 164 (1): 49-53, (1995).
Stemmer, DNA shuffling by random fragmentation and reassembly: in vitro recombination for molecular evolution, Proc. Natl. Acad. Sci. USA, 91:10747-10751, (1994).
Sternberg et al. Site-specific Recombination and Its Role in the Life Cycle of Bacteriophage P1 Cold Spring Harbor Symp. Quant. Biol. 45: 297-309, 1981.
Steuer, S., et al. Chimeras of the Homing Endonuclease Pi-SeeI and the Homologous Candida Tropicalis Intein: A Study to Explore the Possibility of Exchanging DNA-Binding Modules to Obtain Highly Specific Endonucleases With Altered Specificity, ChemBioChem., 5(2):206-213, (2004).
Strizhov N. et al. A synthetic cry1C gene, encoding a Bacillus thuringiensis delta-endotoxin, confers Spodoptera resistance in Alfalfa and Tobacco PNAS, 93(26):15012-15017.
Tan, S., et al. Zinc-finger protein-targeted gene regulation: Genomewide single-gene specificity, PNAS, 100(21):11997-12002, (Oct. 14, 2003).
Tang K. et al. Chip-based genotyping by mass spectrometry. PNAS, 96: 10016-10020 (1999).
Teh et al., Droplet microfluidics, Lab on Chip. 2008;8(2):198-220.
Tian, J., et al. Accurate multiplex gene synthesis from programmable DNA microchips, Nature, 432:1050-1054, (Dec. 2004).

Tsai et al., Dimeric CRISPR RNA-guided FokI nucleases for highly specific genome editing. Nat Biotechnol. Jun. 2014;32(6):569-76. doi: 10.1038/nbt.2908. Epub Apr. 25, 2014. Online Methods.
Tsutakawa et al., The Structural Basis of Damaged DNA Recognition and Endonucleolytic Cleavage for Very Short Patch Repair Endonuclease, Nucleic Acids Research, 29(18):3775-3783, (2001).
Tucker et al., Massively parallel sequencing: the next big thing in genetic medicine. Am J Hum Genet. Aug. 2009;85(2):142-54. doi:10.1016/j.ajhg.2009.06.022.
Urata, H., et al. Synthesis and properties of mirror-image DNA, Nucleic Acids Research, 20(13):3325-3332 (1992).
Venkatesan et al., Improved Utility of Photolabile Solid Phase Synthesis Supports for the Synthesis of Oligonucleotides Containing 3'-Hydroxyl Termini, J. of Org. Chem., 61:525-529, (Jan. 26, 1996).
Verma et al., Modified Oligonucleotides: Synthesis and Strategy for Users, Annu. Rev. Biochem., 67:99-134, (1998).
Vogelstein et al., Digital PCR, Pro. Natl. Acad. Sci. 96(16):9236-9241 (1999).
von Neumann, J. The general and logical theory of automata, Pergamon Press, 5:288-326, (1948).
Wang et al., De novo assembly and characterization of root transcriptome using Illumina paired-end sequencing and development of cSSR markers in sweet potato (*Lpomoea batatas*), BMC Genomics, 2010, vol. 11, pp. 1-14.
Wang et al., Targeted gene addition to a predetermined site in the human genome using a ZFN-based nicking enzyme. Genome Res. Jul. 2012;22(7):1316-26. doi: 10.1101/gr.122879.111. Epub Mar. 20, 2012.
Waters, V. Conjugation between bacterial and mammalian cells, Nature Genetics, 29:375-376, (Dec. 2001).
Weber et al.. A Modular Cloning System for Standardized Assembly of Multigene Constructs, PLoS One, Feb. 18, 2011, vol. 6, No. 2, pp. e16765.
Weiler et al., Combining the Preparation of Oligonucleotide Arrays and Synthesis of High-Quality Primers, Analytical Biochemistry, 243:218-227, (1996).
Weiner et al., Kits and their unique role in molecular biology: a brief retrospective. Biotechniques. Apr. 2008;44(5):701-4. doi: 10.2144/000112796.
Weisberg, et al., Site-specific recombination in Phage Lambda, In: Lambda II, Hendrix, et al. Eds., Cold Spring Harbor Press, Cold Spring Harbor, NY (1983) pp. 211-250.
Werner et al., Fast track assembly of multigene constructs using Golden Gate cloning and the MoClo system, Bioengineered Bugs, Jan. 1, 2012;3(1):38-43.
Wheeler, D., et al. Database resources of the National Center for Biotechnology Information, Nucleic Acids Res., 29(1):11-16, (2001).
White et al. (Digital PCR provides sensitive and absolute calibration for high throughput sequencing, BMC Genomics, 2009, 10:116, Published: Mar. 19, 2009).
Wiedmann et al., Ligase chain reaction (LCR)—overview and applications. PCR Methods Appl. Feb. 1994;3(4):S51-64.
Wilgenbus et al., DNA chip technology ante portas, J. Mol. Med, 77:761-768, (1999).
Williams et al., Modifying the stereochemistry of an enzyme-catalyzed reaction by directed evolution. Proc Natl Acad Sci U S A. Mar. 18, 2003;100(6):3143-8. Epub Mar. 7, 2003.
Xie et al., An Expanding Genetic Code, Methods a Companion to Methods in Enzymology, 36:227-238, (2005).
Xiong et al. PCR based accurate synthesis of long DNA sequences Nature protocols 1 (2): 791 (2006).
Xiong et al., Non-Polymerase-Cycling-Assembly-Based Chemical Gene Synthesis: Strategies, Methods, and Progress; Biotechnology Advances; Elsevier Publishing; Barking, GB; vol. 26; No. 2; pp. 121-134; Nov. 7, 2007.
Xiong, A., et al. A simple, rapid, high-fidelity and cost-effective PCR-based two-step DNA synthesis method for long gene sequences, Nucleic Acids Research, 32(12):e98 (10 pages), (2004).
Xu et al., A novel 5'-iodonucleoside allows efficient nonenzymatic ligation of single-stranded and duplex DNAs, Tetrahedron Letters, 38(32):5595-5598, (1997).

(56) References Cited

OTHER PUBLICATIONS

Xu et al., High sequence fidelity in a non-enzymatic DNA autoligation reaction, Nucleic Acids Research, 27(3):875-881, (1999).

Xu, Y., et al. Nonenzymatic autoligation in direct three-color detection of RNA and DNA point mutations, Nature Biotechnology, 19:148-152, (Feb. 2001).

Xuei et al. Use of SAM(2)(R) biotin capture membrane in microarrayed compound screening (mu ARCS) format for nucleic acid polymerization assays Journal of Biomolecular Screening 8:273-282 (2003).

Yan et al., "Polymer memebranes with two-dimensionally arranged pores derived from monolayers of silica particles," Chem. Mater. 16(9): 1622-1626 (2004).

Yehezkel et al. (De novo DNA synthesis using single molecule PCR, Nucleic Acids Research, 2008, vol. 36, No. 17, e107, Published online Jul. 30, 2008).

Yolov et al. RNA-synthesis by use of T7-RNA-Polymerase and immobilized DNA in a flowing-type reactor. Bioorganicheskaya Khimiya, 17:789-794 (1991).

Yoon et al., Efficient cloning and engineering of entire mitochondrial genomes in *Escherichia coli* and transfer into transcriptionally active mitochondria, Nucleic Acids Research, 31(5):1407-1415, (2003).

Yoon, Y., et al. Cre/loxP-mediated in vivo excision of large segments from yeast genome and their amplification based on the 2 um plasmid-derived system, Gene, 223:67-76, (1998).

Yosef et al., Restoration of gene function by homologous recombination: from PCR to gene expression in one step. Appl Environ Microbiol. Dec. 2004;70(12):7156-60.

Young et al., Two-step Total Gene Synthesis Method Nucleic Acids Research, 32(7):e59 (6 pages), (2004).

Zha, D., et al. Assembly of Designed Oligonucleotides as an Efficient Method for Gene Recombination: A New Tool in Directed Evolution, ChemBioChem, 4:34-39, (2003).

Zhang, C., et al., PCR microfluidic devices for DNA amplification, Biotechnology Advances, 24(3):243-284, 2006.

Zhang, P. et al. Rational Design of a Chimeric Endonuclease Targeted to NotI Recognition Site Protein Engineering Design & Selection, 20(10):497-504, (Oct. 2007).

Zhang, Z., et al. Selective Incorporation of 5-Hydroxytryptophan Into Proteins in Mammalian Cells, Proceedings of the National Academy of Sciences of the United States of America, 101(24):8882-8887, (Jun. 15, 2004).

Zhao, H., et al. Molecular Evolution by Staggered Extension Process (StEP) in Vitro Recombination, Nature Biotechnology, 16:258-261, (Mar. 1998).

Zhou, X., et al., "Microfluidic PicoArray synthesis of oligodeoxynucleotides and simultaneous assembling of multiple DNA sequences" Nucleic Acids Research, 32(18):5409-5417, (2004).

Zhu et al., (1995). Cleavage-dependent Ligation by the FLP Recombinase. J Biol Chem 270: 23044-23054.

\* cited by examiner

METHODS AND DEVICES FOR NUCLEIC ACIDS SYNTHESIS

RELATED APPLICATIONS

This application is a continuation application of U.S. application Ser. No. 15/054,038, filed Feb. 25, 2016, which is a continuation a of U.S. application Ser. No. 13/884,463, filed Jul. 18, 2013 and issued as U.S. Pat. No. 9,295,965, which is a National Stage filing under 35 U.S.C. § 371 of International Application PCT/US2011/060243, filed Nov. 10, 2011, which claims priority to and the benefit under 35 U.S.C. § 119(e) of U.S. Provisional Application No. 61/412,937, filed Nov. 12, 2010, U.S. Provisional Application No. 61/418,095, filed Nov. 30, 2010, U.S. Provisional Application No. 61/466,814, filed Mar. 23, 2011, and U.S. Provisional Application No. 61/503,722, filed Jul. 1, 2011. The contents of each of the foregoing applications are incorporated herein by reference in their entirety.

FIELD OF THE INVENTION

Methods and apparatuses provided herein relate to the synthesis and assembly nucleic acids and nucleic acid libraries having a predefined sequence. More particularly, methods and apparatuses are provided for the synthesis of target polynucleotides on a solid support and for the selection of the target polynucleotides.

BACKGROUND

Using the techniques of recombinant DNA chemistry, it is now common for DNA sequences to be replicated and amplified from nature and then disassembled into component parts. As component parts, the sequences are then recombined or reassembled into new DNA sequences. However, reliance on naturally available sequences significantly limits the possibilities that may be explored by researchers. While it is now possible for short DNA sequences to be directly synthesized from individual nucleosides, it has been generally impractical to directly construct large segments or assemblies of polynucleotides, i.e., polynucleotide sequences longer than about 400 base pairs.

Oligonucleotide synthesis can be performed through massively parallel custom syntheses on microchips (Zhou et al. (2004) Nucleic Acids Res. 32:5409; Fodor et al. (1991) Science 251:767). However, current microchips have very low surface areas and hence only small amounts of oligonucleotides can be produced. When released into solution, the oligonucleotides are present at picomolar or lower concentrations per sequence, concentrations that are insufficiently high to drive bimolecular priming reactions efficiently. Current methods for assembling nucleic acids require that oligonucleotides from microchips to be amplified prior to assembly. As such, a need remains for improved, a cost-effective, methods and devices for high-fidelity gene assembly and the production of large number of polynucleotides sequences.

SUMMARY

Aspects of the invention relate to methods and apparatuses for preparing and/or assembling high fidelity polymers. Also provided herein are devices and methods for processing nucleic acid assembly reactions and assembling nucleic acids. It is an object of this invention to provide practical, economical methods of synthesizing custom nucleic acids.

Aspects of the invention relate to methods and devices for producing a polynucleotide having a predetermined sequence on a solid support. In some embodiments, pluralities of support-bound single-stranded oligonucleotides are provided at different features of a solid support, each plurality of oligonucleotides having a predefined sequence, each plurality being bound to a different discrete feature of the support. In some embodiments, each plurality of oligonucleotides comprises a sequence region at its 3' end that is the complementary to a sequence region of a 3' end of another oligonucleotide and wherein the first plurality of oligonucleotides has a 5' end that is complementary to a 5' end of a first anchor single-stranded oligonucleotide. In some embodiments, the plurality of support-bound oligonucleotides is immobilized on the support. In some embodiments, the plurality of support-bound oligonucleotides is synthesized on the solid support. In other embodiments, the plurality of support-bound oligonucleotides is spotted on the solid support. In some embodiments, the support is a microarray device According to some embodiments, at least a first and a second plurality of support-bound single-stranded oligonucleotides are provided, wherein each first and second plurality of oligonucleotides has a predefined sequence and is bound to a discrete feature of the support. In some embodiments, each first plurality of oligonucleotides comprises a sequence region at its 3' end that is complementary to a sequence region of a 3' end of the second plurality of oligonucleotides. In some embodiments, a plurality support-bound anchor single-stranded oligonucleotides are provided, wherein the 5' end of the plurality of the first anchor oligonucleotide is the same as a sequence region of the first plurality of support-bound oligonucleotides. At least a first and a second pluralities of construction oligonucleotides complementary to the first and second pluralities of support-bound oligonucleotides are generated in a chain extension reaction. The construction oligonucleotides can be hybridized to the plurality of anchor oligonucleotides at a selected feature. The at least first and second pluralities of construction oligonucleotides are ligated, thereby generating the at least one polynucleotide having a predefined sequence. In some embodiments, the at least first and second pluralities of construction oligonucleotides are dissociated from the at least first and second pluralities of support-bound oligonucleotides. In some embodiments, the first plurality of construction oligonucleotides is transferred from a first feature to a selected feature and the second plurality of construction oligonucleotides is transferred from a second feature to the selected feature, wherein the selected feature comprises a plurality support-bound anchor single-stranded oligonucleotides. In some embodiments, the selected feature is on the same support than the first and the second features. Yet in other embodiments, the selected feature is on a different support than the first and second feature. In some embodiments, a third plurality of predefined support-bound single-stranded oligonucleotides is provided, wherein each third plurality of oligonucleotides has a predefined sequence and is bound to a third discrete feature of the support, each third plurality of oligonucleotides comprising a sequence region at its 3' end that is complementary to a sequence region of a 3' end of the second plurality of oligonucleotides. The third plurality of construction oligonucleotides complementary to the third plurality of support-bound oligonucleotides is generated in a chain extension reaction using the single stranded oligonucleotides as templates. The first, second and third pluralities of construction oligonucleotides are hybridized to the plurality of anchor oligonucleotides at a selected feature and ligated to produce a longer polynucleotide. In some embodiments, each plurality of construction oligonucleotides are generated on a different support. In some embodiments, each plurality of support-bound oligonucleotides has a primer binding site at its 3'end. The primer binding site can be a universal primer binding site. In some embodiments, the method comprises annealing a primer to the at least first and second pluralities of support-bound oligonucleotides under conditions promoting primer extension, thereby forming extension product duplexes. In some embodiments, the primer sequence comprises at least one Uracil. In some embodiments, the primer containing Uracil is removed using a mixture of Uracil DNA glycosylase (UDG) and a DNA glycosylase-lyase Endonuclease VIII.

In some embodiments, the method comprises providing N pluralities of predefined support-bound single-stranded oligonucleotides wherein the first plurality of oligonucleotides comprises at its 3' end a sequence region that is complementary to a sequence region at the 3' end of a second oligonucleotide, wherein the N plurality of oligonucleotides comprises at its 3' end a sequence region complementary to a sequence region of the (N−1) oligonucleotide; and providing a first plurality of anchor oligonucleotides comprising at its 5' end a sequence that is the same as a sequence region of the first plurality of support bound oligonucleotides. In some embodiments, N pluralities of construction oligonucleotides complementary to the support-bound single-stranded oligonucleotides are generated, the pluralities of construction oligonucleotides spanning the entire sequence of the polynucleotide without gaps. In some embodiments, the 3' end sequence region of the first plurality of support-bound oligonucleotides is identical to the 5' end region of the anchor oligonucleotides. In some embodiments, the extension products are dissociated thereby releasing the at least first and second pluralities of construction oligonucleotides.

Aspects of the invention relate to a method of synthesizing and selecting a polynucleotide having a predefined sequence. The method comprises synthesizing a plurality of support-bound double-stranded polynucleotides comprising a free single-stranded overhang, the plurality of polynucleotide sequences comprising the predefined polynucleotide sequence, wherein the single-stranded overhang comprises the sequence of a terminal construction oligonucleotide N. In some embodiments, a stem-loop oligonucleotide is provided wherein the stem-loop oligonucleotide comprises a single-stranded overhang and wherein the single-stranded overhang is complementary to the terminal construction oligonucleotide sequence N. The stem-loop oligonucleotide is hybridized and ligated to the free overhang of the polynucleotide having predefined sequence thereby protecting the overhang comprising the terminal oligonucleotide N. In some embodiments, polynucleotide sequences that do not comprise the terminal construction oligonucleotide sequence N are degraded using a single-strand exonuclease such as a single-strand-specific 3' exonuclease, a single strand-specific endonuclease, and a single strand-specific 5' exonuclease. In some embodiments, the methods comprise hybridizing a pool of oligonucleotides to an anchor support-bound single-stranded oligonucleotide, the oligonucleotide pool comprising N pluralities of oligonucleotides wherein the first plurality of oligonucleotides comprises at its 5' end a sequence region that is complementary to a sequence region at the 5' end of the anchor oligonucleotide, and wherein a N plurality of oligonucleotides comprises at its 3' end a sequence complementary to a sequence region of the (N−1) oligonucleotide. In some embodiments, the stem-loop oligonucleotide comprises a type II restriction site and the stem-loop oligonucleotide is removed using a type II restriction endonuclease. In some embodiments, the stem-loop oligonucleotide comprises at least one Uracil nucleotide and the stem-loop oligonucleotide is removed using a mixture of Uracil DNA glycosylase (UDG) and a DNA glycosylase-lyase Endonuclease VIII. In some embodiments, the anchor oligonucleotide and the polynucleotides are released from the support using a mixture of Uracil DNA glycosylase (UDG) and a DNA glycosylase-lyase Endonuclease VIII. In some embodiments, the polynucleotides are released from the support for example using a Type II restriction enzyme. In some embodiments, the predefined polynucleotide sequence is amplified.

In some aspects of the invention, methods for synthesizing a polynucleotide having a predefined sequence and selecting the predefined polynucleotide sequence according to the its sequence and its length are provided. In some embodiments, a support comprising (i) a first plurality of support-bound anchor oligonucleotides, wherein the 5' end of the first plurality of anchor oligonucleotide is complementary to the 5' end of a first plurality of oligonucleotides and (ii) a second plurality of support-bound anchor oligonucleotides wherein the 5' end of the second anchor oligonucleotide is complementary to a terminal construction oligonucleotide N, is provided. In some embodiments, a plurality of support-bound double-stranded polynucleotides comprising a 5' single-stranded overhang are synthesized. The plurality of polynucleotide sequences comprises the predefined polynucleotide sequence, wherein the single-stranded 5' overhang of the predefined polynucleotide sequence comprises the terminal construction oligonucleotide N sequence and the single-stranded 3' end of the polynucleotide sequence comprises the first oligonucleotide sequence. The plurality of synthesized polynucleotides are hybridized, under hybridizing conditions, to the first plurality of anchor oligonucleotides. In some embodiments, the synthesized polynucleotides are subjected to hybridization conditions, such as the terminal oligonucleotide N hybridized to the 5' end of the second plurality of anchor oligonucleotides, thereby selecting the polynucleotides having the predefined sequence using the second anchor oligonucleotide. In some embodiments, the polynucleotide sequences having a free 3' or 5' end are degraded using a single-strand specific exonuclease. In some embodiments, the polynucleotides having the predefined sequence are further released from the support, for example using a Type II endonuclease or using a mixture of Uracil DNA glycosylase (UDG) and a DNA glycosylase-lyase Endonuclease VIII. In preferred embodiments, the first plurality of anchor oligonucleotides is separated from the second plurality of anchor oligonucleotides by a distance corresponding to the length of the predefined polynucleotide. The support can comprise support-bound spacer single-stranded oligonucleotides to set the distance between the first and second anchor oligonucleotides. In some embodiments, the distance between the first and second anchor oligonucleotides is a function of a concentration of the first and second anchor oligonucleotides and of the concentration of the spacer oligonucleotide.

Some aspects of the invention relate to a nucleic acid array comprising (a) a solid support; (b) a plurality of discrete features associated with the solid support wherein each feature comprises a plurality of support-bound oligonucleotides having a predefined sequence, wherein the first plurality of oligonucleotides comprises at its 5' end a sequence region that is complementary to a sequence region at the 5' end of a second oligonucleotide, wherein a plurality of oligonucleotides N comprises at its 5' end a sequence complementary to a 5' end sequence region of a plurality of oligonucleotides (N−1); and (c) at least a first plurality of anchor oligonucleotides comprising at its 5' end a sequence that is identical to a sequence region of the first plurality of support-bound oligonucleotides. In some embodiments, the nucleic acid array further comprises a second plurality of support-bound anchor oligonucleotides wherein the 5' end of the second anchor oligonucleotide is identical to the 5' end of the plurality of oligonucleotides N. In some embodiments, the nucleic acid further comprises a plurality of support-bound oligonucleotides having a sequence that is not identical to the plurality of the plurality of support bound oligonucleotides.

Aspects of the invention relate to a parallel and sequential process for the production of a plurality of polynucleotides having a predefined sequence on a support. In some embodiments, a first and second supports having a plurality of features are provided, wherein each feature on each support comprises a plurality of different support-bound oligonucleotides having a different predefined sequence. A first and second pluralities of different construction oligonucleotides having different predefined sequence are generated using the plurality of support-bound oligonucleotides as templates, the first and second pluralities of construction oligonucleotides having at their 3' end complementary sequences. In some embodiments, a support comprising a plurality of features, wherein each feature comprises a plurality support-bound anchor single-stranded oligonucleotides is provided. In some embodiments, the 5' end of each of the plurality of the anchor oligonucleotides is complementary to the 5' end the first plurality of construction oligonucleotides. The first plurality of construction oligonucleotides can be hybridized to the anchor oligonucleotides forming a first plurality of duplexes having a 3' overhang. The second plurality of construction oligonucleotides can then hybridize to the first plurality of duplexes through the 3' overhang, thereby forming a plurality of duplexes with a 5' overhang. Optionally, depending on the length of the polynucleotide(s) to be synthesized, a third plurality of construction oligonucleotides is hybridized to the second plurality of construction oligonucleotides through the 5' overhang. The pluralities of construction oligonucleotides may be ligated to form the double-stranded polynucleotides. In some embodiments, the step of generating the plurality of first construction oligonucleotides comprises annealing a primer sequence having at least one uracil to the first plurality of support-bound oligonucleotides under conditions promoting extension of the primer and removing the primer using a mixture of Uracil DNA glycosylase (UDG) and a DNA glycosylase-lyase Endonuclease VIII. In some embodiments, the pluralities of construction oligonucleotides defining each of the polynucleotides are synthesized on a different support. The plurality of different polynucleotides can be assembled at a different feature of support comprising the support-bound anchor oligonucleotides.

Aspects of the invention relate to methods and devices for synthesizing a plurality of polynucleotides having a predefined sequence. In some embodiments, the method comprises the steps of (a) providing a first support comprising a plurality of features, wherein each feature comprises a plurality support-bound anchor single-stranded oligonucleotides, wherein the 5' end of each of the plurality of the anchor oligonucleotides is complementary to the 5' end a first plurality of construction oligonucleotides; (b) providing a second support having a plurality of features, wherein each feature comprises a plurality of support-bound oligonucleotides, each plurality of support-bound oligonucleotides having a predefined sequence; (c) generating a first plurality of construction oligonucleotides having different predefined sequences using the plurality of support-bound oligonucleotides as templates; (d) positioning the first and the second supports such as each feature of the second support is aligned to a corresponding feature of the first support; (e) releasing the first plurality of construction oligonucleotides in solution under conditions promoting hybridization of the first plurality of oligonucleotides to plurality of anchor oligonucleotides; and (f) optionally repeating steps b-e with a third support comprising a second plurality of construction oligonucleotides, the second and the third pluralities of construction oligonucleotides having 3' end complementary sequences. In some embodiments, the second support is positioned above and facing the first support. In some embodiments, the third support comprises a plurality of polynucleotides immobilized by hybridization to a plurality of anchor oligonucleotides In some embodiments, the step of generating the plurality of first construction oligonucleotides comprises annealing a primer sequence having at least one uracil to the first plurality of support-bound oligonucleotides under conditions promoting extension of the primer and removing the primer using a mixture of Uracil DNA glycosylase (UDG) and a DNA glycosylase-lyase Endonuclease VIII. The second support can be positioned above and facing the first support. In some embodiments, the solution comprises a ligase allowing for the ligation of the second and third pluralities of construction oligonucleotides.

In some embodiments, the step of releasing the first plurality of construction oligonucleotides in solution allows for the diffusion of the first plurality of oligonucleotides towards the anchor oligonucleotides.

In some embodiments, the step of releasing the first plurality of construction oligonucleotides in solution is in presence of a permeable membrane allowing for a substantial vertical diffusion of the construction oligonucleotides towards the anchor oligonucleotides. In some embodiments, the permeable membrane decreases the lateral diffusion of construction oligonucleotides.

In some embodiments, each feature of the second support comprises a plurality of oligonucleotides wherein the plurality of oligonucleotides comprises at least two populations of oligonucleotides having different predefined sequences, the at least two populations of oligonucleotides having complementary sequences. For example, the two populations of oligonucleotides comprise 3' end complementary sequences. In some embodiments, the two populations of oligonucleotides are released in solution thereby allowing for the hybridization of the first population of construction oligonucleotides to the second population of construction oligonucleotides and for the hybridization of the first population of oligonucleotides to the anchor oligonucleotides. In some embodiments, the solution comprises a ligase. In some embodiments, the stoichiometry of the first plurality of construction oligonucleotides is higher than the stoichiometry of the anchor oligonucleotides.

In some embodiments, the method of synthesizing a plurality of polynucleotides having a predefined sequence further comprises exposing the plurality of polynucleotides to a mismatch recognizing and cleaving component under conditions suitable for cleavage of double-stranded polynucleotides containing a mismatch. The plurality of polynucleotides can be support-bound or in solution. The mismatch recognizing and cleaving component can comprise a mismatch endonuclease such as a CEL I enzyme.

BRIEF DESCRIPTION OF THE FIGURES

FIG. 1a illustrates a nucleic acid array 10 having an arrangement of features 20, with each feature comprising a plurality of support-bound single-stranded oligonucleotides 30. FIG. 1b illustrates annealing of a primer 50 to the support-bound oligonucleotides and extension of the primer to form construction oligonucleotides 60. FIG. 1c illustrates release of construction oligonucleotides 65 from support 10. FIG. 1d illustrates transfer of construction oligonucleotides 65 to surface 15 having anchor support-bound oligonucleotide 40 having a sequence complementary to construction oligonucleotide 1 and hybridization of construction oligonucleotides 1, 2, 3, and 4 to each other to assemble into longer polynucleotide 70. FIG. 1e illustrates the ligation of construction oligonucleotides to form longer polynucleotide construct 90.

FIG. 2a illustrates an oligonucleotide array 110 comprising on the same surface support-bound oligonucleotides 130 (support-bound oligonucleotides 1', 2'; 3' and 4') and support-bound anchor oligonucleotides 140 (A). FIG. 2b illustrates hybridization of primer 150 to support bound oligonucleotides 130 and extension of the primer to form construction oligonucleotides 160 (construction oligonucleotides 1, 2, 3 and 4). FIG. 2c illustrates release of extension products 165 (construction oligonucleotides 1, 2, 3 and 4). FIG. 2d illustrates hybridization of construction oligonucleotide 1 to the anchor support-bound oligonucleotide 140 and hybridization of construction oligonucleotides to each other to form longer nucleic acid construct 170. FIG. 2e illustrates the ligation of construction oligonucleotides to form longer polynucleotide construct 190.

FIG. 3a illustrates generation of construction oligonucleotides 65 using a nucleic acid array 10 having a plurality of support-bound single-stranded oligonucleotides 30. FIG. 3b illustrates generation of undesired assemblies 72 and 74 and full length assemblies 70 and the addition of a stem-loop oligonucleotide 200 to filter out undesired assemblies. FIG. 3c illustrates hybridization of stem-loop oligonucleotide 200 to full length assembly product 70. FIG. 3d illustrates ligation of stem-loop oligonucleotide 200 to full length assembly product 70. FIG. 3e illustrates digestion of undesired constructs which did not hybridize/ligate to the stem-loop oligonucleotides.

FIG. 4a illustrates synthesis of construction oligonucleotides 265 using a plurality of support-bound single-stranded oligonucleotides 230 as templates on array 210. FIG. 4b illustrates surface 215 having a first plurality of anchor oligonucleotides 240 and a second plurality of oligonucleotides 242 immobilized on the support and hybridization of construction oligonucleotides 265 to each other and to the anchor oligonucleotides to generate support-bound polynucleotide constructs 270, 272, 273, 274. FIG. 4c illustrates hybridization of the 5'-overhang of the full length construct to second anchor oligonucleotide 242.

FIG. 7a illustrates release of a first set of construction oligonucleotides 371 ($A_1$, $B_1$, $C_1$, $D_1$) from construction array 311, transfer and annealing to anchor oligonucleotides ($A_0$, $B_0$, $C_0$, $D_0$) of anchor array 310 to form duplexes 381 (e.g. $A_0A_1$, $B_0B_1$, $C_0C_1$, $D_0D_1$). FIG. 7b illustrates release of second population of different construction oligonucleotides 372 ($A_2$, $B_2$, $C_2$, $D_2$) from construction array 312 and annealing to the free 3' overhang of the anchor-first construction oligonucleotides duplexes 381 attached the anchor array 310 to form duplexes 382 ($A_0A_1A_2$, $B_0B_1B_2$, $C_0C_1C_2$, $D_0D_1D_2$).

FIG. 9a illustrates a top construction array 411 and an anchor array 410. FIG. 9b illustrates release of a first set of construction oligonucleotides ($A_1$, $B_1$, $C_1$, $D_1$) in fluid medium 485 and capture of the oligonucleotides onto the anchor array to form a plurality of duplexes 441 (441, $A_0A_1$, $B_0B_1$, $C_0C_1$, $D_0D_1$). FIG. 9c illustrates alignment and approximation of a second construction array 412 to anchor array 410 in presence of a fluid medium 485. FIG. 9d illustrates release of second set of construction oligonucleotides 462 ($A_2$, $B_2$, $C_2$, $D_2$) from microarray 412 and annealing to anchor microarray 410 to form polynucleotides 442 ($A_0A_1A_2$, $B_1B_2B_2$, $C_0C_1C_2$, $D_0D_1D_2$). FIG. 9e illustrates an anchor array 410 having on its surface a plurality of polynucleotides 452 which have been assembled by means of the process described in FIGS. 9a-d. The assembled polynucleotides may contain one or more sequence errors 500 (illustrated by a cross). FIG. 9f illustrates cleavage of double-stranded polynucleotide 500 having errors sites resulting in cleaved polynucleotides 453.

DETAILED DESCRIPTION OF THE INVENTION

Figure 1:
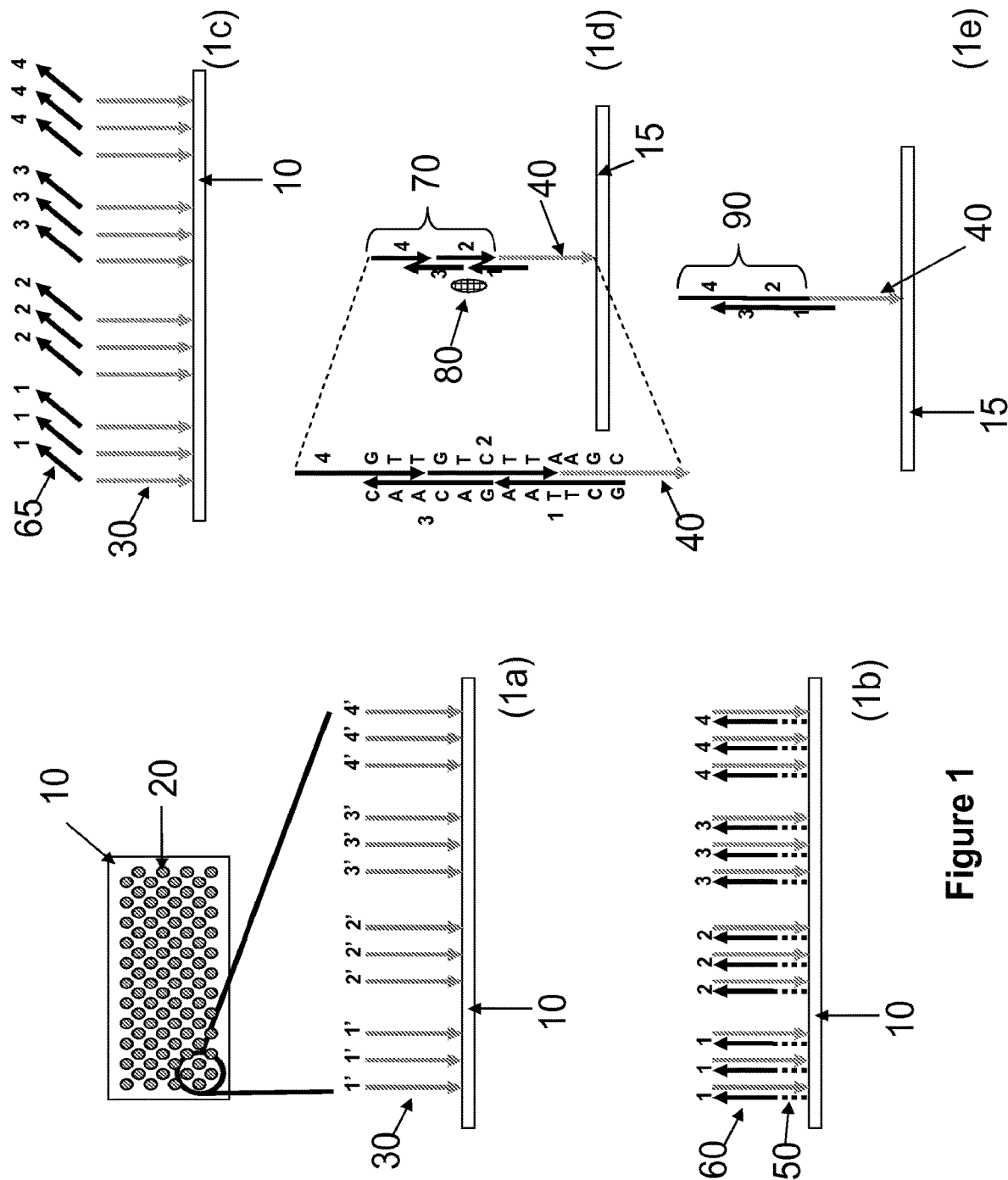
FIG. 1 illustrates a non-limiting exemplary method of surface attached nucleic acid synthesis using a first oligonucleotide generating surface and a second anchor oligonucleotide surface.

Aspects of the technology provided herein are useful for increasing the accuracy, yield, throughput, and/or cost efficiency of nucleic acid synthesis and assembly reactions. As used herein the terms "nucleic acid", "polynucleotide", "oligonucleotide" are used interchangeably and refer to naturally-occurring or synthetic polymeric forms of nucleotides. The oligonucleotides and nucleic acid molecules of the present invention may be formed from naturally occurring nucleotides, for example forming deoxyribonucleic acid (DNA) or ribonucleic acid (RNA) molecules. Alternatively, the naturally occurring oligonucleotides may include structural modifications to alter their properties, such as in peptide nucleic acids (PNA) or in locked nucleic acids (LNA). The solid phase synthesis of oligonucleotides and nucleic acid molecules with naturally occurring or artificial bases is well known in the art. The terms should be understood to include equivalents, analogs of either RNA or DNA made from nucleotide analogs and as applicable to the embodiment being described, single-stranded or double-stranded polynucleotides. Nucleotides useful in the invention include, for example, naturally-occurring nucleotides (for example, ribonucleotides or deoxyribonucleotides), or natural or synthetic modifications of nucleotides, or artificial bases. As used herein, the term monomer refers to a member of a set of small molecules which are and can be joined together to form an oligomer, a polymer or a compound composed of two or more members. The particular ordering of monomers within a polymer is referred to herein as the "sequence" of the polymer. The set of monomers includes, but is not limited to, for example, the set of common L-amino acids, the set of D-amino acids, the set of synthetic and/or natural amino acids, the set of nucleotides and the set of pentoses and hexoses. Aspects of the invention are described herein primarily with regard to the preparation of oligonucleotides, but could readily be applied in the preparation of other polymers such as peptides or polypeptides, polysaccharides, phospholipids, heteropolymers, polyesters, polycarbonates, polyureas, polyamides, polyethyleneimines, polyarylene sulfides, polysiloxanes, polyimides, polyacetates, or any other polymers.

As used herein, the term "predetermined sequence" or "predefined sequence" are used interchangeably and means that the sequence of the polymer is known and chosen before synthesis or assembly of the polymer. In particular, aspects of the invention are described herein primarily with regard to the preparation of nucleic acid molecules, the sequence of the nucleic acids being known and chosen before the synthesis or assembly of the nucleic acid molecules. In some embodiments of the technology provided herein, immobilized oligonucleotides or polynucleotides are used as a source of material. In various embodiments, the methods described herein use oligonucleotides, their sequence being determined based on the sequence of the final polynucleotide constructs to be synthesized. In one embodiment, oligonucleotides are short nucleic acid molecules. For example, oligonucleotides may be from 10 to about 300 nucleotides, from 20 to about 400 nucleotides, from 30 to about 500 nucleotides, from 40 to about 600 nucleotides, or more than about 600 nucleotides long. However, shorter or longer oligonucleotides may be used. Oligonucleotides may be designed to have different length. In some embodiments, the sequence of the polynucleotide construct may be divided up into a plurality of shorter sequences that can be synthesized in parallel and assembled into a single or a plurality of desired polynucleotide constructs using the methods described herein. In some embodiments, the assembly procedure may include several parallel and/or sequential reaction steps in which a plurality of different nucleic acids or oligonucleotides are synthesized or immobilized, primer-extended, and are combined in order to be assembled (e.g., by extension or ligation as described herein) to generate a longer nucleic acid product to be used for further assembly, cloning, or other applications.

In some embodiments, methods of assembling libraries containing nucleic acids having predetermined sequence variations are provided herein. Assembly strategies provided herein can be used to generate very large libraries representative of many different nucleic acid sequences of interest. In some embodiments, libraries of nucleic acids are libraries of sequence variants. Sequence variants may be variants of a single naturally-occurring protein encoding sequence. However, in some embodiments, sequence variants may be variants of a plurality of different protein-encoding sequences. Accordingly, one aspect of the technology provided herein relates to the assembly of precise high-density nucleic acid libraries. Aspects of the technology provided herein also provide precise high-density nucleic acid libraries. A high-density nucleic acid library may include more that 100 different sequence variants (e.g., about $10^2$ to $10^3$; about $10^3$ to $10^4$; about $10^4$ to $10^5$; about $10^5$ to $10^6$; about $10^6$ to $10^7$; about $10^7$ to $10^8$; about $10^8$ to $10^9$; about $10^9$ to $10^{10}$; about $10^{10}$ to $10^{11}$; about $10^{11}$ to $10^{12}$; about $10^{12}$ to $10^{13}$; about $10^{13}$ to $10^{14}$; about $10^{14}$ to $10^{15}$; or more different sequences) wherein a high percentage of the different sequences are specified sequences as opposed to random sequences (e.g., more than about 50%, more than about 60%, more than about 70%, more than about 75%, more than about 80%, more than about 85%, more than about 90%, about 91%, about 92%, about 93%, about 94%, about 95%, about 96%, about 97%, about 98%, about 99%, or more of the sequences are predetermined sequences of interest).

In some embodiments, the methods and devices provided herein use oligonucleotides that are immobilized on a surface or substrate (e.g., support-bound oligonucleotides). Support-bound oligonucleotides comprise for example, oligonucleotides complementary to construction oligonucleotides, anchor oligonucleotides and/or spacer oligonucleotides. As used herein the terms "support", "substrate" and "surface" are used interchangeably and refer to a porous or non-porous solvent insoluble material on which polymers such as nucleic acids are synthesized or immobilized. As used herein "porous" means that the material contains pores having substantially uniform diameters (for example in the nm range). Porous materials include paper, synthetic filters etc. In such porous materials, the reaction may take place within the pores. The support can have any one of a number of shapes, such as pin, strip, plate, disk, rod, bends, cylindrical structure, particle, including bead, nanoparticles and the like. The support can have variable widths. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly (4-methylbutene), polystyrene, polymethacrylate, poly(ethylene terephthalate), nylon, poly(vinyl butyrate), polyvinylidene difluoride (PVDF) membrane, glass, controlled pore glass, magnetic controlled pore glass, ceramics, metals, and the like etc.; either used by themselves or in conjunction with other materials. In some embodiments, oligonucleotides are synthesized in an array format. For example, single-stranded oligonucleotides are synthesized in situ on a common support, wherein each oligonucleotide is synthesized on a separate or discrete feature (or spot) on the substrate. In preferred embodiments, single-stranded oligonucleotides are bound to the surface of the support or feature. As used herein the term "array" refers to an arrangement of discrete features for storing, amplifying and releasing oligonucleotides or complementary oligonucleotides for further reactions. In a preferred embodiment, the support or array is addressable: the support includes two or more discrete addressable features at a particular predetermined location (i.e., an "address") on the support. Therefore, each oligonucleotide molecule on the array is localized to a known and defined location on the support. The sequence of each oligonucleotide can be determined from its position on the support. The array may comprise interfeatures regions. Interfeatures may not carry any oligonucleotide on their surface and may correspond to inert space.

In some embodiments, oligonucleotides are attached, spotted, immobilized, surface-bound, supported or synthesized on the discrete features of the surface or array. Oligonucleotides may be covalently attached to the surface or deposited on the surface. Arrays may be constructed, custom ordered or purchased from a commercial vendor (e.g., Agilent, Affymetrix, Nimblegen). Various methods of construction are well known in the art e.g., maskless array synthesizers, light directed methods utilizing masks, flow channel methods, spotting methods etc. In some embodiments, construction and/or selection oligonucleotides may be synthesized on a solid support using maskless array synthesizer (MAS). Maskless array synthesizers are described, for example, in PCT application No. WO 99/42813 and in corresponding U.S. Pat. No. 6,375,903. Other examples are known of maskless instruments which can fabricate a custom DNA microarray in which each of the features in the array has a single-stranded DNA molecule of desired sequence. Other methods for synthesizing oligonucleotides include, for example, light-directed methods utilizing masks, flow channel methods, spotting methods, pin-based methods, and methods utilizing multiple supports. Light directed methods utilizing masks (e.g., VLSIPS™ methods) for the synthesis of oligonucleotides is described, for example, in U.S. Pat. Nos. 5,143,854, 5,510,270 and 5,527,681. These methods involve activating predefined regions of a solid support and then contacting the support with a preselected monomer solution. Selected regions can be activated by irradiation with a light source through a mask much in the manner of photolithography techniques used in integrated circuit fabrication. Other regions of the support remain inactive because illumination is blocked by the mask and they remain chemically protected. Thus, a light pattern defines which regions of the support react with a given monomer. By repeatedly activating different sets of predefined regions and contacting different monomer solutions with the support, a diverse array of polymers is produced on the support. Other steps, such as washing unreacted monomer solution from the support, can be optionally used. Other applicable methods include mechanical techniques such as those described in U.S. Pat. No. 5,384,261. Additional methods applicable to synthesis of oligonucleotides on a single support are described, for example, in U.S. Pat. No. 5,384,261. For example, reagents may be delivered to the support by either (1) flowing within a channel defined on predefined regions or (2) "spotting" on predefined regions. Other approaches, as well as combinations of spotting and flowing, may be employed as well. In each instance, certain activated regions of the support are mechanically separated from other regions when the monomer solutions are delivered to the various reaction sites. Flow channel methods involve, for example, microfluidic systems to control synthesis of oligonucleotides on a solid support. For example, diverse polymer sequences may be synthesized at selected regions of a solid support by forming flow channels on a surface of the support through which appropriate reagents flow or in which appropriate reagents are placed. Spotting methods for preparation of oligonucleotides on a solid support involve delivering reactants in relatively small quantities by directly depositing them in selected regions. In some steps, the entire support surface can be sprayed or otherwise coated with a solution, if it is more efficient to do so. Precisely measured aliquots of monomer solutions may be deposited dropwise by a dispenser that moves from region to region. Pin-based methods for synthesis of oligonucleotides on a solid support are described, for example, in U.S. Pat. No. 5,288,514. Pin-based methods utilize a support having a plurality of pins or other extensions. The pins are each inserted simultaneously into individual reagent containers in a tray. An array of 96 pins is commonly utilized with a 96-container tray, such as a 96-well microtiter dish. Each tray is filled with a particular reagent for coupling in a particular chemical reaction on an individual pin. Accordingly, the trays will often contain different reagents. Since the chemical reactions have been optimized such that each of the reactions can be performed under a relatively similar set of reaction conditions, it becomes possible to conduct multiple chemical coupling steps simultaneously.

In another embodiment, a plurality of oligonucleotides may be synthesized or immobilized on multiple supports. One example is a bead based synthesis method which is described, for example, in U.S. Pat. Nos. 5,770,358; 5,639,603; and 5,541,061. For the synthesis of molecules such as oligonucleotides on beads, a large plurality of beads is suspended in a suitable carrier (such as water) in a container. The beads are provided with optional spacer molecules having an active site to which is complexed, optionally, a protecting group. At each step of the synthesis, the beads are divided for coupling into a plurality of containers. After the nascent oligonucleotide chains are deprotected, a different monomer solution is added to each container, so that on all beads in a given container, the same nucleotide addition reaction occurs. The beads are then washed of excess reagents, pooled in a single container, mixed and re-distributed into another plurality of containers in preparation for the next round of synthesis. It should be noted that by virtue of the large number of beads utilized at the outset, there will similarly be a large number of beads randomly dispersed in the container, each having a unique oligonucleotide sequence synthesized on a surface thereof after numerous rounds of randomized addition of bases. An individual bead may be tagged with a sequence which is unique to the double-stranded oligonucleotide thereon, to allow for identification during use.

Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) Proc. Natl. Acad. Sci. U.S.A. 93:13555; Synthetic DNA Arrays In Genetic Engineering, Vol. 20:111, Plenum Press (1998); Duggan et al. (1999) Nat. Genet. S21:10; Microarrays: Making Them and Using Them In Microarray Bioinformatics, Cambridge University Press, 2003; U.S. Patent Application Publication Nos. 2003/0068633 and 2002/0081582; U.S. Pat. Nos. 6,833,450, 6,830,890, 6,824,866, 6,800,439, 6,375,903 and 5,700,637; and PCT Publication Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597; the disclosures of which are incorporated herein by reference in their entirety for all purposes. In some embodiments, pre-synthesized oligonucleotides are attached to a support or are synthesized using a spotting methodology wherein monomers solutions are deposited dropwise by a dispenser that moves from region to region (e.g., ink jet). In some embodiments, oligonucleotides are spotted on a support using, for example, a mechanical wave actuated dispenser.

In one aspect, the invention relates to a method for producing target polynucleotides having a predefined sequence on a solid support. The synthetic polynucleotides are at least about 1, 2, 3, 4, 5, 8, 10, 15, 20, 25, 30, 40, 50, 75, or 100 kilobases (kb), or 1 megabase (mb), or longer. In some aspects, the invention relate to a method for the production of high fidelity polynucleotides. In exemplary embodiments, a compositions of synthetic polynucleotides contains at least about 1%, 2%, 3%, 4%, 5%, 6%, 7%, 8%, 9%, 10%, 15%, 20%, 25%, 50%, 60%, 70%, 80%, 90%, 95% or more, copies that are error free (e.g., having a sequence that does not deviate from a predetermined sequence). The percent of error free copies is based on the number of error free copies in the composition as compared to the total number of copies of the polynucleotide in the composition that were intended to have the correct, e.g., predefined or predetermined, sequence.

In some embodiments, the nucleic acid target sequence can be obtained in a single step by mixing together all of the overlapping oligonucleotides needed to form the polynucleotide construct having the predefined sequence. Alternatively, a series of assembly reactions may be performed in parallel or serially, such that larger polynucleotide constructs may be assembled from a series of separate assembly reactions.

Some aspects the invention relate to the design of oligonucleotides for the high fidelity polynucleotide assembly. Aspects of the invention may be useful to increase the throughput rate of a nucleic acid assembly procedure and/or reduce the number of steps or amounts of reagent used to generate a correctly assembled nucleic acid sequence. In certain embodiments, aspects of the invention may be useful in the context of automated nucleic acid assembly to reduce the time, number of steps, amount of reagents, and other factors required for the assembly of each correct nucleic acid sequence. Accordingly, these and other aspects of the invention may be useful to reduce the cost and time of one or more nucleic acid assembly procedures.

Some aspects of the invention relate to a polynucleotide assembly process wherein synthetic oligonucleotides are designed and used as templates for primer extension reactions, synthesis of complementary oligonucleotides and to assemble polynucleotides into longer polynucleotides constructs. In some embodiments, the method includes synthesizing a plurality of oligonucleotides or polynucleotides in a chain extension reaction using a first plurality of single-stranded oligonucleotides as templates. As noted above, the oligonucleotides may be first synthesized onto a plurality of discrete features of the surface, or may be deposited on the plurality of features of the support. The support may comprise at least 100, at least 1,000, at least $10^4$, at least $10^5$, at least $10^6$, at least $10^7$, at least $10^8$ features. In a preferred embodiment, the oligonucleotides are covalently attached to the support. In preferred embodiments, the pluralities of oligonucleotides are immobilized to a solid surface. In a preferred embodiment, each feature of the solid surface comprises a high density of oligonucleotides having a different predetermined sequence (e.g., approximately $10^6$-$10^8$ molecules per feature).

In some embodiments, pluralities of different single-stranded oligonucleotides are immobilized at different features of a solid support. In some embodiments, the support-bound oligonucleotides may be attached through their 5' end. In a preferred embodiment, the support-bound oligonucleotides are attached through their 3' end. In some embodiments, the support-bound oligonucleotides may be immobilized on the support via a nucleotide sequence (e.g. degenerate binding sequence), linker or spacer (e.g. photocleavable linker or chemical linker). It should be appreciated that by 3' end, it is meant the sequence downstream to the 5' end and by 5' end it is meant the sequence upstream to the 3' end. For example, an oligonucleotide may be immobilized on the support via a nucleotide sequence, linker or spacer that is not involved in hybridization. The 3' end sequence of the support-bound oligonucleotide referred then to a sequence upstream to the linker or spacer.

In certain embodiments, oligonucleotides may be designed to have a sequence that is identical or complementary to a different portion of the sequence of a predetermined target polynucleotide that is to be assembled. Accordingly, in some embodiments, each oligonucleotide may have a sequence that is identical or complementary to a portion of one of the two strands of a double-stranded target nucleic acid. As used herein, the term "complementary" refers to the capacity for precise pairing between two nucleotides. For example, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules.

In some embodiments, the plurality of construction oligonucleotides are designed such as each plurality of construction oligonucleotides comprising a sequence region at its 5' end that is complementary to sequence region of the 5' end of another construction oligonucleotide and a sequence region at its 3' end that is complementary to a sequence region at a 3' end of a different construction oligonucleotide. As used herein, a "construction" oligonucleotide refers to one of the plurality or population of single-stranded oligonucleotides used for polynucleotide assembly. The plurality of construction oligonucleotides comprises oligonucleotides for both the sense and antisense strand of the target polynucleotide. Construction oligonucleotides can have any length, the length being designed to accommodate an overlap or complementary sequence. Construction oligonucleotides can be of identical size or of different sizes. In preferred embodiments, the construction oligonucleotides span the entire sequence of the target polynucleotide without any gaps. Yet in other embodiments, the construction oligonucleotides are partially overlapping resulting in gaps between construction oligonucleotides when hybridized to each other. Preferably, the pool or population of construction oligonucleotides comprises construction oligonucleotides having overlapping sequences so that construction oligonucleotides can hybridize to one another under the appropriate hybridization conditions. One would appreciate that each internal construction oligonucleotides will hybridize to two different construction oligonucleotide whereas the construction oligonucleotides at the 5' and/or 3' end will hybridize each to a different (or the same) internal oligonucleotide(s). Hybridization and ligation of the overlapping construction oligonucleotides will therefore result in a target polynucleotide having a 3' and/or a 5' overhang. Yet in some embodiments, the resulting target polynucleotide may comprise blunt end at its 5' or/and 3' terminus. In some embodiments, if the target polynucleotide is assembled from N construction oligonucleotides, 1 to N pluralities of different support-bound single-stranded oligonucleotides are designed such as the first plurality of construction oligonucleotides comprises at its 5' end a sequence region that is complementary to a sequence region at the 5' end of an anchor oligonucleotide and wherein a N plurality of construction oligonucleotides comprises at its 3' end a sequence region that is complementary to a 3' end sequence region of the (N−1) construction oligonucleotide. In some embodiments, the first plurality of oligonucleotides has a 5' end that is complementary to the 5' end of a support bound anchor single-stranded oligonucleotide. As used herein, the anchor oligonucleotide refers to an oligonucleotide designed to be complementary to at least a portion of the target polynucleotide and may be immobilized on the support. In an exemplary embodiment, the anchor oligonucleotide has a sequence complementary to the 5' end of the target polynucleotide and may be immobilized on the support.

It should be appreciated that different oligonucleotides may be designed to have different lengths with overlapping sequence regions. Overlapping sequence regions may be identical (i.e., corresponding to the same strand of the nucleic acid fragment) or complementary (i.e., corresponding to complementary strands of the nucleic acid fragment). Overlapping sequences may be of any suitable length. Overlapping sequences may be between about 5 and about 500 nucleotides long (e.g., between about 10 and 100, between about 10 and 75, between about 10 and 50, about 20, about 25, about 30, about 35, about 40, about 45, about 50, etc. . . . nucleotides long) However, shorter, longer or intermediate overlapping lengths may be used. It should be appreciated that overlaps (5' or 3' regions) between different input nucleic acids used in an assembly reaction may have different lengths. In some embodiments, anchor support-bound (or immobilized) oligonucleotides include sequence regions having overlapping regions to assist in the assembly of a predetermined nucleic acid sequence. In a preferred embodiment, anchor oligonucleotides include sequence regions having complementary regions for hybridization to a different oligonucleotide or to a polynucleotide (such as, for example, a sub-assembly product). The complementary regions refer to a sequence region at either a 3' end or a 5' end of the immobilized template oligonucleotide (e.g. template oligonucleotide). In a preferred embodiment, the complementary region is localized at the 5' end of the anchor oligonucleotides. Complementary regions refer to a 3' end or a 5' region of a first oligonucleotide or polynucleotide that is capable of hybridizing to a 5' end or 3' end of a second oligonucleotide or polynucleotide.

In some embodiments, nucleic acids are assembled using ligase-based assembly techniques, wherein the oligonucleotides are designed to provide full length sense (or plus strand) and antisense (or minus strand) strands of the target polynucleotide construct. After hybridization of the sense and antisense oligonucleotides, the oligonucleotides on each strand are subjected to ligation in order to form the target polynucleotide construct or a sub-assembly product. Reference is made to U.S. Pat. No. 5,942,609, which is incorporated herein in its entirety. Ligase-based assembly techniques may involve one or more suitable ligase enzymes that can catalyze the covalent linking of adjacent 3' and 5' nucleic acid termini (e.g., a 5' phosphate and a 3' hydroxyl of nucleic acid(s) annealed on a complementary template nucleic acid such that the 3' terminus is immediately adjacent to the 5' terminus). Accordingly, a ligase may catalyze a ligation reaction between the 5' phosphate of a first nucleic acid to the 3' hydroxyl of a second nucleic acid if the first and second nucleic acids are annealed next to each other on a template nucleic acid. A ligase may be obtained from recombinant or natural sources. A ligase may be a heat-stable ligase. In some embodiments, a thermostable ligase from a thermophilic organism may be used. Examples of thermostable DNA ligases include, but are not limited to: Tth DNA ligase (from *Thermus thermophilus*, available from, for example, Eurogentec and GeneCraft); Pfu DNA ligase (a hyperthermophilic ligase from *Pyrococcus furiosus*); Taq ligase (from *Thermus aquaticus*), Ampliligase® (available from Epicenter Biotechnologies) any other suitable heat-stable ligase, or any combination thereof. In some embodiments, one or more lower temperature ligases may be used (e.g., T4 DNA ligase). A lower temperature ligase may be useful for shorter overhangs (e.g., about 3, about 4, about 5, or about 6 base overhangs) that may not be stable at higher temperatures.

Non-enzymatic techniques can be used to ligate nucleic acids. For example, a 5'-end (e.g., the 5' phosphate group) and a 3'-end (e.g., the 3' hydroxyl) of one or more nucleic acids may be covalently linked together without using enzymes (e.g., without using a ligase). In some embodiments, non-enzymatic techniques may offer certain advantages over enzyme-based ligations. For example, non-enzymatic techniques may have a high tolerance of non-natural nucleotide analogues in nucleic acid substrates, may be used to ligate short nucleic acid substrates, may be used to ligate RNA substrates, and/or may be cheaper and/or more suited to certain automated (e.g., high throughput) applications.

Non-enzymatic ligation may involve a chemical ligation. In some embodiments, nucleic acid termini of two or more different nucleic acids may be chemically ligated. In some embodiments, nucleic acid termini of a single nucleic acid may be chemically ligated (e.g., to circularize the nucleic acid). It should be appreciated that both strands of a first double-stranded nucleic acid terminus may be chemically ligated to both strands at a second double-stranded nucleic acid terminus. However, in some embodiments only one strand of a first nucleic acid terminus may be chemically ligated to a single strand of a second nucleic acid terminus. For example, the 5' end of one strand of a first nucleic acid terminus may be ligated to the 3' end of one strand of a second nucleic acid terminus without the ends of the complementary strands being chemically ligated.

Accordingly, a chemical ligation may be used to form a covalent linkage between a 5' terminus of a first nucleic acid end and a 3' terminus of a second nucleic acid end, wherein the first and second nucleic acid ends may be ends of a single nucleic acid or ends of separate nucleic acids. In one aspect, chemical ligation may involve at least one nucleic acid substrate having a modified end (e.g., a modified 5' and/or 3' terminus) including one or more chemically reactive moieties that facilitate or promote linkage formation. In some embodiments, chemical ligation occurs when one or more nucleic acid termini are brought together in close proximity (e.g., when the termini are brought together due to annealing between complementary nucleic acid sequences). Accordingly, annealing between complementary 3' or 5' overhangs (e.g., overhangs generated by restriction enzyme cleavage of a double-stranded nucleic acid) or between any combination of complementary nucleic acids that results in a 3' terminus being brought into close proximity with a 5' terminus (e.g., the 3' and 5' termini are adjacent to each other when the nucleic acids are annealed to a complementary template nucleic acid) may promote a template-directed chemical ligation. Examples of chemical reactions may include, but are not limited to, condensation, reduction, and/or photochemical ligation reactions. It should be appreciated that in some embodiments chemical ligation can be used to produce naturally-occurring phosphodiester internucleotide linkages, non-naturally-occurring phosphamide pyrophosphate internucleotide linkages, and/or other non-naturally-occurring internucleotide linkages.

In some aspects of the invention, oligonucleotides are assembled by polymerase chain extension. In some embodiments, the first step of the extension reaction uses a primer. In some embodiments, the oligonucleotides may comprise universal (common to all oligonucleotides), semi-universal (common to at least of portion of the oligonucleotides) or individual or unique primer (specific to each oligonucleotide) binding sites on either the 5' end or the 3' end or both ends. As used herein, the term "universal" primer or primer binding site means that a sequence used to amplify the oligonucleotide is common to all oligonucleotides such that all such oligonucleotides can be amplified using a single set of universal primers. In other circumstances, an oligonucleotide contains a unique primer binding site. As used herein, the term "unique primer binding site" refers to a set of primer recognition sequences that selectively amplifies a subset of oligonucleotides. In yet other circumstances, an oligonucleotide contains both universal and unique amplification sequences, which can optionally be used sequentially. In a first step, a primer is added and anneals to an immobilized or support-bound oligonucleotide. For example, the primer can anneal to an immobilized anchor oligonucleotide. In some embodiments, the primer is designed to be complementary to a sequence of the support-bound or immobilized oligonucleotides, referred to as primer binding site. In the first step, a solution comprising a polymerase, at least one primer and dNTPs, is added at a feature of the solid support under conditions promoting primer extension. For example, referring to FIG. 1b, a primer (50) is added at a feature comprising oligonucleotides (1', 2', 3', and 4'). The primer hybridizes to the primer binding site of the support-bound oligonucleotides and under conditions promoting primer extension, the primer is extended into a complementary oligonucleotide (1, 2, 3 or 4) using support-bound sequence (1', 2' 3' or 4') as a template.

In some embodiments, uracil DNA glycosylase (UDG) may be used to hydrolyze a uracil-glycosidic bond in a nucleic acid thereby removing uracil and creating an alkali-sensitive basic site in the DNA which can be subsequently hydrolyzed by endonuclease, heat or alkali treatment. As a result, a portion of one strand of a double-stranded nucleic acid may be removed thereby exposing the complementary sequence in the form of a single-stranded overhang. This approach requires the deliberate incorporation of one or more uracil bases in one strand of a double-stranded nucleic acid fragment. This may be accomplished, for example, by amplifying a nucleic acid fragment using an amplification primer that contains a 3' terminal uracil. In some embodiments, the primer is a primer containing multiple uracil (U). The primer is first annealed to a support-bound single-stranded oligonucleotide and extended with the addition of dNTPs and an appropriate polymerase under appropriate conditions and temperature. In a subsequent step, the primer may be removed. After treatment with UDG, the region of the primer 5' to the uracil may be released (e.g., upon dilution, incubation, exposure to mild denaturing conditions, etc.) thereby exposing the complementary sequence as a single-stranded overhang. It should be appreciated that the length of the overhang may be determined by the position of the uracil on the amplifying primer and by the length of the amplifying primer. In some embodiments, mixture of Uracil DNA glycosylase (UDG) and the DNA glycosylase-lyase Endonuclease VIII, such as USER™ (Uracil-Specific Excision Reagent, New England Biolabs) is used. UDG catalyses the excision of a uracil base, forming an abasic site while leaving the phosphodiester backbone intact. The lyase activity of Endonuclease VIII breaks the phosphodiester backbone at the 3' and 5' sides of the abasic site so that base-free deoxyribose is released. In subsequent steps, the primer may be removed.

One should appreciate that the extension reactions can take place in a single volume that encompasses all of the utilized features comprising the support-bound oligonucleotides (1', 2', 3' and 4') or each step can take place in a localized individual microvolume that contains only the region(s) of interest to undergo a specific extension step. In some embodiments, the extension and/or assembly reactions are performed within a microdroplet (see PCT Application PCT/US2009/55267 and PCT Application PCT/US2010/055298, each of which is incorporate herein by reference in their entirety).

Primer extension may involve one or more suitable polymerase enzymes that can catalyze a template-based extension of a nucleic acid in a 5' to 3' direction in the presence of suitable nucleotides and an annealed template. A polymerase may be thermostable. A polymerase may be obtained from recombinant or natural sources. In some embodiments, a thermostable polymerase from a thermophilic organism may be used. In some embodiments, a polymerase may include a 3'→5' exonuclease/proofreading activity. In some embodiments, a polymerase may have no, or little, proofreading activity (e.g., a polymerase may be a recombinant variant of a natural polymerase that has been modified to reduce its proofreading activity). Examples of thermostable DNA polymerases include, but are not limited to: Taq (a heat-stable DNA polymerase from the bacterium *Thermus aquaticus*); Pfu (a thermophilic DNA polymerase with a 3'→5' exonuclease/proofreading activity from *Pyrococcus furiosus*, available from for example Promega); VENT® DNA Polymerase and VENT® (exo-) DNA Polymerase (thermophilic DNA polymerases with or without a 3'→5' exonuclease/proofreading activity from *Thermococcus litoralis*; also known as Th polymerase); Deep VENT® DNA Polymerase and Deep VENT® (exo-) DNA Polymerase (thermophilic DNA polymerases with or without a 3'→5' exonuclease/proofreading activity from Pyrococcus species GB-D; available from New England Biolabs); KOD HiFi (a recombinant *Thermococcus kodakaraensis* KODI DNA polymerase with a 3'→5' exonuclease/proofreading activity, available from Novagen); BIO-X-ACT (a mix of polymerases that possesses 5'-3' DNA polymerase activity and 3'→5' proofreading activity); Klenow Fragment (an N-terminal truncation of *E. coli* DNA Polymerase I which retains polymerase activity, but has lost the 5'→3' exonuclease activity, available from, for example, Promega and NEB); SEQUENASE™ (T7 DNA polymerase deficient in T-5' exonuclease activity); Phi29 (bacteriophage 29 DNA polymerase, may be used for rolling circle amplification, for example, in a TEMPLIPHI™ DNA Sequencing Template Amplification Kit, available from Amersham Biosciences); TopoTaq (a hybrid polymerase that combines hyperstable DNA binding domains and the DNA unlinking activity of *Methanopyrus topoisomerase*, with no exonuclease activity, available from Fidelity Systems); TopoTaq HiFi which incorporates a proofreading domain with exonuclease activity; PHUSION™ (a Pyrococcus-like enzyme with a processivity-enhancing domain, available from New England Biolabs); any other suitable DNA polymerase, or any combination of two or more thereof. In some embodiments, the polymerase can be a SDP (strand-displacing polymerase; e.g, an SDPe-which is an SDP with no exonuclease activity). This allows isothermal PCR (isothermal extension, isothermal amplification) at a uniform temperature. As the polymerase (for example, Phi29, Bst) travels along a template it displaces the complementary strand (e.g., created in previous extension reactions). As the displaced DNAs are single-stranded, primers can bind at a consistent temperature, removing the need for any thermocycling during amplification.

In some embodiments, after extension or amplification, the polymerase may be deactivated to prevent interference with the subsequent steps. A heating step (e.g., high temperature) can denature and deactivate most enzymes which are not thermally stable. Enzymes may be deactivated in presence or in the absence of liquid. Heat deactivation on a dry support may have the advantage to deactivate the enzymes without any detrimental effect on the oligonucleotides. In some embodiments, a non-thermal stable version of the thermally stable PCR DNA Polymerase may be used, although the enzyme is less optimized for error rate and speed. Alternatively, Epoxy dATP can be use to inactivate the enzyme.

In one embodiment, a support is provided that comprises at least one feature having a plurality of surface-bound single-stranded oligonucleotides. Each of the plurality of oligonucleotides is bound to a discrete feature of the support, and the predefined sequence of each plurality of oligonucleotides attached to the feature is different from the predefined sequence of the oligonucleotides attached to a different feature. At least one plurality of oligonucleotides is synthesized in a chain extension reaction on a first feature of the support by template-dependent synthesis. In some embodiments, the entire support or array containing the discrete features is subjected to thermocycling, annealing temperature conditions, stringent melt temperature conditions, or denaturing temperature conditions. Heating and cooling the support can be performed in any thermal cycle instrument. In other embodiments, one or more discrete features are subjected to specific temperature conditions (annealing, extension, wash or melt). Thermocycling of selected independent features (being separated from each others) can be performed by locally heating at least one discrete feature. Discrete features may be locally heated by any means known in the art. For example, the discrete features may be locally heated using a laser source of energy that can be controlled in a precise x-y dimension thereby individually modulating the temperature of a droplet. In another example, the combination of a broader beam laser with a mask can be used to irradiate specific features. In some embodiments, methods to control temperature on the support so that enzymatic reactions can take place on a support (PCR, ligation or any other temperature sensitive reaction) are provided. In some embodiments, a scanning laser is used to control the thermocycling on distinct features on the solid support. The wavelength used can be chosen from wide spectrum (100 nm to 100,000 nm, i.e., from ultraviolet to infrared). In some embodiments, the features comprising the oligonucleotides comprise an optical absorber or indicator. In some embodiments, the solid support is cooled by circulation of air or fluid. The energy to be deposited can be calculated based on the absorbance behavior. In some embodiments, the temperature of the droplet can be modeled using thermodynamics. The temperature can be measured by an LCD like material or any other in-situ technology. Yet in another embodiment, the whole support can be heated and cooled down to allow enzymatic reactions or other temperature sensitive reactions to take place. In some embodiments, an energy source can be directed by a scanning setup to deposit energy at various locations on the surface of the solid support comprising support-bound molecules. Optical absorbent material can be added on the surface of the solid support. Optical energy source, such as a high intensity lamp, laser, or other electromagnetic energy source (including microwave) can be used. The temperature of the different reaction sites can be controlled independently by controlling the energy deposited at each of the features.

For example, a Digital Micromirror Device (DMD) can be used for temperature control. DMD is an microfabricated spatial optical modulator. See, for example, U.S. Pat. No. 7,498,176. In some embodiments, a DMD can be used to precisely heat selected spots or droplets on the solid support. The DMD can be a chip having on its surface, for example, several hundred thousand to several million microscopic mirrors arranged in a array which correspond to the spots or droplets to be heated. The mirrors can be individually rotated (e.g.,)±10-12°), to an on or off state. In the on state, light from a light source (e.g., a bulb) is reflected onto the solid support to heat the selected spots or droplets. In the off state, the light is directed elsewhere (e.g., onto a heatsink). In some embodiments, the array may be a rectangular array. In one example, the DMD can consist of a 1024×768 array of 16 µm wide micromirrors. In another example, the DMD can consist of a 1920×1080 array of 10 µm wide micromirrors. Other arrangements of array sizes and micromirror widths are also possible. These mirrors can be individually addressable and can be used to create any given pattern or arrangement in heating different spots on the solid support. The spots can also be heated to different temperatures, e.g., by providing different wavelength for individual spots, and/or controlling time of irradiation. In certain embodiments, the DMD can direct light to selected spots and used to identify, select, melt, and/or cleave any oligonucleotide of choice.

FIGS. 1a-1e show an exemplary method for producing polynucleotide having a predetermined sequence on a substrate or solid support. In some embodiments, polynucleotides may be assembled to synthesize the final nucleic acid sequence (e.g. target nucleic acid). Referring to FIG. 1a, a nucleic acid array 10 is shown possessing an arrangement of features 20 in which each feature comprises a plurality of support-bound single-stranded oligonucleotides 30. Preferably, support-bound oligonucleotides are attached through their 3' end. In some embodiments, support-bound single-stranded oligonucleotides are about 20 nucleotides long, about 40 nucleotides long, about 50 nucleotides long, about 60 nucleotides long, about 70 nucleotides long, about 80 nucleotides long, about 100 nucleotides long or more. In some embodiments, the oligonucleotides 30 further comprise a universal priming site at the 3' end (e.g. 15 bases primer binding site at the 3' end) and a sequence complementary to a construction oligonucleotide (also referred as building block, and designated as 1', 2', 3' etc.). In some embodiments, the construction oligonucleotides are contiguous one with another and together make up or span the sequence of the target polynucleotide. In preferred embodiments, the construction oligonucleotides span the entire sequence of the target polynucleotide without any gaps. Yet in other embodiments, the construction oligonucleotides are partially overlapping resulting in gaps between construction oligonucleotides when hybridized to each other. Referring to FIG. 1a, the target polynucleotide is assembled from a population of construction oligonucleotides, the even numbered construction oligonucleotides representing one strand of the double-stranded target polynucleotide (e.g. plus strand) and the uneven numbers representing a complementary strand of the double-stranded target polynucleotide (e.g. minus strand). Preferably, the pool of construction oligonucleotides comprises construction oligonucleotides having overlapping sequences so that construction oligonucleotides can hybridize to one another under the appropriate hybridization conditions. One would appreciate that each internal construction oligonucleotide will hybridize to two different construction oligonucleotides whereas the construction oligonucleotides at the 5' and/or 3' terminus will hybridize each to a different (or the same) internal oligonucleotide(s). Hybridization of the overlapping construction oligonucleotides will therefore result in a target polynucleotide having a 3' and/or a 5' overhang. Yet in some embodiments, the resulting target polynucleotide may comprise blunt end at its 5' or/and 3' terminus. The construction oligonucleotides may subsequently be ligated to form a covalently linked double-stranded nucleic acid construct (FIG. 1d) using ligation assembly techniques known in the art.

Referring to FIG. 1b, at least one feature on support 10 comprising the support-bound oligonucleotides is incubated with a primer 50. In a first step, the primer is first annealed to the immobilized single-stranded oligonucleotide and extended in presence of appropriate polymerase and dNTPs, under appropriate extension conditions, to form construction oligonucleotides 60 (designated as 1, 2, 3, 4) which are complimentary to the support-bound oligonucleotides (1', 2' 3', 4'). In some embodiments, the primer is a primer containing multiple Uracil (U). In a subsequent step, the primer is removed. Preferably, an USER™ endonuclease is added to digest the primer. Digestion of the primers may take place subsequent to the extension step, thereby generating a duplex comprising the construction oligonucleotides hybridized to the support-bound oligonucleotides (e.g. 1-1', 2-2' etc....). Yet in other embodiments, digestion of the primers occurs in solution after release of the construction oligonucleotides in solution (FIG. 1c).

In a second step (FIG. 1c), the newly synthesized extension products (construction oligonucleotides 65: 1, 2, 3, and/or 4) are melted and released from the support 10. Dissociation may be performed in parallel or sequentially. The construction oligonucleotides may be released in solution. In one embodiment, the solution is a buffer comprising 10 mM Tris, 50 mM sodium chloride, and 1 mM EDTA. Melting of the duplex may be performed by increasing the temperature, for example, at specific location on the array, to a melting temperature (e.g. 95° C.). Alternatively, the duplex may be dissociated by addition of an enzyme capable to separate the double-stranded nucleic acids. Helicase enzyme may be added at specific location on the array. Helicase enzymes are known in the art and have been shown to unwind DNA from a double-stranded structure to a single-stranded structure. The single-stranded extension product can be transferred to a second support 15 comprising a first plurality of anchor support-bound oligonucleotides, the first plurality of anchor oligonucleotide sequence comprising a sequence partially complementary to a first extension product (e.g. construction oligonucleotide 1). The first extension product is allowed to hybridize under appropriate conditions to the first plurality of anchor oligonucleotides. During the same reaction or subsequently, the other extension products (or overlapping construction oligonucleotides) are allowed to hybridize under the appropriate conditions to their complementary sequences, thereby forming a longer polynucleotide sequence.

Referring to FIG. 1d, construction oligonucleotides 65 can be transferred to a new surface 15 comprising an anchor support-bound oligonucleotide 40 having a sequence complementary to the first construction oligonucleotide (construction oligonucleotide 1). Additional construction oligonucleotides (construction oligonucleotides 2, 3, 4 etc) are designed to hybridize to each other through their overlapping regions, as shown, to form a longer nucleic acid construct 70. In some embodiments, the anchor support-bound oligonucleotide is preferably single-stranded. In some embodiments, the anchor support-bound oligonucleotide comprises a 5' terminus complementary to the 5' terminus of a first plurality of oligonucleotides. The additional construction oligonucleotides that together form the polynucleotide sequence comprise complementary 3' termini and hybridize to each others. The inset, FIG. 1d, shows an example of oligonucleotides that have been designed to hybridize to each other to assemble into a longer polynucleotide construct built onto anchor oligonucleotide 40. Ligase 80 is introduced into solution to ligate each junction thus forming a covalently joined longer polynucleotide construct 90 as shown in FIG. 1e. If desired the last oligonucleotide in the assembly (e.g. construction oligonucleotide 4) may be labeled with a fluorescent label so as to indicate that a full length construction has taken place.

In certain exemplary embodiments, a detectable label can be used to detect one or more oligonucleotides or polynucleotides described herein. Examples of detectable markers include various radioactive moieties, enzymes, prosthetic groups, fluorescent markers, luminescent markers, bioluminescent markers, metal particles, protein-protein binding pairs, protein-antibody binding pairs and the like. Examples of fluorescent proteins include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride, phycoerythrin and the like. Examples of bioluminescent markers include, but are not limited to, luciferase (e.g., bacterial, firefly, click beetle and the like), luciferin, aequorin and the like. Examples of enzyme systems having visually detectable signals include, but are not limited to, galactosidases, glucorimidases, phosphatases, peroxidases, cholinesterases and the like. Identifiable markers also include radioactive compounds such as 125I, 35S, 14C, or 3H. Identifiable markers are commercially available from a variety of sources.

Figure 2:
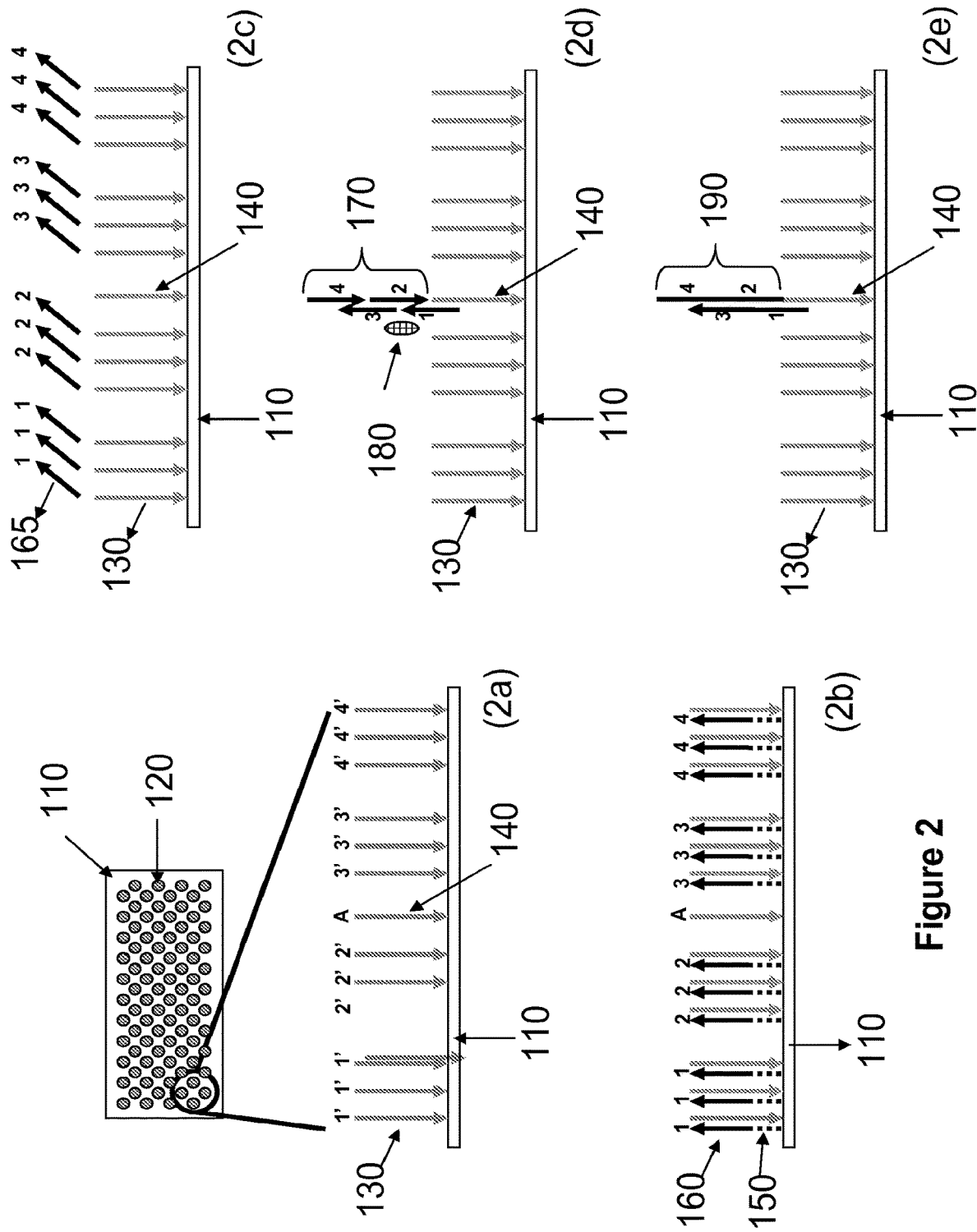
FIG. 2 illustrates a non-limiting exemplary method of surface attached nucleic acid synthesis using a single surface comprising oligonucleotide generating sequences and anchor sequences.

In some embodiments, the support comprises a set of features comprising support-bound oligonucleotides complementary to construction oligonucleotides and at least one feature comprising an anchor support-bound oligonucleotide. The anchor oligonucleotide is preferably single-stranded and comprises a sequence complementary to a terminus sequence of the target polynucleotide. Referring to FIG. 2a, an oligonucleotide array 110 is shown which is similar that described in FIG. 1a, except that the support comprises on the same surface, support-bound oligonucleotides 130, and support-bound anchor oligonucleotides 140.

Referring to FIG. 2b, a primer 150 is hybridized to the support-bound oligonucleotides 130 under hybridizing conditions. In a first step, the primer is annealed to a support-bound single-stranded oligonucleotide and extended with the addition of dNTPs and an appropriate polymerase under appropriate conditions and temperature, to form construction oligonucleotides 160 (construction oligonucleotides 1, 2, 3, 4) which are complimentary to the support-bound oligonucleotides (1', 2' 3', 4'). In some embodiments, the primer is a primer containing multiple uracil (U). In a subsequent step, the primer is removed. Preferably, an USER™ endonuclease is added to digest the primer. Digestion of the primers may take place subsequent to the extension step, thereby generating a duplex comprising the construction oligonucleotides hybridized to the support-bound oligonucleotides. Yet in other embodiments, digestion of the primers occurs in solution after release of the construction oligonucleotides in solution (165, FIG. 2c).

In a second step (FIG. 2c), the newly synthesized extension products (construction oligonucleotide 1, 2, 3, and/or 4) are melted and released from the features (construction oligonucleotide 165). Dissociation of the construction oligonucleotides can be performed in parallel or sequentially. The construction oligonucleotides 165 may be released in solution. Melting of the duplexes may be performed by increasing the temperature to a melting temperature (e.g. 95° C.). Alternatively, the duplexes may be dissociated using an enzyme capable of dissociating the double-stranded nucleic acids, such as an helicase. The first extension product is allowed to hybridize under appropriate conditions to the first plurality of anchor oligonucleotides and the other extension products (or overlapping oligonucleotides) are allowed to hybridize under appropriate conditions to their complementary sequences.

Referring to FIG. 2d, construction oligonucleotides (165) are hybridized to an anchor support-bound oligonucleotide 140 having a sequence complementary to the first construction oligonucleotide (construction oligonucleotide 1). Additional construction oligonucleotides (2, 3, 4 etc.) are designed to hybridize to each other through their overlapping regions, as shown in FIG. 2d, to form a longer nucleic acid construct 170. In preferred embodiments, the anchor support-bound oligonucleotide is single-stranded. In some embodiments, the anchor support-bound oligonucleotide comprises a 5' terminus complementary to the 5' terminus of a first plurality of oligonucleotides. The additional construction oligonucleotides that together form the polynucleotide sequence comprise complementary 3' termini and hybridize to each other. FIG. 2d, shows an example of oligonucleotides that have been designed to hybridize to each other to assemble into a longer polynucleotide construct built onto anchor oligonucleotide 140. Ligase 180 is introduced into solution to covalently ligate each junction thus forming a covalently joined longer polynucleotide construct 190 as shown in FIG. 2e. If desired the last oligonucleotide in the assembly (construction oligonucleotide 4) may be labeled with a fluorescent label so as to indicate that a full length construction has taken place.

Aspects of the invention relate to the selection of target polynucleotides having the predefined sequence and/or to the removal of undesired assembly products. During polynucleotides assembly from oligonucleotides, undesired products such as partial length polynucleotides, truncated constructs can be assembled. It can be useful to remove undesired products or polynucleotides that do not have the correct sequence and/or length. In some embodiments, one or more assembled polynucleotides may be sequenced to determine whether they contain the predetermined sequence or not. This procedure allows fragments with the correct sequence to be identified. In other embodiments, other techniques known in the art may be used to remove error containing nucleic acid fragments.

Figure 3:
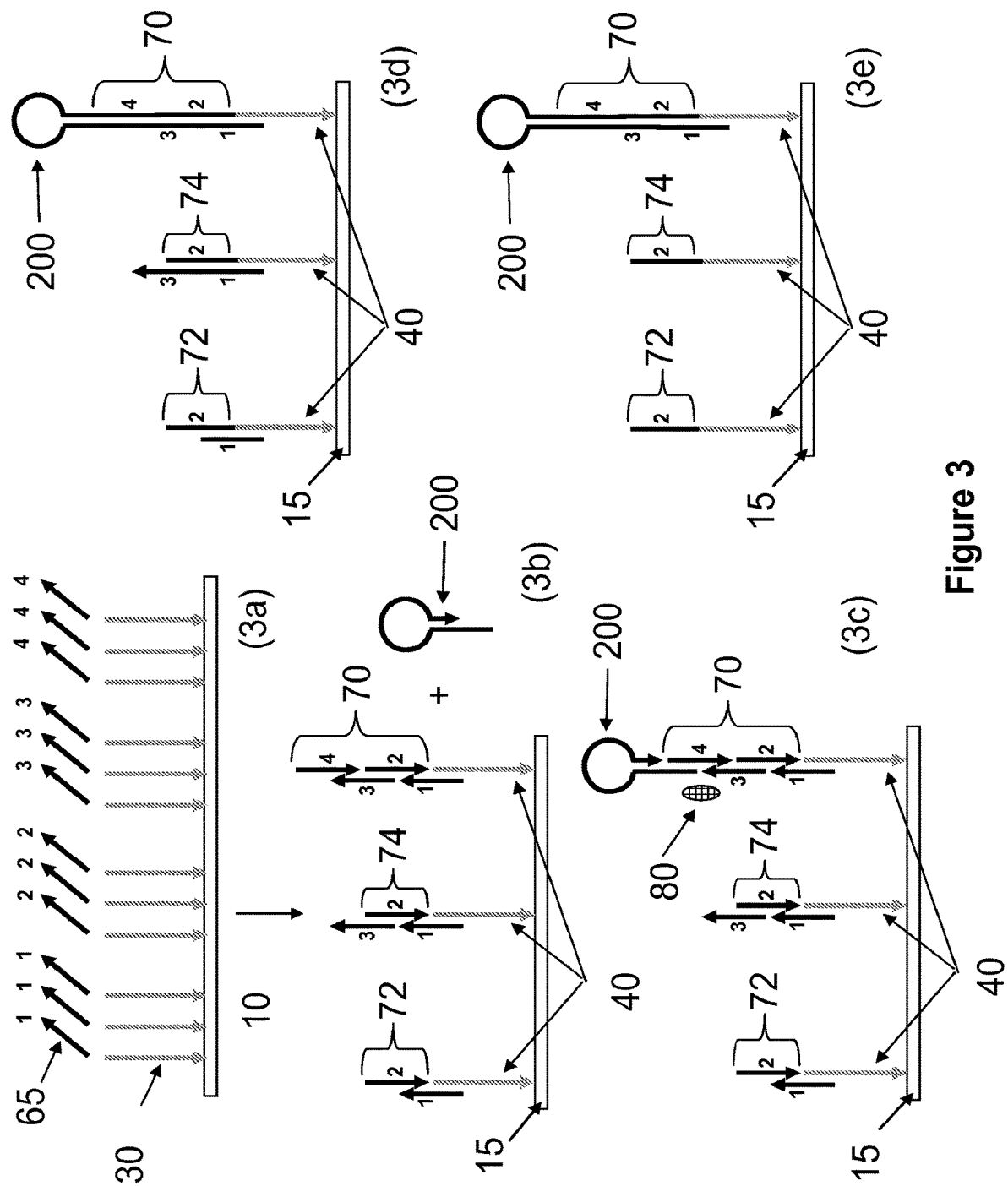
FIG. 3 illustrates a non-limiting exemplary method of surface attached nucleic acid synthesis and screening for full length assembled polynucleotides using a single-strand specific exonuclease.

In some aspects of the invention, methods are provided for selectively protecting target polynucleotide sequences from exonuclease digestion thereby facilitating the elimination of undesired constructs. Any of a variety of nucleases that preferably digest single-stranded nucleic acids can be used. Suitable nucleases include, for example, a single-strand specific 3' exonuclease, a single-strand specific endonuclease, a single-strand specific 5' exonuclease, and the like. In certain embodiments, the nuclease comprises E. coli Exonuclease I. In some embodiments, the exonuclease digestion is performed to digest all non-double-stranded sequences. Selection methods are illustrated in FIGS. 3a-3e. In one embodiment, the selection method takes advantage of the terminus 3' or 5' overhang of the fully assembled product. One will appreciate that the single-stranded overhanging sequence (5' or 3') of the fully assembled product will correspond to the sequence of the terminal oligonucleotide (for example construction oligonucleotide 4, as depicted in FIG. 3b). In undesired products, the single stranded 3' or 5' overhang sequence will have a sequence different from the predefined terminal oligonucleotide. For example, as depicted in FIGS. 3a-3e, the undesired products have a free overhang having construction oligonucleotide 2, or 3 instead of terminal construction oligonucleotide 4. As used herein the term "terminal oligonucleotide" or "terminal construction oligonucleotide" refers to the oligonucleotide at the target polynucleotide terminal sequence or terminal overhang. In some embodiments, the terminal oligonucleotide corresponds to the 3' or the 5' single-stranded overhang of the target polynucleotide. In some embodiments, the target polynucleotide sequence comprises at least a first oligonucleotide, and a terminal construction oligonucleotide, wherein the terminal oligonucleotide is downstream from the first oligonucleotide. In some embodiments, the target polynucleotide comprises a first oligonucleotide, a terminal oligonucleotide and at least one internal oligonucleotide.

FIGS. 3a-3c illustrates the case wherein truncated or undesired assemblies (72, and 74, FIG. 3b) are generated as well as full length assemblies (70, FIG. 3b). In order to filter out the undesired assemblies, a nucleic acid hairpin structure or stem-loop oligonucleotide 200 can be added to the assembly product. The stem-loop oligonucleotide is designed to hybridize to 5' or the 3' overhang and ligate to the two terminal oligonucleotides present in the full length assembly product 70. In addition, the stem-loop oligonucleotide is designed not to hybridize or ligate to truncation products 72 and 74.

The stem-loop structure may be formed by designing the oligonucleotides to have complementary sequences within its single-stranded sequence whereby the single-strand folds back upon itself to form a double-stranded stem and a single-stranded loop. Preferably, the double-stranded stem domain has at least about 2 base pairs and the single stranded loop has at least 3 nucleotides. Preferably, the stem comprises an overhanging single-stranded region (3' or 5'), i.e., the stem is a partial duplex. For example, the overhang length can be from about 3 to about 10, to about 20, to about 50, etc. . . . nucleotides. In an exemplary embodiment, the overhang length of the stem-loop oligonucleotide is complementary to the 5' or 3' single-stranded overhang of the fully assembled polynucleotide or target polynucleotide.

Referring to FIG. 3d, the stem-loop oligonucleotide is ligated to the full length polynucleotide having the predefined sequence. Referring to FIG. 3e, the support surface is exposed to an exonuclease such as a 3' nuclease. In preferred embodiments, the stem-loop oligonucleotide serves to protect the overhang (3' or 5' overhang) of the full length polynucleotide construct 70. The undesired constructs (e.g. truncated constructs) which did not hybridize/ligate to the stem-loop oligonucleotides are susceptible to digestion. After the digestion step (FIG. 3e), the stem-loop oligonucleotide may be cleaved off the full length construct. For example, in some embodiments, the stem-loop oligonucleotide is designed to comprise a type II restriction site into the stem structure of the stem-loop oligonucleotide and the stem-loop oligonucleotide is cleaved off the nucleic acid construct restriction enzyme (e.g. type II restriction enzyme). In other embodiments, the stem-loop oligonucleotide is designed to comprise at least one Uracil and the stem-loop oligonucleotide is cleaved off the nucleic acid construct using a mixture of Uracil DNA glycosylase (UDG) and a DNA glycosylase-lyase Endonuclease VIII or a USER™ enzyme. In some embodiments, the full length polynucleotide may be cleaved off the surface. In some embodiments, necessary restriction sites can be specifically included in the design of the first plurality of oligonucleotide and/or in the design of the anchor oligonucleotides. In some embodiments, the restriction site is a type II restriction site. In some embodiments, the full length construct may be subsequently amplified.

In some embodiments, the 3' region of the anchor oligonucleotide comprises a restriction enzyme site. In some embodiments, primers/primer binding sites may be designed to include a restriction endonuclease cleavage site. In an exemplary embodiment, a primer/primer binding site contains a binding and/or cleavage site for a type IIs restriction endonuclease. A wide variety of restriction endonucleases having specific binding and/or cleavage sites are commercially available, for example, from New England Biolabs (Beverly, Mass.). In various embodiments, restriction endonucleases that produce 3' overhangs, 5' overhangs or blunt ends may be used. When using a restriction endonuclease that produces an overhang, an exonuclease (e.g., RecJ$_f$, Exonuclease I, Exonuclease T, S$_1$ nuclease, P$_1$ nuclease, mung bean nuclease, T4 DNA polymerase, CEL I nuclease, etc.) may be used to produce blunt ends. Alternatively, the sticky ends formed by the specific restriction endonuclease may be used to facilitate assembly of subassemblies in a desired arrangement. In an exemplary embodiment, a primer/primer binding site that contains a binding and/or cleavage site for a type IIs restriction endonuclease may be used to remove the temporary primer. The term "type-IIs restriction endonuclease" refers to a restriction endonuclease having a non-palindromic recognition sequence and a cleavage site that occurs outside of the recognition site (e.g., from 0 to about 20 nucleotides distal to the recognition site). Type IIs restriction endonucleases may create a nick in a double-stranded nucleic acid molecule or may create a double-stranded break that produces either blunt or sticky ends (e.g., either 5' or 3' overhangs). Examples of Type IIs endonucleases include, for example, enzymes that produce a 3' overhang, such as, for example, Bsr I, Bsm I, BstF5 I, BsrD I, Bts I, Mnl I, BciV I, Hph I, Mbo II, Eci I, Acu I, Bpm I, Mme I, BsaX I, Bcg I, Bae I, Bfi I, TspDT I, TspGW I, Taq II, Eco57 I, Eco57M I, Gsu I, Ppi I, and Psr I; enzymes that produce a 5' overhang such as, for example, BsmA I, Ple I, Fau I, Sap I, BspM I, SfaN I, Hga I, Bvb I, Fok I, BceA I, BsmF I, Ksp632 I, Eco31 I, Esp3 I, Aar I; and enzymes that produce a blunt end, such as, for example, Mly I and Btr I. Type-IIs endonucleases are commercially available and are well known in the art (New England Biolabs, Beverly, Mass.).

In other embodiments, the primer and/or primer biding sites comprises at least on Uracil and the primer is cleaved off using a mixture of Uracil DNA glycosylase (UDG) and a DNA glycosylase-lyase Endonuclease VIII or a USER™ enzyme as provided t.

Figure 4:
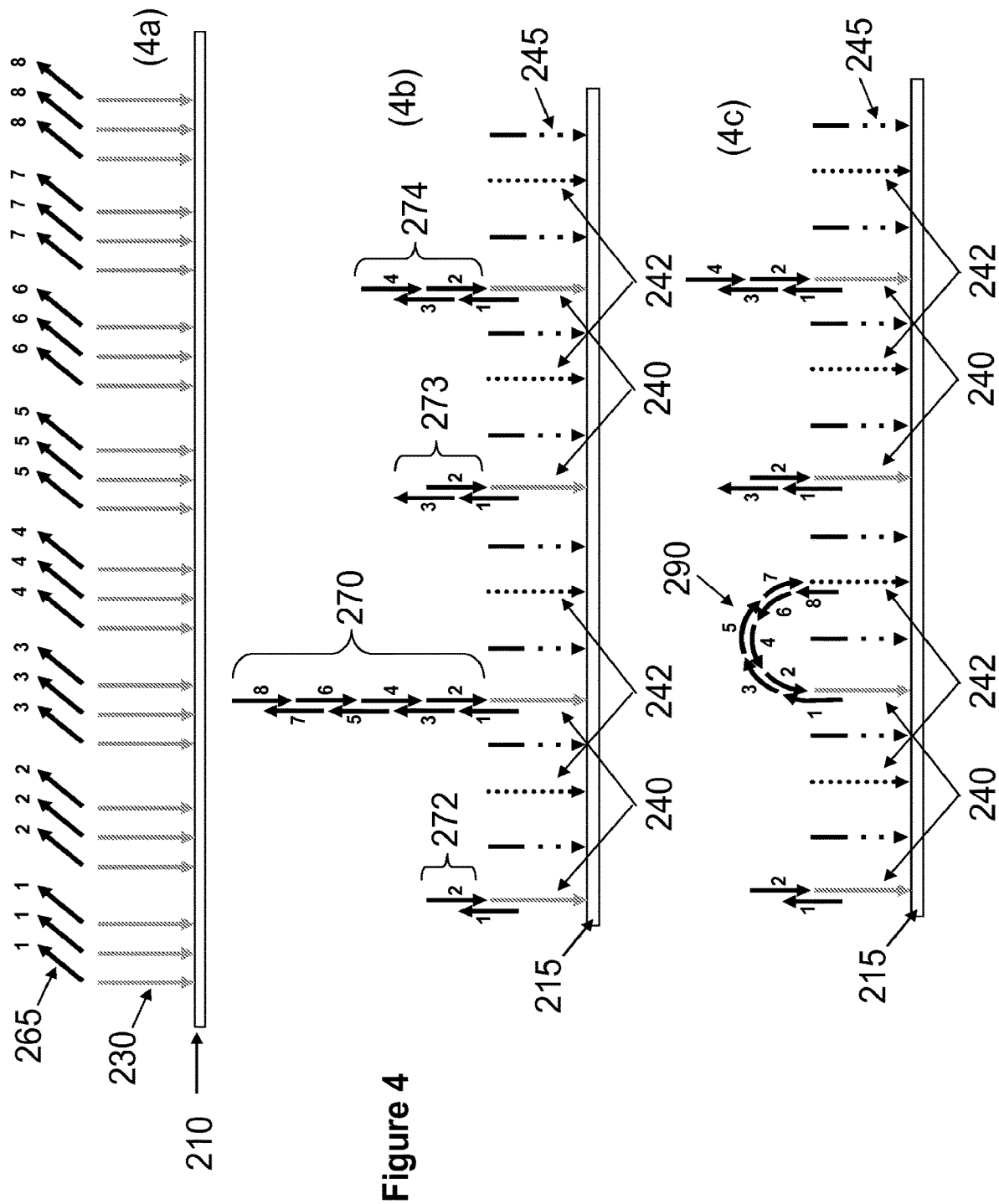
FIG. 4 illustrates a non-limiting exemplary method of surface attached nucleic acid synthesis and screening for full length assembled polynucleotides using a molecular ruler.

In some other embodiments, selection of target polynucleotides takes advantage of the size or length of the desired target polynucleotide. FIGS. 4a-4c illustrates methods for measuring the length of a polynucleotide construct(s) on an array's surface and for selecting full length polynucleotide construct(s). Preferably, the methods allow for the selection of the correct length target polynucleotide construct from amongst a distribution of different polynucleotide construct lengths. One skilled in the art would appreciate that attachment chemistries for nucleic acids to glass surfaces typically result in nucleic acids molecule to molecule spacing (d) ranging from 1 to 15 nm, preferably from 2 to 8 nm, preferably from 5 to 7 nm. In some embodiments, distance d is about 6 nm. Referring to FIG. 4b, a surface 215 may be prepared which has a first plurality of anchor oligonucleotides 240 and a second plurality of anchor oligonucleotides 242 immobilized on the support wherein the first and second pluralities of anchor oligonucleotides have a different predefined sequence. In some embodiments, the first and second pluralities of anchor oligonucleotides are separated by a predetermined distance X. In some embodiments, the distance X may be set and controlled by mixing in equal numbers of first and second anchor molecules with a third support-bound oligonucleotide sequence referred as a spacer oligonucleotide sequence 245. In some embodiments, the spacer oligonucleotide sequence is designed not to have complementary sequences with the construction oligonucleotides. In some embodiments, the spacer oligonucleotide is single-stranded. Yet, in other embodiments, the spacer oligonucleotide is double-stranded. In some embodiments, the distance X is set using the following equation:

$$X \sim d \times (C[spacer]/C[anchor1+anchor2])$$

wherein d is the distance between two nucleic acid molecules, C[spacer] is the concentration of the spacer oligonucleotide, C[anchor1+anchor2] is the concentration of a mixture of anchor oligonucleotide 1 and anchor oligonucleotide 2.

Referring to FIG. 4a, construction oligonucleotides 265 are synthesized by primer extension using support-bound oligonucleotides 230 as templates. In some embodiments, a first support-bound anchor oligonucleotide 240 is designed to have a sequence complementary to a first plurality of construction oligonucleotides. Construction oligonucleotides 265 may hybridize to each other and hybridize to the anchor oligonucleotide thereby generating support-bound polynucleotide constructs (270, 272, 273, 274, FIG. 4b). After assembly reactions, some of these polynucleotide constructs (270) may be full length polynucleotides having the predefined sequence, whereas other polynucleotide constructs (272, 273, 274) may be shorter than full length polynucleotide constructs. Taking into account that the nucleotides in a nucleic acid construct are spaced about 0.33 nm or 0.34 nm apart, a nucleic acid construct comprising 1000 nucleotide bases (as per a typical gene length) will be about 340 nm in length. In some embodiments, a second support-bound anchor oligonucleotide 242 may be designed so that it can connect to the terminus or 5' overhang of the full length DNA construct 270, resulting in bound full length construct 290. Furthermore if the distance X is set to be approximately the length expected of the full length construct then the terminus or 5'-overhang of the full length construct should only bind to the second anchor oligonucleotide if a) the full length construct has the correct sequence at the end, and if b) the full length construct has the correct length (290, as shown in FIG. 4c). In some embodiments, the first anchor 240 may comprise a type II endonuclease site. The full length product may be cleaved using type II restriction endonuclease resulting in a product that is anchored at the distal end to the second anchor 242. In some embodiments, the anchor sequence comprises at least one Uracil and the full length product is cleaved using a mixture of Uracil DNA glycosylase (UDG) and a DNA glycosylase-lyase Endonuclease VIII or a USER™ enzyme.

Figure 5:
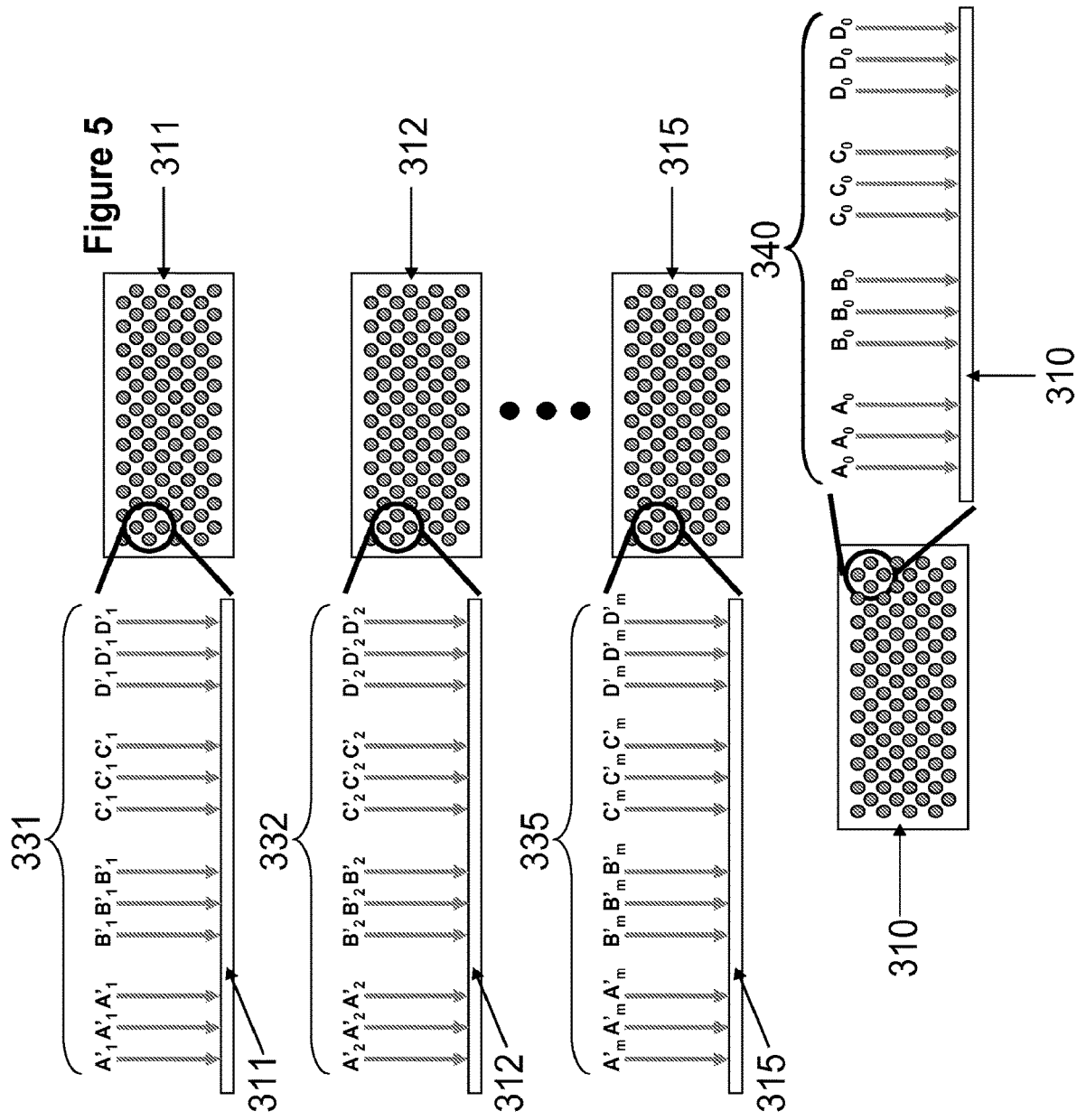
FIG. 5 illustrates non-limiting exemplary construction arrays and anchor array comprising support-bound oligonucleotides.

Some aspects of the invention relate to devices and methods enabling highly parallel support-bound oligonucleotides assembly. In some embodiments, an array of polynucleotides may be assembled on a surface by sequential addition of complementary overlapping oligonucleotides to a plurality of anchor oligonucleotides. In preferred embodiments, a plurality of polynucleotides having different predetermined sequences are synthesized at different features of an array. Referring to FIG. 5, an anchor array 310 is provided wherein each feature of the array comprises a support-bound anchor oligonucleotide (340: $A_0$, $B_0$, $C_0$, $D_0$) as described above. Each anchor oligonucleotide may be single-stranded and may comprise at its 5' terminal a sequence complementary to the 5' terminus of a first plurality of oligonucleotides. One should appreciate that, for highly parallel synthesis of different polynucleotides, each plurality of anchor oligonucleotides at each feature needs to have a sequence complementary to the 5' end of the predetermined polynucleotide sequence to be synthesized. Accordingly, in some embodiments, the anchor array comprises different populations of anchor oligonucleotides at different features of the array, each population or plurality of anchor oligonucleotides having a different 5' terminal sequence. Additionally, two or more construction arrays (311, 312, and 315) can be provided, wherein the construction arrays comprise a plurality of features, each feature comprising a different population of support-bound oligonucleotides ($A_n$, $B_n$, $C_n$, $D_n$) having a predefined sequence. It should be appreciated that, in some embodiments, each feature comprises a plurality of support-bound oligonucleotides having a pre-determined sequence different than the sequence of the plurality of support-bound oligonucleotides from another feature on the same surface. The oligonucleotide sequences can differ by one or more bases. Referring FIG. 5, the first array 311 comprises a first plurality of support-bound oligonucleotides 331 ($A_1'$, $B_1'$, $C_1'$, $D_1'$), wherein part of the sequence of each of the first plurality oligonucleotides is identical to the 5' end of the anchor oligonucleotides 340 attached to a feature of the anchor array. The second array 312 comprises a second plurality of support-bound oligonucleotides 332 ($A_2'$, $B_2'$ $C_2'$ $D_2'$), wherein the 5' end of each of the second plurality of oligonucleotides is complementary to 5' end of a first plurality of oligonucleotides 331. One should appreciate that depending on the polynucleotides' sequence and the length to be assembled, one or more (for example, m) additional arrays may be provided, each array comprising a plurality of support-bound oligonucleotides ($A'_{m-1}$, $B'_{m-1}$, $C'_{m-1}$, $D'_{m-1}$) having a free 5' end complementary to the 5' end of another plurality of support-bound oligonucleotides 335 ($A'_m$, $B'_m$, $C'_m$, $D'_m$). In some embodiments, each plurality of complementary oligonucleotides is provided on a different support.

Figure 6:
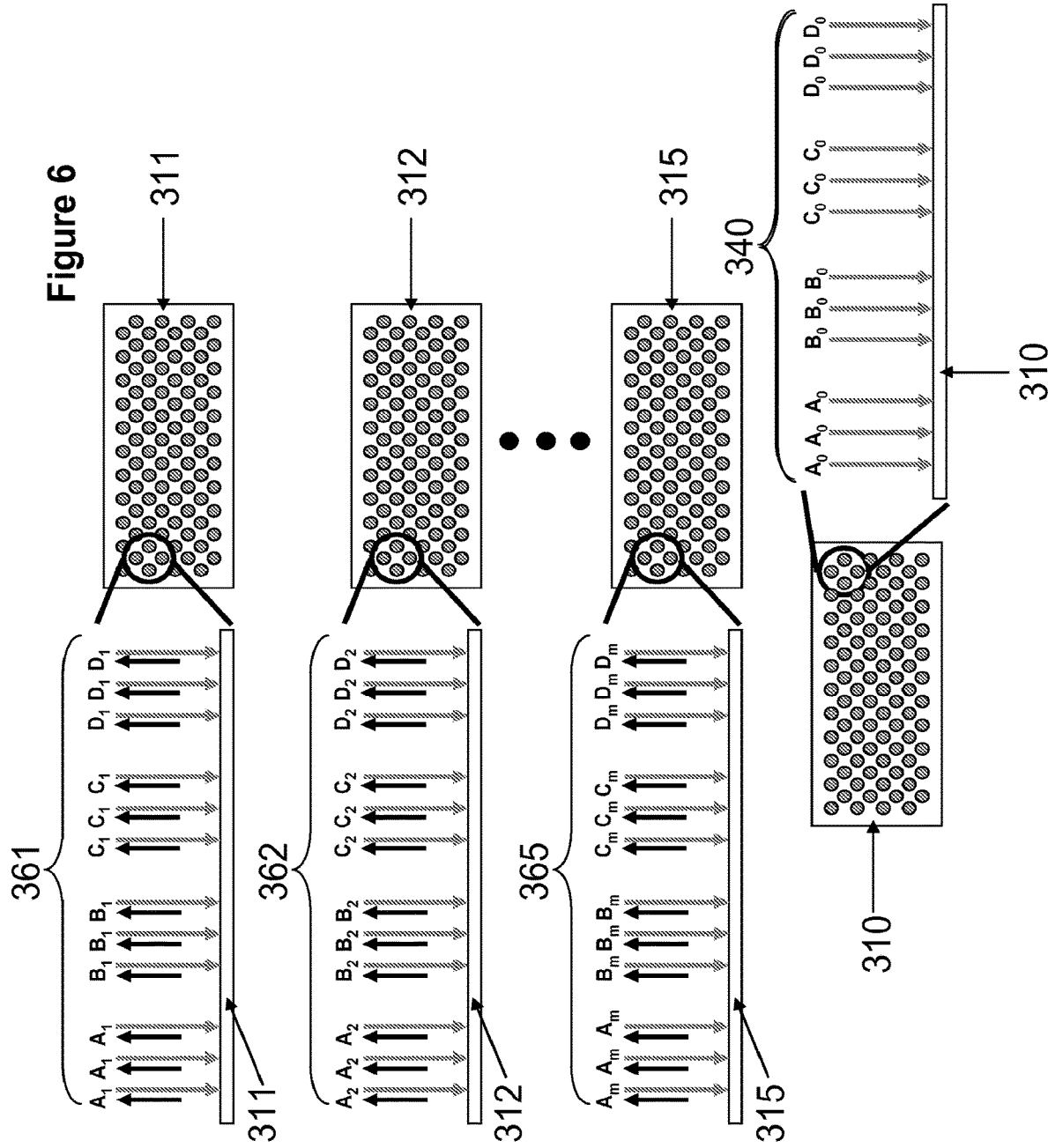
FIG. 6 illustrates a non-limiting method for the synthesis of construction oligonucleotides from support-bound oligonucleotides immobilized on construction arrays.

Referring to FIG. 6, a first plurality of complementary oligonucleotides (construction oligonucleotides $A_1$, $B_1$, $C_1$, $D_1$) are generated using the first plurality of support-bound oligonucleotides 331 ($A_1'$, $B_1'$, $C_1'$, $D_1'$) as templates. In some embodiments, one or more support-bound oligonucleotides are incubated with a primer in presence of a polymerase under conditions promoting primer extension. In some embodiments, the first plurality of support-bound oligonucleotides 331 ($A_1'$, $B_1'$, $C_1'$, $D_1'$) has at its 3' end a sequence designed to be complementary to the primer sequence (e.g. primer binding site). In some embodiments, the primer is a primer containing multiple uracil and after extension the primer is removed using an USER™ endonuclease as described herein. Similarly, construction oligonucleotides $A_2$, $B_2$, $C_2$, $D_2$ and $A_m$, $B_m$, $C_m$, $D_m$ can be synthesized in a parallel or sequential fashion, thereby generating support-bound double-stranded oligonucleotides (e.g. 361: $A_1 A_1'$, etc. . . . ).

Figure 7A:
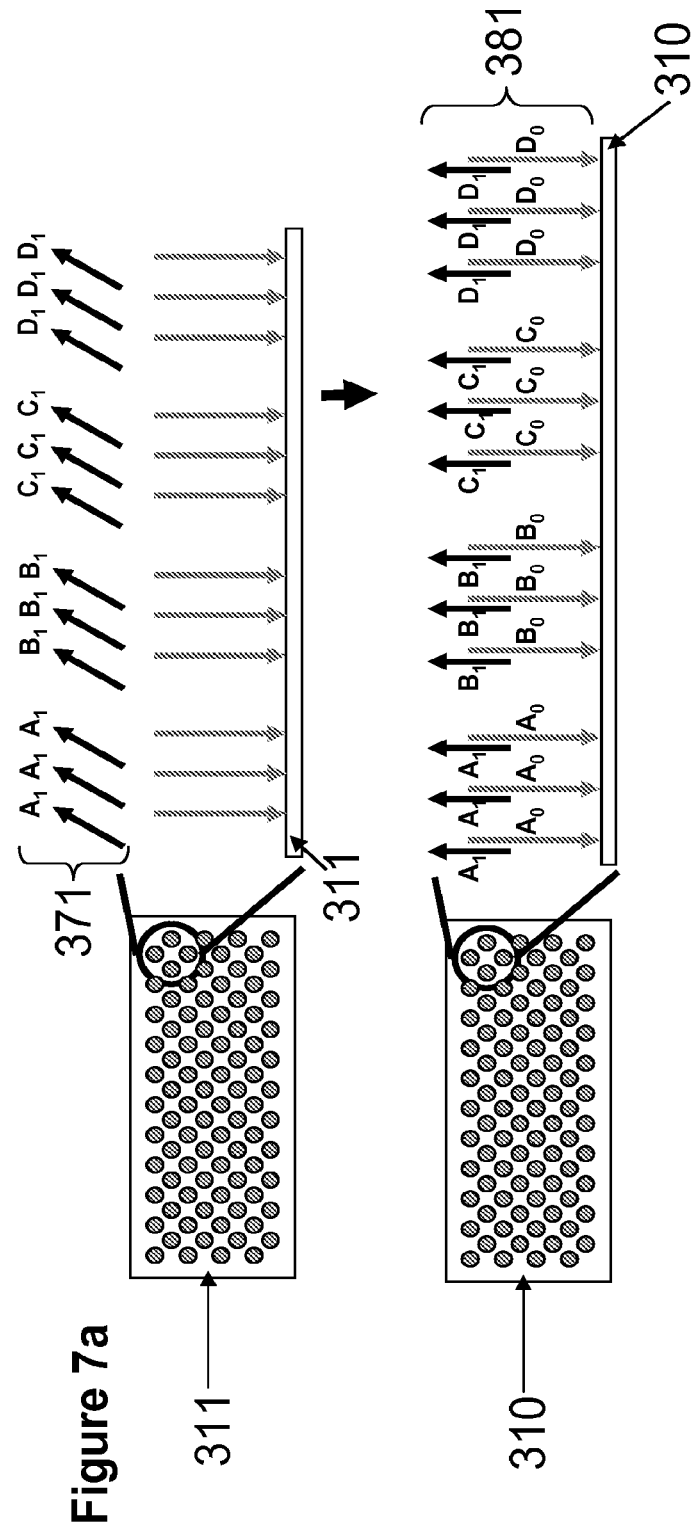
FIG. 7a-7b illustrates a non-limiting method for highly parallel sequential surface-attached polynucleotide synthesis.
Figure 7B:
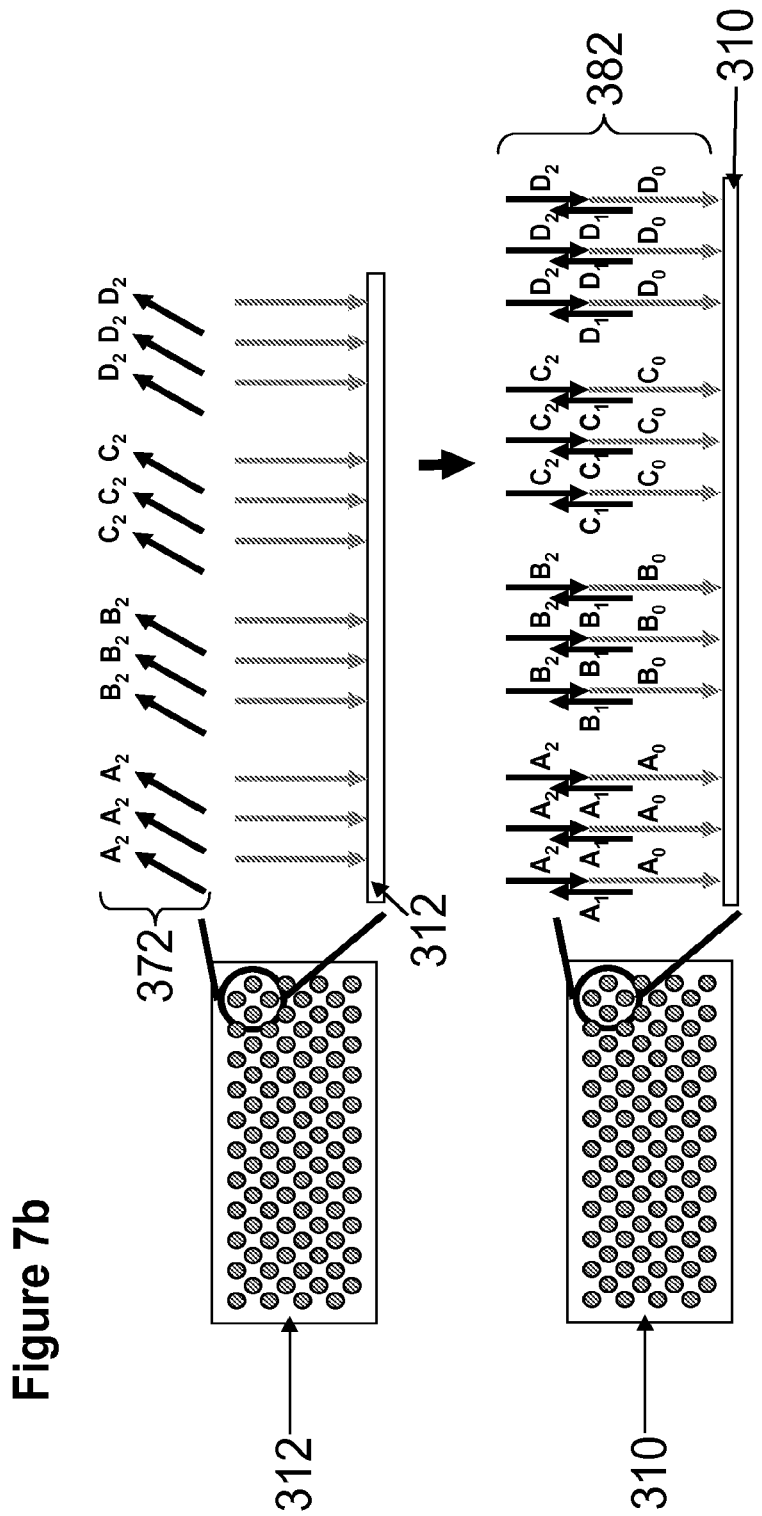

As shown on FIGS. 7a-7b, construction oligonucleotides can be released from the construction array. In some embodiments, the construction oligonucleotides are released under conditions promoting dissociation of the duplexes (e.g. for example under melting temperatures or in presence of an helicase as provided herein). FIGS. 7a-7b illustrates parallel synthesis of a plurality of polynucleotides having different pre-determined sequences by sequential addition of complementary overlapping construction oligonucleotides. Referring to FIG. 7a, a first set of different construction oligonucleotides 371 ($A_1$, $B_1$, $C_1$, $D_1$) are released from construction array 311. In some embodiments, the construction oligonucleotides are transferred and annealed to an anchor array 310 comprising anchor oligonucleotides ($A_0$, $B_0$, $C_0$, $D_0$) having at their 5' end a sequence complementary to the sequence at the 5' end of the first set of construction oligonucleotides 371, thereby forming duplexes 381 (e.g. $A_0A_1$, $B_0B_1$, $C_0C_1$, $D_0D_1$). In preferred embodiments, the first plurality of duplex comprises a 3' free overhang. As illustrated in FIG. 7b, a second population of different construction oligonucleotides 372 ($A_2$, $B_2$, $C_2$, $D_2$) having at one end a sequence complementary to the first plurality of duplex overhang are released from construction array 312. The second population is annealed to the free 3' overhang of the anchor-first construction oligonucleotides duplexes 381 attached the anchor array 310 to form duplexes 382 ($A_0A_1A_2$, $B_0B_1B_2$, $C_0C_1C_2$, $D_0D_1D_2$). In some embodiments, the second plurality of duplexes comprises a 5' free overhang. In some embodiments, a third population of construction oligonucleotides designed to have a sequence complementary to the 5' overhang is annealed to the 5' free overhang of the second plurality of duplexes. Such process can be repeated with additional construction oligonucleotides generated and released from construction arrays until the desired length and sequence of each polynucleotide has been synthesized. In some embodiments, the internal construction oligonucleotides are designed to have a sequence region at their 3' end complementary to the sequence region at the 3' end of a next internal construction oligonucleotide. In some embodiments, each population of construction oligonucleotides is synthesized from different construction arrays and is designed to hybridize to each other to assemble into a longer polynucleotide having a predefined sequence. In some embodiments, the construction oligonucleotide corresponding to the 5' end of the desired polynucleotide has a sequence complementary to a support-bound anchor oligonucleotide. In some embodiments, the construction oligonucleotides are joined using a ligase. In some embodiments, each construction oligonucleotide is annealed to an overhang and the construction oligonucleotides defining one strand of the double-stranded target polynucleotide can be ligated. Construction oligonucleotides may be ligated after each sequential addition of a construction oligonucleotide or may be ligated once the construction oligonucleotides have annealed to each other to form the full length polynucleotide.

In some aspects of the invention, construction oligonucleotides are sequentially transferred from a construction array to an anchor array in a highly parallel fashion. In some embodiments, a plurality of polynucleotides are assembled on a anchor array by sequential alignment, transfer and addition of complementary overlapping oligonucleotides to a plurality of anchor oligonucleotides. In some embodiments, the construction array and the anchor array are brought into close proximity to allow the transfer of construction oligonucleotides from the construction array to the anchor array. Preferably, the construction array is brought to a distance substantially comparable or a distance smaller than the distance between two sets of oligonucleotides ($A_1$, $B_1$ etc. . . . ). In some embodiments, the distance between the construction array and the anchor array is from about 10 μm to about 1000 μm. Desired distances within this range are achieved, in some embodiments, by use of a dilution of spacer spheres (for example, available from Cospheric Microspheres) to a monolayer which keep the two arrays apart under compression. In other embodiments, silicone membranes, for example polydimethylsiloxane (PDMS), is fabricated to encompass one of the arrays in a thin chamber which seals upon bringing the second array to the height of the membrane. In other embodiments, one array can float on top of the other using the liquid medium itself as a spacer. For example, 100 μliters of fluid medium or solution has a thickness of approximately 50 microns when spread evenly over a standard microscope slide can be used.

Figure 8:
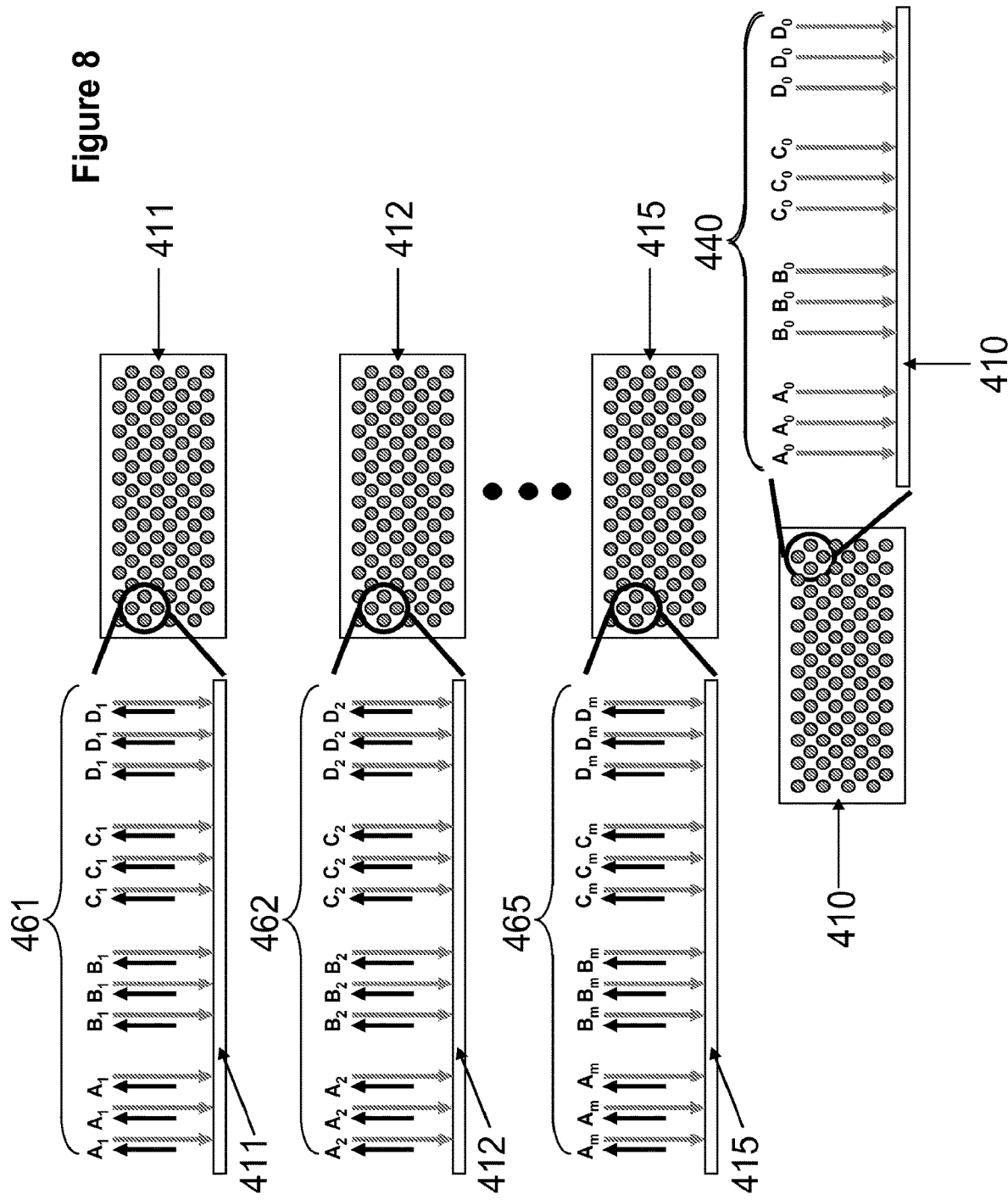
FIG. 8 illustrates an ensemble of construction arrays and an anchor array.

In some embodiments, the plurality of construction oligonucleotides are synthesized onto at least one array as described above. Referring to FIG. 8, a plurality of construction oligonucleotides are synthesized at selected features of at least one construction array (e.g. surface 411), each plurality of oligonucleotides (e.g. $A_1$, $B_1$ $C_1$ $D_1$) having a different predefined sequence. In some embodiments, a plurality of construction oligonucleotides are synthesized at selected features of a plurality of construction supports (e.g. surface 411, 412, 415), each plurality of oligonucleotides having a different predefined sequence. According to some embodiments, construction oligonucleotides are synthesized by primer extension using support-bound oligonucleotides as templates. In some embodiments, a first plurality of oligonucleotides (e.g. oligonucleotides 461 on support 411) may be incubated with a primer in presence of a polymerase, under conditions promoting primer extension. The first plurality of support-bound oligonucleotides can have at its 3' end a sequence designed to be complementary to a primer sequence (e.g. primer binding site). In some embodiments, the primer is a primer containing multiple uracil (e.g. USER™ cleavable primers) and after primer extension the primer is removed using USER™ endonuclease as described herein. Similarly, construction oligonucleotides $A_2$, $B_2$, $C_2$, $D_2$, . . . $A_m$, $B_m$ $C_m$, $D_m$ having a predefined sequence can be synthesized in parallel or sequential fashion by primer extension thereby forming duplexes. As illustrated in FIG. 8, this results in a plurality of arrays having on their surface (411, 12, 415) a plurality of duplexes comprising the construction oligonucleotides and the template oligonucleotides (oligonucleotides 461:$A_1$, $B_1$ $C_1$ $D_1$ on surface 411; oligonucleotides 462 $A_2$, $B_2$ $C_2$ $D_2$ on surface 412; oligonucleotides 465 $A_m$, $B_m$ $C_m$, $D_m$ on surface 415).

Figure 9A:
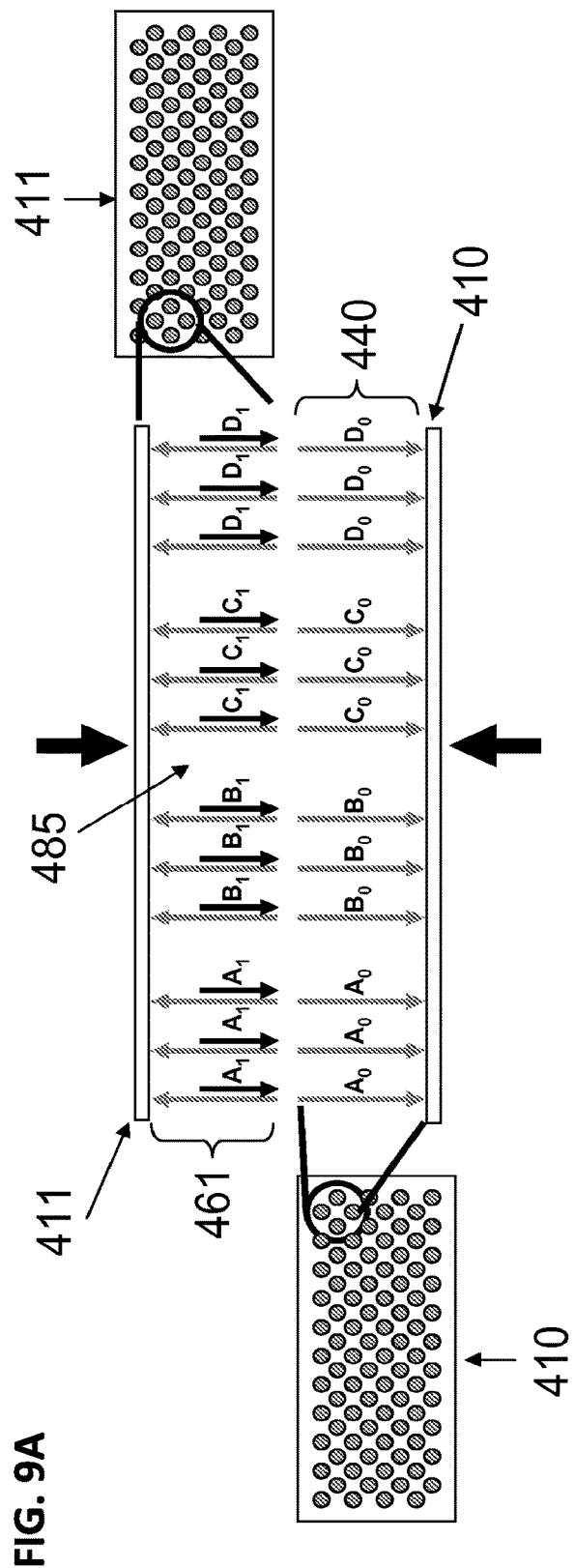
FIGS. 9a-9f illustrate a non-limiting methods for the transfer a first set and second set of construction oligonucleotides from the construction array to the anchor array in a fluid medium.
Figure 9B:
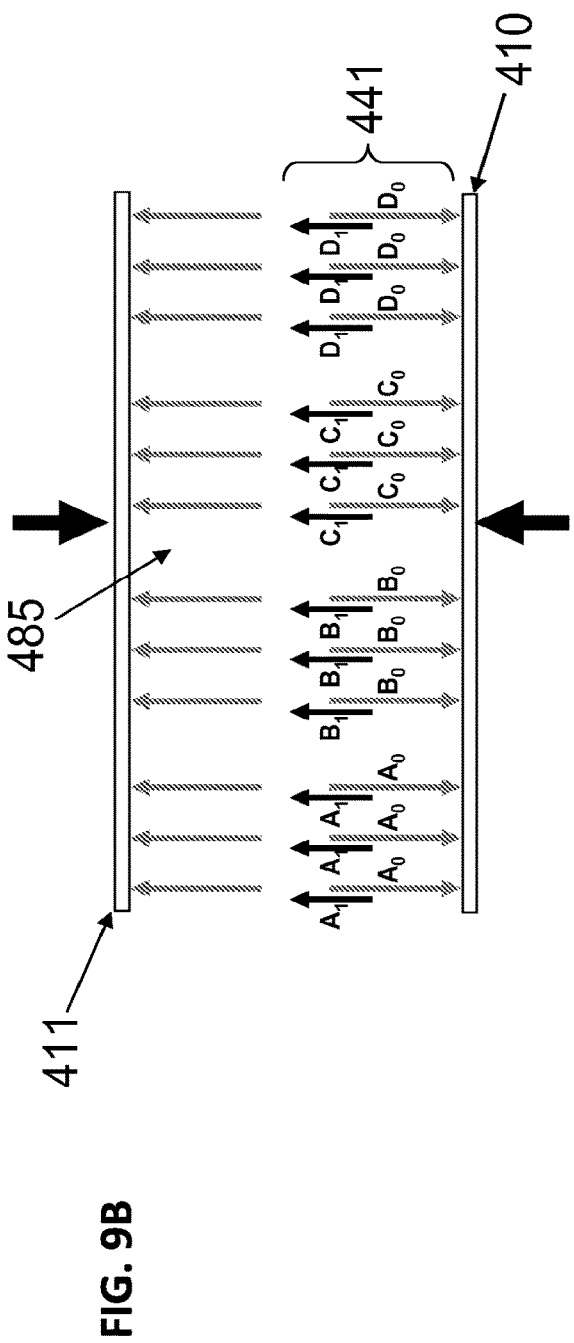
Figure 9C:
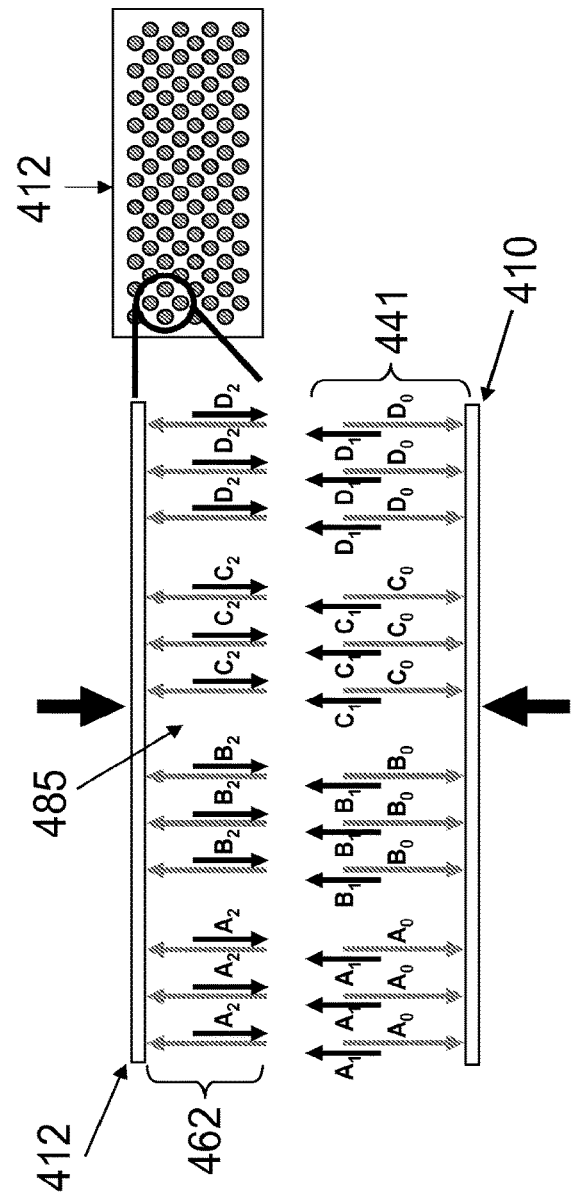

Each of the plurality of construction array may be designed to have the same configuration, each feature being separated from the next feature by the same distance and each feature being similarly arranged on the array. For example, the first support 411 has n features comprising a first, a second and a $n^{th}$ population of oligonucleotides, respectively, each oligonucleotide having a predefined sequence. One would appreciate that each plurality of oligonucleotides can differ from the other plurality of oligonucleotides by one or more bases. Similarly, the support 412 has a first, a second and a $n^{th}$ population of oligonucleotides wherein the first population of oligonucleotides of the first support has sequence complementary to the first population of oligonucleotides of the second support (as illustrated in FIG. 9c). In an exemplary embodiment, the first population of oligonucleotides of the first support has a 3' end sequence complementary to the first population of oligonucleotides of the second support. Similarly, the $m^{th}$ population of oligonucleotides of the $m^{th}$ support has a sequence region complementary to the $(m-1)^{th}$ population of oligonucleotides of the $(m-1)^{th}$ support.

In some embodiments, a first construction array is aligned to an anchor array 410 wherein each feature comprises a support-bound anchor oligonucleotide ($A_0$, $B_0$, $C_0$, $D_0$). Each anchor oligonucleotide can be single-stranded and can comprise at its 5' end a sequence complementary to the 5' terminus of a plurality of oligonucleotides of the first construction array. One should appreciate that for the highly parallel synthesis of a plurality of polynucleotides having a different predefined sequence, each plurality of anchor oligonucleotides can have a different 5' end sequence. In some embodiments, the different 5' end sequence can differ by one or more bases. In some embodiments, the construction array and the anchor array are aligned vertically, the construction array defining to a top array and the anchor array defining to a bottom array. In preferred embodiments, the anchor array and the construction arrays are designed to have the same configuration, each feature being separated from the next feature by the same distance and each feature being similarly arranged on the array. One should appreciate that the design of the construction and anchor arrays enables the alignment of the anchor and the construction oligonucleotides, the anchor oligonucleotides having a sequence complementary to the construction oligonucleotides. After alignment of the construction and anchor arrays, the construction oligonucleotides may be released in solution resulting in the capture and hybridization of the construction oligonucleotides to the anchor oligonucleotides. A second population of construction oligonucleotides immobilized onto a different support can then be brought into close proximity to the anchor array and added sequentially to the duplex comprising the anchor oligonucleotide and the first population of construction oligonucleotides.

Figure 9D:
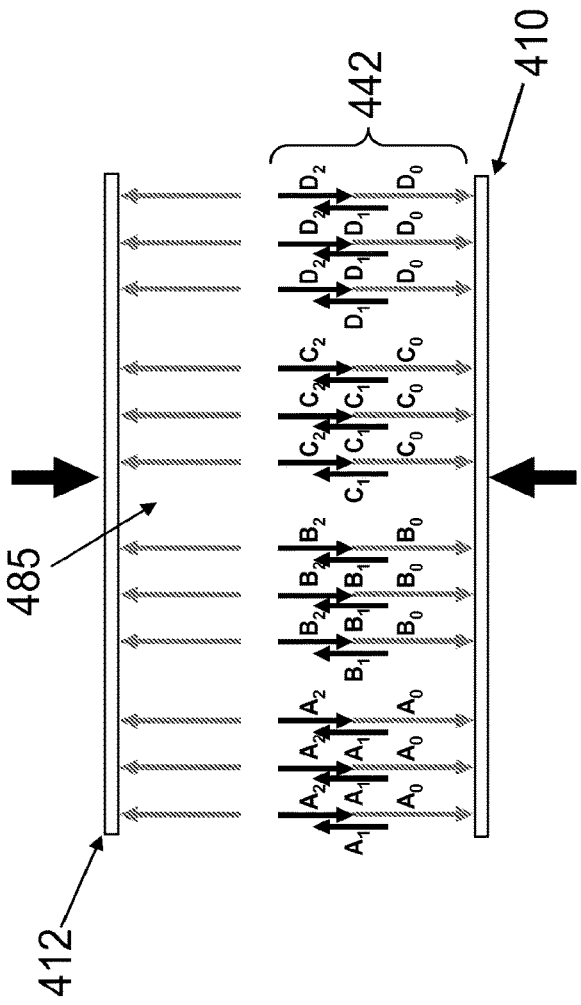

The first construction array can be aligned and approximated to the anchor array. In some, the alignment and approximation of the construction array and anchor array is in presence of a fluid medium or solution which allows for the subsequent proximal diffusion and transfer of construction oligonucleotides from the top construction array to the bottom anchor array (illustrated in a vertical direction in FIGS. 9a-9b). Construction oligonucleotides can be released from the construction array in a fluid medium, for example under conditions promoting dissociation of duplexes. For example, the duplexes 461 can be dissociated by heating selected features or the entire array at a temperature above the melting temperature of the construction oligonucleotide duplexes. Referring to FIGS. 9a-9b, a first set of construction oligonucleotides having different predefined sequences ($A_1$, $B_1$, $C_1$, $D_1$) are released from the duplexes 461 on the first construction array in a fluid medium 485 and captured onto the anchor array forming a plurality of duplexes (e.g. duplexes 441, $A_0A_1$, $B_0B_1$, $C_0C_1$, $D_0D_1$). Referring to FIGS. 9c-9d, a second construction array is aligned and brought into close proximity to the anchor array comprising the anchor-first population construction oligonucleotide duplexes. Alignment and approximation of the second construction array and the anchor array in presence of a fluid medium allows for the subsequent proximal transfer of a second set of construction oligonucleotides from the second construction array to the anchor array. Referring to FIG. 9d, the second set of construction oligonucleotides $A_2$, $B_2$, $C_2$, $D_2$, 462 are released from the microarray 412 and are annealed to anchor microarray 410 to form polynucleotides 442 $A_0A_1A_2$, $B_0B_1B_2$, $C_0C_1C_2$, $D_0D_1D_2$. The resulting assembled polynucleotides may then be ligated by including a ligase, for example Taq DNA ligase and its necessary reaction components, in the fluid medium to form single covalently linked molecules. In some embodiments, the ligase may be supplemented with a non-strand displacing DNA polymerase to fill in gaps and increase the efficiency of ligation. Such process may be repeated with additional members of the construction microarray ensemble until polynucleotides of desired length have been synthesized on the anchor oligonucleotide array.

Figure 9E:
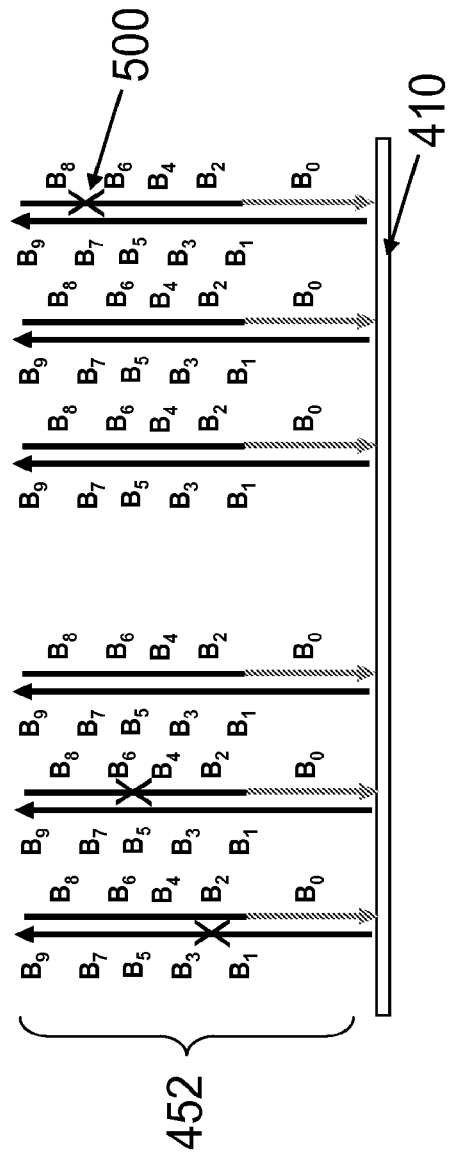
Figure 9F:
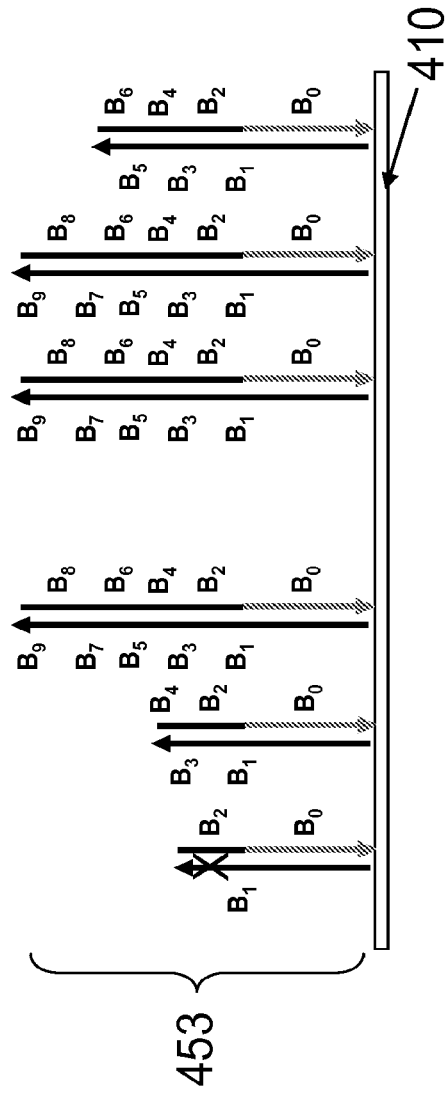

In some embodiments, error correction may be included between each process repetition and/or at the end of the assembly process to increase the relative population of synthesized polynucleotides without deviation from the desired sequences. Such error correction may include direct sequencing and/or the application of error correcting enzymes such as error correcting nucleases (e.g. CEL I), error correction based on MutS or MutS homologs binding or other mismatch binding proteins, other means of error correction as known in the art or any combination thereof. In an exemplary embodiment, CEL I may be added to the oligonucleotide duplexes in the fluid medium. CEL I is a mismatch specific endonuclease that cleaves all types of mismatches such as single nucleotide polymorphisms, small insertions or deletions. Addition of the CEL I endonuclease results in the cleavage of the double-stranded oligonucleotides at the site or region of the mismatch. FIG. 9e depicts an anchor array 410 having on its surface a plurality of polynucleotides 452 which have been assembled by means of the process described in FIGS. 9a-d. The assembled polynucleotides may contain one or more sequence errors 500 (illustrated by a cross). An error correcting nuclease such as CEL I may be used to cleave the double-stranded polynucleotide at such errors sites resulting in cleaved polynucleotides 453 as shown in FIG. 9f.

Figure 10:
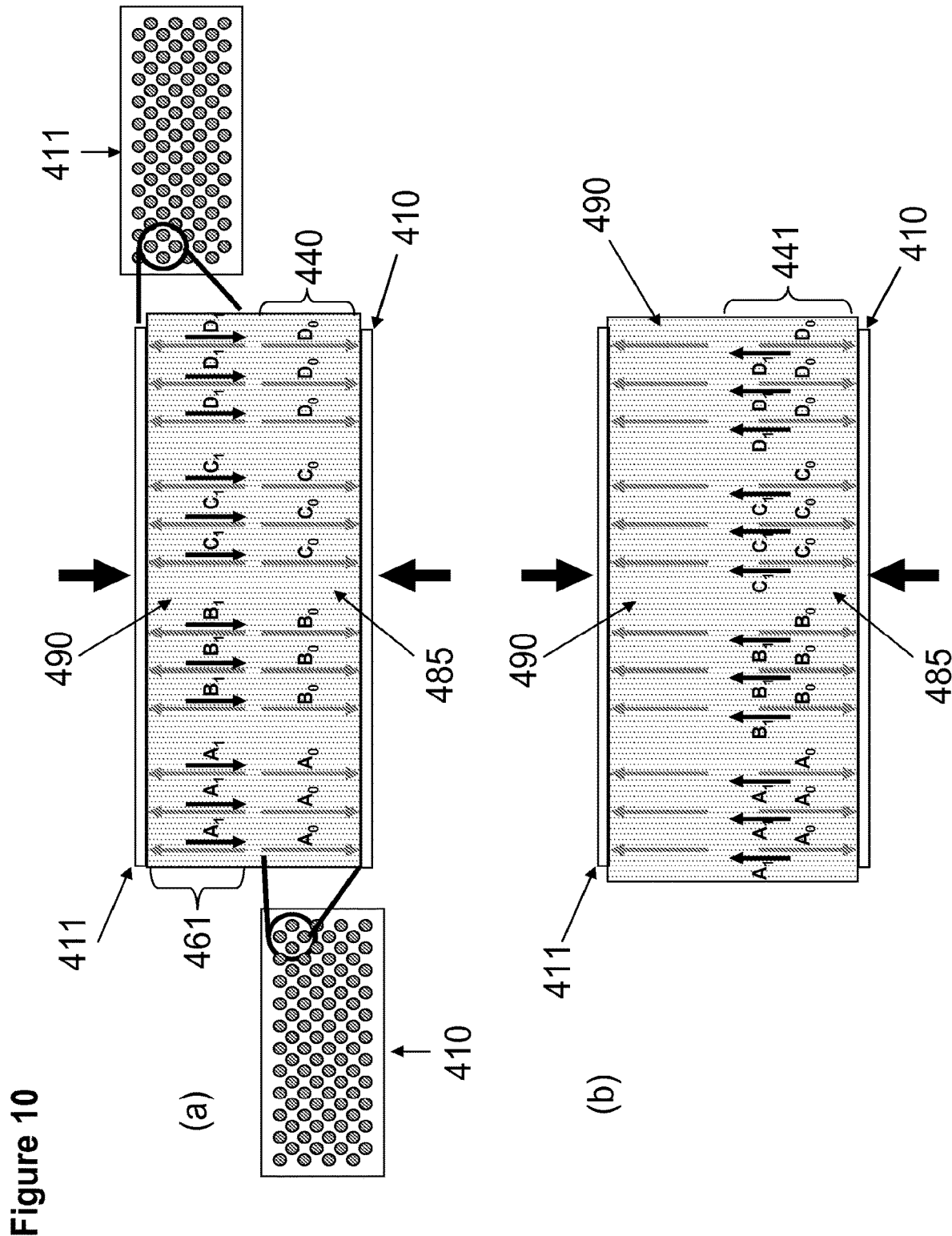
FIG. 10 illustrates a non-limiting method for the transfer of construction oligonucleotides from the construction array to the anchor array in a fluid medium in presence of a porous membrane. Panel (a) illustrates alignment of a top construction array 411 and an anchor array 410 in presence of a fluid medium 485 and a porous membrane 490. Panel (b) illustrates release of construction oligonucleotides ($A_1$, $B_1$, $C_1$, $D_1$) in fluid medium 485 and capture of the oligonucleotides onto the anchor array to form a plurality of duplexes 441 (441, $A_0A_1$, $B_0B_1$, $C_0C_1$, $D_0D_1$).

In some embodiments, the alignment and approximation of the first construction array to the anchor array is in presence of a fluid medium and a porous membrane. According to some embodiments, a porous membrane is placed between the construction array and the anchor array to limit the lateral diffusion of the construction oligonucleotides in the fluid medium towards non-selected features of the anchor array (FIGS. 10a-10b). One should appreciate that the permeable membrane can constrain diffusion of construction oligonucleotide primarily in the vertical direction thus decreasing lateral diffusion of construction oligonucleotides towards non-corresponding anchor oligonucleotides. For example, the membrane can be a porous polymer membrane with pores of uniform size. In some embodiments, the membrane has pore sizes sufficient for the relatively free passage of nucleic acids. In some embodiments, the pore size can range from about 10 nm to about 100 nm or more. Preferably, the pore size is not greater than about the distance between different oligonucleotides $A_1$, $B_1$ etc. In a preferred embodiment, the pore fill factor or aperture ratio is as large as possible. Suitable membranes include those described in: Polymer Membranes with Two-Dimensionally Arranged Pores Derived from Monolayers of Silica Particles, Feng Yan and Werner A. Goedel *Chem. Mater.*, 2004, 16 (9), pp 1622-1626.

Figure 11:
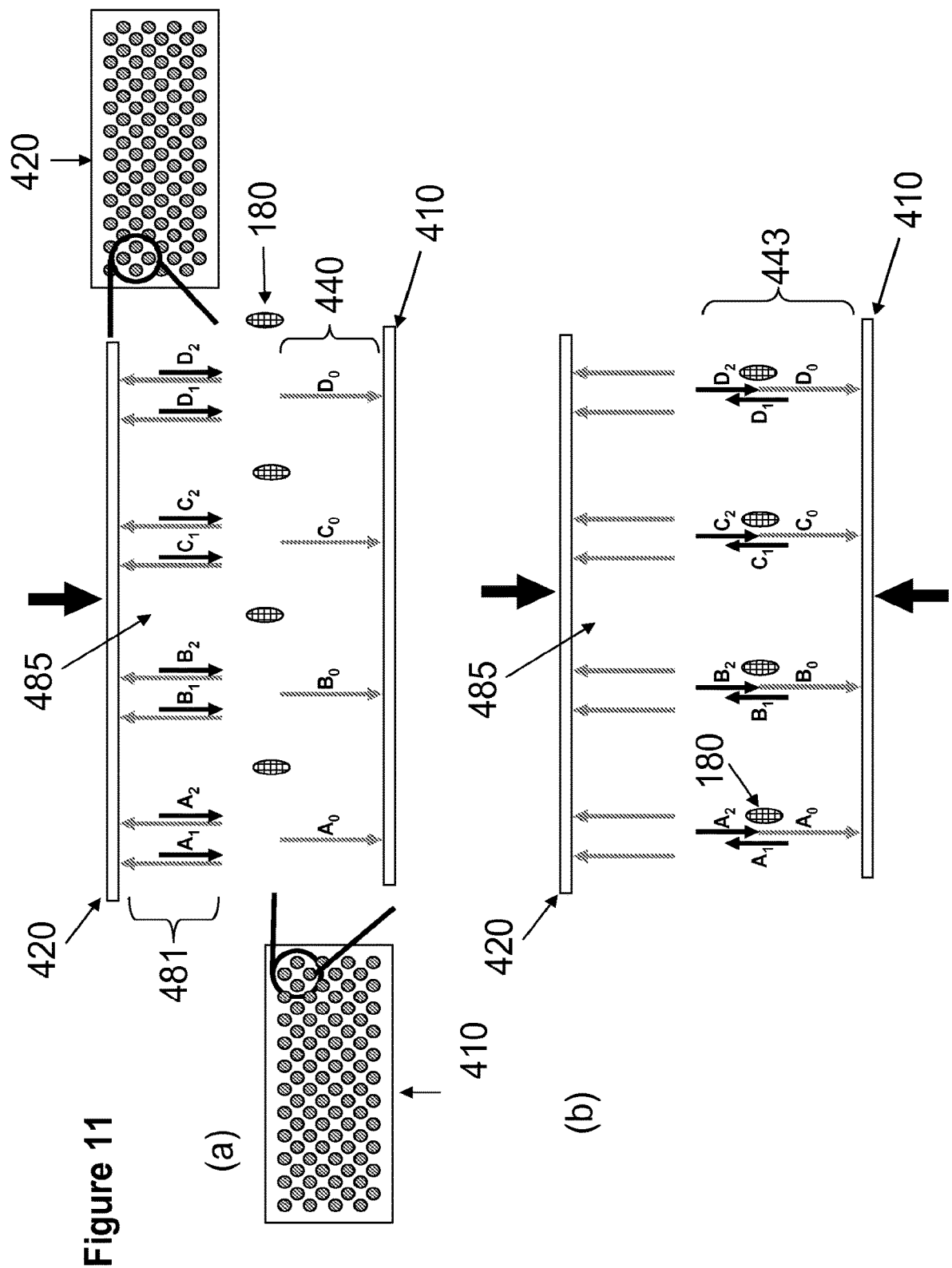
FIG. 11 illustrates a non-limiting method for the transfer of two different construction oligonucleotides from the construction array to the anchor array in a fluid medium and in presence of a ligase. Panel (a) illustrates an alignment and approximation of a first construction array 420 comprising at least two different overlapping construction oligonucleotides 481 to an anchor array 410 in a fluid medium 485 comprising a ligase 180. Panel (b) illustrates proximal transfer of the construction oligonucleotides from the construction array 420 to the anchor array 410 and assembly onto anchor oligonucleotide 440 to form polynucleotide construct 443.

One should appreciate that, for certain situations, it is beneficial to ensure that a high percentage of the available sites on the anchor array captures the construction oligonucleotides, instead of being left unfilled due to recapture of the construction oligonucleotides by the construction array. In order to increase the probability of capture by the anchor array, covalent bonding of at least some of the construction oligonucleotides to the anchor array may be carried out. Referring to FIGS. 11a-11b, a modification of the process detailed in FIGS. 9a-9f is depicted. FIGS. 11a-11b illustrate the alignment and approximation of a first construction array comprising at least two different overlapping construction oligonucleotides to an anchor array in a fluid medium or solution comprising a ligase and the necessary reaction components and the subsequent proximal transfer of the construction oligonucleotides from the construction array to the anchor array. In some embodiments, each feature on a construction oligonucleotide array is designed to contribute two or more overlapping oligonucleotides to be captured by a population of anchor oligonucleotide on a selected feature of the anchor array. Referring to FIG. 11a, each feature of the construction oligonucleotide array 420 carries two construction oligonucleotides 481 (e.g. $A_1$ and $A_2$) per anchor oligonucleotide (e.g. $A_0$). The construction oligonucleotides $A_1$ and $A_2$ may be released into the fluid media or solution 485 residing between construction array 420 and anchor array 410. In some embodiments, the solution further comprises a ligase 180 such that when construction oligonucleotides $A_1$ and $A_2$ assemble onto anchor $A_0$ (FIG. 11b), oligonucleotide $A_2$ is covalently ligated to anchor $A_0$. This arrangement and the presence of ligase provide for the preferred capture of construction oligonucleotides by the anchor oligonucleotide on the anchor array.

In some embodiments, the construction oligonucleotide array(s) and the anchor oligonucleotide array are designed such as the number of construction oligonucleotides to be transferred to the anchor array is in stochiometric excess to each corresponding anchor oligonucleotide. This design allows for a substantially higher probability that the construction oligonucleotides be captured by each of the anchor oligonucleotides, thereby increasing the stepwise yield in the synthesis of the predefined polynucleotides.

Figure 12:
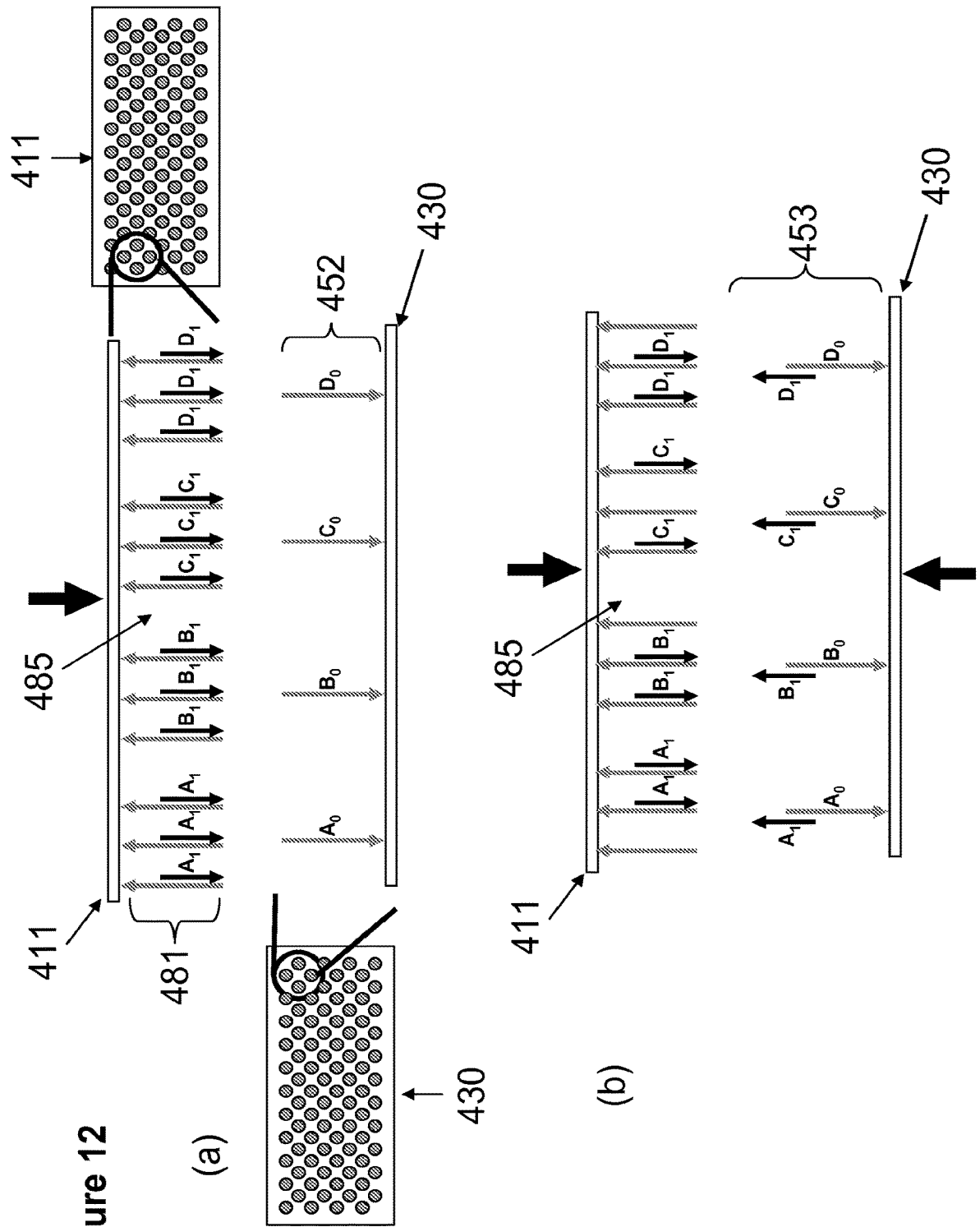
FIG. 12 illustrates a non-limiting method for the transfer of two different construction oligonucleotides from the construction array to the anchor array in a fluid medium wherein the number of construction oligonucleotides is in stochiometric excess to each corresponding anchor oligonucleotide. Panel (a) illustrates alignment of construction oligonucleotide array 411 in relation to the anchor oligonucleotide array 430. Panel (b) illustrates binding of construction oligonucleotides 481 to anchor oligonucleotide 452 on anchor array 430 or recapture of construction oligonucleotides 481 to construction array 411.

FIGS. 12a-12b depicts the alignment and approximation of a first construction array to an anchor array in a fluid medium and the subsequent proximal transfer of construction oligonucleotides from the construction array to the anchor array, in which the number of construction oligonucleotides is in stochiometric excess to each corresponding anchor oligonucleotide. Referring to FIG. 12a, the anchor array 430 is designed such that it comprises stoichiometrically fewer anchor oligonucleotides ($A_0$, $B_0$, $C_0$, $D_0$) as compared to the number of construction oligonucleotides provided by construction array 411 for each corresponding anchor oligonucleotide. This design ensures that the binding of the construction oligonucleotides to each anchor oligonucleotide on the anchor array is stoichiometrically favored. Referring to FIG. 12a and for illustrative purposes, three construction oligonucleotides are depicted at each feature of the construction array 411 for each anchor oligonucleotide on anchor array 430. The construction oligonucleotide array 411 is aligned in relation to the anchor oligonucleotide array 430. Focusing on the alignment of construction oligonucleotide $A_1$ with anchor oligonucleotide $A_0$, after dissociation construction oligonucleotide $A_1$ from its corresponding template oligonucleotide, each of the three copies of $A_1$ has four potential binding sites: each copy of $A_1$ can bind back or be recaptured by the construction array 411 (3 potential sites) or bind to the anchor oligonucleotide $A_0$. After capture, one of the four potential binding sites will remain empty. Since it is equally likely for each of the binding sites to remain empty, the probability that $A_0$ remains empty is 25%, and the probability that $A_0$ is occupied is 75%. In order to increase the binding probability of construction oligonucleotides to the anchor oligonucleotides even further, the ratio of construction oligonucleotides to anchor oligonucleotides may be even further skewed. In some embodiments, the ratio of construction oligonucleotides to anchor oligonucleotides is at least 10:1, at least 100:1, at least 1000:1, at least $10^4$:1, at least $10^5$:1, at least $10^6$:1.

Figure 13:
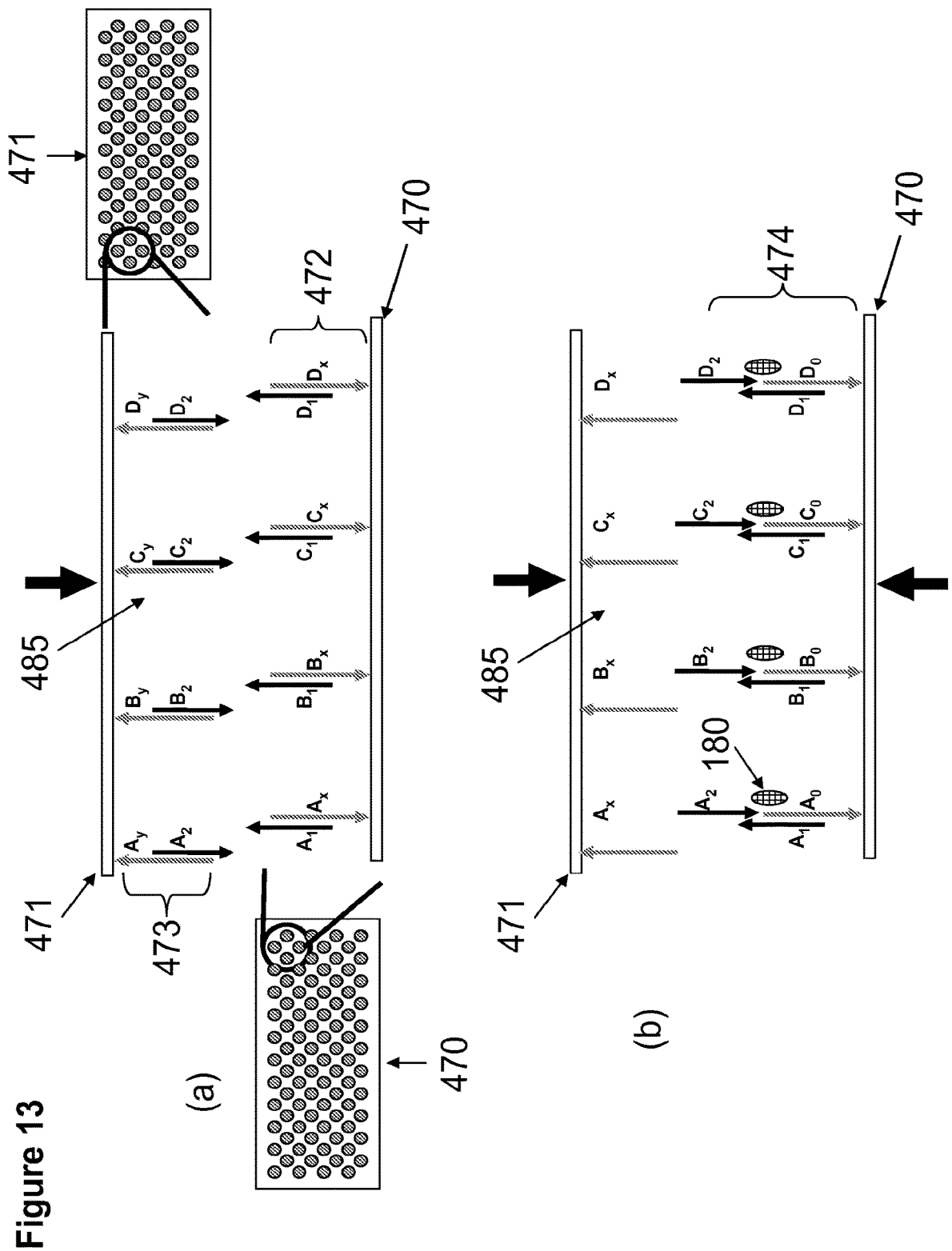
FIG. 13 illustrates a non-limiting method to transfer assembled polynucleotide from one anchor array to those on another anchor array by use of an overlapping junction between the polynucleotides assembled on each anchor array. Panel (a) illustrates two anchor arrays 470 and 471 which have undergone a number of transfers from construction arrays, resulting in surface attached synthesized polynucleotides 472 and 473. Panel (b) illustrates release of polynucleotides and capture onto anchor array 470 in presence of ligase 180.

One should appreciate that a method for increasing the efficiency of construction of desired polynucleotides is to reduce the number of steps in the construction process. In some embodiments, the polynucleotides are synthesized using a hierarchical construction method, where multiple anchor arrays, after several rounds of transfer from construction arrays, may be used themselves as construction arrays in following steps. A hierarchical process geometrically reduces the time to execute the same number of transfers, as well as the number of transfers done on each anchor array, accordingly reducing the impact of stepwise loss. FIG. 13a illustrates two anchor arrays 470 and 471 which have undergone a number of transfers from construction arrays, resulting in surface attached synthesized polynucleotides 472 and 473, respectively. As depicted, one strand of the synthesized polynucleotides has been ligated to the original anchors from said anchor arrays, such that for example, the length of synthesized polynucleotide is longer than that of $A_0$ (if the original anchor array is similar to 410 or 430 from FIGS. 11a-11b or FIGS. 12a-12b, respectively). A release of the polynucleotide strands not ligated to the anchor array results in the transfer of polynucleotides between the arrays as shown in FIG. 13b. The presence of a ligase and the necessary ligation reaction components results in the covalent linkage of the polynucleotides together. One should note that, for illustration purposes, the transfer of polynucleotides is shown from anchor array 471 to anchor array 470, although the transfer will be distributed between both arrays. In order to reduce overall error rate, the surface immobilized synthesized polynucleotides 472 and 473 may first be exposed to a error correcting nuclease as described in the description of FIG. 9e-f. Since some error correcting nucleases cleave at the junction of double and single-stranded nucleic acid, polynucleotides 472 and 473, can be designed to be fully double-stranded or may be converted to double-stranded by adding additional gap filling oligonucleotides to the polynucleotides 472 and 473 followed by ligation.

It should be appreciated that the description of the assembly reactions in the context of oligonucleotides is not intended to be limiting. For example, other polynucleotides (e.g., single-stranded, double-stranded polynucleotides, restriction fragments, amplification products, naturally occurring polynucleotides, etc. . . . ) may be included in an assembly reaction, along with one or more oligonucleotides, in order to generate a polynucleotide of interest.

Aspects of the invention may be useful for a range of applications involving the production and/or use of synthetic nucleic acids. As described herein, the invention provides methods for producing synthetic nucleic acids with increased fidelity and/or for reducing the cost and/or time of synthetic assembly reactions. The resulting assembled nucleic acids may be amplified in vitro (e.g., using PCR, LCR, or any suitable amplification technique), amplified in vivo (e.g., via cloning into a suitable vector), isolated and/or purified.

Figure 14:
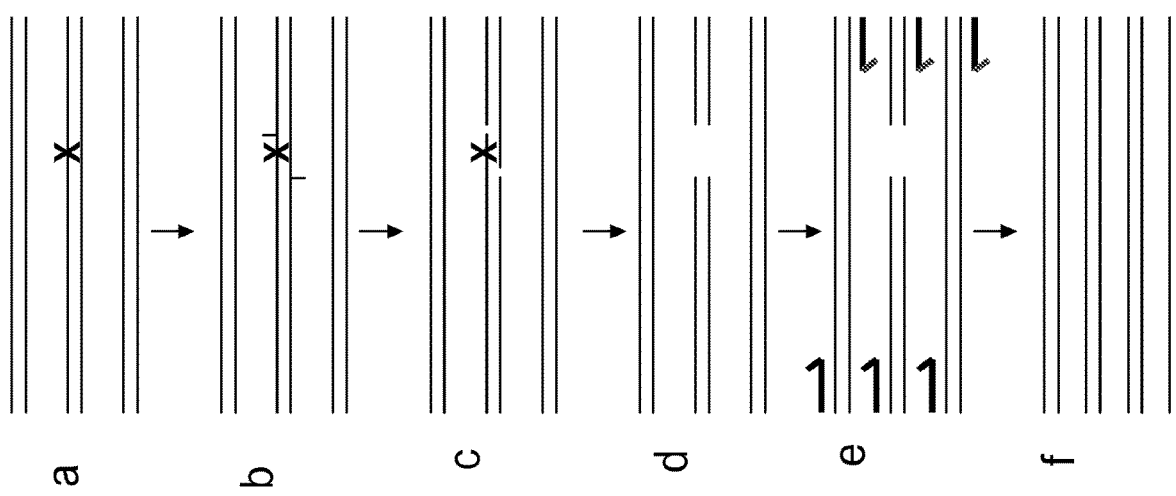
FIG. 14 illustrates a non-limiting method for mismatch error removal from double-stranded nucleic acid sequences using a mismatch-specific endonuclease. Panel (a) illustrates double-stranded nucleic acid sequences having a mismatch. The mismatch nucleotide is indicated by a cross. Panel (b) illustrates the use of mismatch specific endonucleases to cleave the double-stranded nucleic acids at error sites. Panel (c) illustrates cleavage the double-stranded nucleic acids at errors sites resulting in a pool of nucleic acid sequences comprising cleaved error-containing nucleic acids having a 3' overhang and error-free homoduplexes. Panel (d) illustrates removal of mismatch nucleotide(s) to generate a substantially error-free double-stranded nucleic acids pool. Panel (e) illustrates amplification of the pool of nucleic acid sequences using primers. Panel (f) illustrates the amplification products.

Aspects of the methods and devices provided herein may comprise removal of error-containing nucleic acid sequences as described herein. Error-free nucleic acid sequences can be enriched by removal of error-containing sequences or error-containing nucleotide(s). The nucleic acid sequences can be construction oligonucleotides, or assembled products, such as subassemblies or final desired polynucleotides. In some embodiments, the nucleic acid sequences may be released in solution from the support using methods known in the art, such as for example, enzymatic cleavage or amplification. This step can take place in localized individual microvolume(s) containing only the region(s) or feature(s) of interest or in single volume. In some embodiments, removal of the error-containing nucleic acid sequences are performed within a microdroplet. The nucleic acid sequences may be any double-stranded polynucleotide having a predefined sequence. Amplification may be carried out at one or more stages during an assembly process resulting in a pool of double-stranded oligonucleotides or assembled products. One would appreciate that such pool may comprise heteroduplexes (double-stranded nucleic acids sequences having one or more sequence errors) and homoduplexes (error free double-stranded nucleic acid sequences or double-stranded nucleic acid sequences having complementary sequences errors). As illustrated in FIG. 14a, the double-stranded nucleic acids may contain one or more sequence errors (heteroduplexes illustrated by a cross). CEL nucleases (CEL I or CEL II) are mismatch—specific endonucleases known to cut double-stranded nucleic acid in both strands at sites of single-base substitution, small deletion or small insertion. CEL I cleaved the nucleic acid on the 3' side of the mismatch site, generating a single-stranded 3' overhang of one or more nucleotides. In some embodiments, the endonuclease CEL I (SURVEYOR®) can be used to cleave the double-stranded nucleic acids at such errors sites resulting in a pool of nucleic acid sequences comprising cleaved error-containing nucleic acids having a 3' overhang, and error-free homoduplexes as illustrated in FIG. 14c. The mismatch nucleotide(s) can be removed using a T4 polymerase and/or a Klenow polymerase having a 3'-5' exonuclease activity, thereby generating a substantially error-free double-stranded nucleic acids pool (homoduplexes as shown in FIG. 14d). In some embodiments, the pool of nucleic acid sequences can then amplified, such as by polymerase chain reaction, PCR), using end primers (FIG. 14e). Primers may be universal primers, semi-universal primers or primer specific to the terminal sequence of the nucleic acid molecule. In some embodiments, duplexes are first allowed to dissociate and re-anneal before subjecting the pool of nucleic acids to amplification. This process will allow for detection and removal of complementary errors that may have remained undetected by the mismatch-specific endonucleases.

An assembled nucleic acid (alone or cloned into a vector) may be transformed into a host cell (e.g., a prokaryotic, eukaryotic, insect, mammalian, or other host cell). In some embodiments, the host cell may be used to propagate the nucleic acid. In certain embodiments, the nucleic acid may be integrated into the genome of the host cell. In some embodiments, the nucleic acid may replace a corresponding nucleic acid region on the genome of the cell (e.g., via homologous recombination). Accordingly, nucleic acids may be used to produce recombinant organisms. In some embodiments, a target nucleic acid may be an entire genome or large fragments of a genome that are used to replace all or part of the genome of a host organism. Recombinant organisms also may be used for a variety of research, industrial, agricultural, and/or medical applications.

In some embodiments, methods described herein may be used during the assembly of large nucleic acid molecules (for example, larger than 5,000 nucleotides in length, e.g., longer than about 10,000, longer than about 25,000, longer than about 50,000, longer than about 75,000, longer than about 100,000 nucleotides, etc.). In an exemplary embodiment, methods described herein may be used during the assembly of an entire genome (or a large fragment thereof, e.g., about 10%, 20%, 30%, 40%, 50%, 60%, 70%, 80%, 90%, or more) of an organism (e.g., of a viral, bacterial, yeast, or other prokaryotic or eukaryotic organism), optionally incorporating specific modifications into the sequence at one or more desired locations.

Aspects of the methods and devices provided herein may include automating one or more acts described herein. In some embodiments, one or more steps of an amplification and/or assembly reaction may be automated using one or more automated sample handling devices (e.g., one or more automated liquid or fluid handling devices). Automated devices and procedures may be used to deliver reaction reagents, including one or more of the following: starting nucleic acids, buffers, enzymes (e.g., one or more ligases and/or polymerases), nucleotides, salts, and any other suitable agents such as stabilizing agents. Automated devices and procedures also may be used to control the reaction conditions. For example, an automated thermal cycler may be used to control reaction temperatures and any temperature cycles that may be used. In some embodiments, a scanning laser may be automated to provide one or more reaction temperatures or temperature cycles suitable for incubating polynucleotides. Similarly, subsequent analysis of assembled polynucleotide products may be automated. For example, sequencing may be automated using a sequencing device and automated sequencing protocols. Additional steps (e.g., amplification, cloning, etc.) also may be automated using one or more appropriate devices and related protocols. It should be appreciated that one or more of the device or device components described herein may be combined in a system (e.g., a robotic system) or in a micro-environment (e.g., a micro-fluidic reaction chamber). Assembly reaction mixtures (e.g., liquid reaction samples) may be transferred from one component of the system to another using automated devices and procedures (e.g., robotic manipulation and/or transfer of samples and/or sample containers, including automated pipetting devices, micro-systems, etc.). The system and any components thereof may be controlled by a control system.

Accordingly, method steps and/or aspects of the devices provided herein may be automated using, for example, a computer system (e.g., a computer controlled system). A computer system on which aspects of the technology provided herein can be implemented may include a computer for any type of processing (e.g., sequence analysis and/or automated device control as described herein). However, it should be appreciated that certain processing steps may be provided by one or more of the automated devices that are part of the assembly system. In some embodiments, a computer system may include two or more computers. For example, one computer may be coupled, via a network, to a second computer. One computer may perform sequence analysis. The second computer may control one or more of the automated synthesis and assembly devices in the system. In other aspects, additional computers may be included in the network to control one or more of the analysis or processing acts. Each computer may include a memory and processor. The computers can take any form, as the aspects of the technology provided herein are not limited to being implemented on any particular computer platform. Similarly, the network can take any form, including a private network or a public network (e.g., the Internet). Display devices can be associated with one or more of the devices and computers. Alternatively, or in addition, a display device may be located at a remote site and connected for displaying the output of an analysis in accordance with the technology provided herein. Connections between the different components of the system may be via wire, optical fiber, wireless transmission, satellite transmission, any other suitable transmission, or any combination of two or more of the above.

Each of the different aspects, embodiments, or acts of the technology provided herein can be independently automated and implemented in any of numerous ways. For example, each aspect, embodiment, or act can be independently implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments of the technology provided herein comprises at least one computer-readable medium (e.g., a computer memory, a floppy disk, a compact disk, a tape, etc.) encoded with a computer program (i.e., a plurality of instructions), which, when executed on a processor, performs one or more of the above-discussed functions of the technology provided herein. The computer-readable medium can be transportable such that the program stored thereon can be loaded onto any computer system resource to implement one or more functions of the technology provided herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the technology provided herein.

It should be appreciated that in accordance with several embodiments of the technology provided herein wherein processes are stored in a computer readable medium, the computer implemented processes may, during the course of their execution, receive input manually (e.g., from a user).

Accordingly, overall system-level control of the assembly devices or components described herein may be performed by a system controller which may provide control signals to the associated nucleic acid synthesizers, liquid handling devices, thermal cyclers, sequencing devices, associated robotic components, as well as other suitable systems for performing the desired input/output or other control functions. Thus, the system controller along with any device controllers together form a controller that controls the operation of a nucleic acid assembly system. The controller may include a general purpose data processing system, which can be a general purpose computer, or network of general purpose computers, and other associated devices, including communications devices, modems, and/or other circuitry or components to perform the desired input/output or other functions. The controller can also be implemented, at least in part, as a single special purpose integrated circuit (e.g., ASIC) or an array of ASICs, each having a main or central processor section for overall, system-level control, and separate sections dedicated to performing various different specific computations, functions and other processes under the control of the central processor section. The controller can also be implemented using a plurality of separate dedicated programmable integrated or other electronic circuits or devices, e.g., hard wired electronic or logic circuits such as discrete element circuits or programmable logic devices. The controller can also include any other components or devices, such as user input/output devices (monitors, displays, printers, a keyboard, a user pointing device, touch screen, or other user interface, etc.), data storage devices, drive motors, linkages, valve controllers, robotic devices, vacuum and other pumps, pressure sensors, detectors, power supplies, pulse sources, communication devices or other electronic circuitry or components, and so on. The controller also may control operation of other portions of a system, such as automated client order processing, quality control, packaging, shipping, billing, etc., to perform other suitable functions known in the art but not described in detail herein.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EQUIVALENTS

The present invention provides among other things novel methods and devices for high-fidelity gene assembly. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

Reference is made to U.S. provisional application 61/412,937. filed Nov. 12, 2010 entitled "Methods and Devices for Nucleic Acids Synthesis"; U.S. provisional application 61/418,095 filed Nov. 30, 2010 entitled "Methods and Devices for Nucleic Acids Synthesis" and U.S. provisional application 61/466,814, filed Mar. 23, 2011, entitled "Methods and Devices for Nucleic Acids Synthesis", to PCT application PCT/US2009/55267 filed Aug. 27, 2009, PCT Application PCT/US2010/055298 filed Nov. 3, 2010 and PCT Application PCT/US2010/057405 filed Nov. 19, 2010.

All publications, patents and sequence database entries mentioned herein are hereby incorporated by reference in their entirety as if each individual publication or patent was specifically and individually indicated to be incorporated by reference.

What is claimed is:

1. A method of generating a polynucleotide having a predefined sequence, the method comprising:
   (a) synthesizing a plurality of support-bound double-stranded polynucleotides, each support-bound double-stranded polynucleotide comprising one or more construction oligonucleotides and a free single-stranded overhang, the plurality of support-bound double-stranded polynucleotide sequences comprising the polynucleotide having the predefined sequence, wherein the single-stranded overhang comprises the sequence of a terminal construction oligonucleotide N;
   (b) providing a stem-loop oligonucleotide comprising a single-stranded overhang wherein the single-stranded overhang is complementary to the sequence of the terminal construction oligonucleotide N;
   (c) hybridizing the stem-loop oligonucleotide to the free overhang of the polynucleotide having the predefined sequence;
   (d) ligating the stem-loop oligonucleotide to the free overhang of the polynucleotide having the predefined sequence; and
   (e) degrading, using an exonuclease, polynucleotide sequences that comprise a free 3' or 5' end, and that do not comprise the terminal construction oligonucleotide N.

2. The method of claim 1, wherein the step of synthesizing comprises hybridizing a pool of oligonucleotides comprising N pluralities of construction oligonucleotides to a plurality of anchor support-bound single-stranded oligonucleotides, wherein the first plurality of construction oligonucleotides in the pool comprises at its 5' end a sequence region that is complementary to a sequence region at the 5' end of the plurality of anchor oligonucleotides, and wherein a plurality of construction oligonucleotides N comprises at its 3' end a sequence complementary to a sequence region of the plurality of construction oligonucleotides (N−1).

3. The method of claim 1, further comprising degrading the polynucleotide sequences that do not comprise the terminal oligonucleotide sequence using a single strand specific exonuclease.

4. The method of claim 1, wherein the exonuclease is a single strand-specific 3' exonuclease, or a single strand-specific 5' exonuclease.

5. The method of claim 1, wherein the stem-loop oligonucleotide comprises a type II restriction site.

6. The method of claim 1, wherein the method further comprises removing the stem-loop oligonucleotide using a type II restriction endonuclease.

7. The method of claim 1, wherein the stem-loop oligonucleotide comprises at least one Uracil nucleotide.

8. The method of claim 1, wherein the method further comprises removing the stem-loop oligonucleotide using a mixture of Uracil DNA glycosylase (UDG) and a DNA glycosylase-lyase Endonuclease VIII.

9. The method of claim 1, further comprising amplifying the predefined polynucleotide having the predefined sequence.

10. The method of claim 1, wherein in the step of synthesizing the plurality of support-bound double-stranded polynucleotides is synthesized on a support by polymerase chain extension.

11. The method of claim 1, further comprising releasing the polynucleotide having the predefined sequence from the support.

12. The method of claim 11, wherein the polynucleotides are released using a Type II restriction enzyme or a mixture of Uracil DNA glycosylase (UDG) and a DNA glycosylase-lyase Endonuclease VIII.

* * * * *

UNITED STATES PATENT AND TRADEMARK OFFICE
CERTIFICATE OF CORRECTION

PATENT NO. : 11,084,014 B2
APPLICATION NO. : 16/533892
DATED : August 10, 2021
INVENTOR(S) : Joseph Jacobson et al.

Page 1 of 1

It is certified that error appears in the above-identified patent and that said Letters Patent is hereby corrected as shown below:

In the Claims

Claim 9, Column 40, Line 24, 'the predefined polynucleotide' should be changed to -- the polynucleotide --.

Signed and Sealed this
Twenty-fifth Day of January, 2022

Drew Hirshfeld
*Performing the Functions and Duties of the
Under Secretary of Commerce for Intellectual Property and
Director of the United States Patent and Trademark Office*